United States Patent [19]

Kato et al.

[11] Patent Number: 5,709,820
[45] Date of Patent: Jan. 20, 1998

[54] ALKENYL CYCLOHEXANE DERIVATIVES AND LIQUID CRYSTAL COMPOSITIONS

[75] Inventors: Takashi Kato; Shuichi Matsui; Kazutoshi Miyazawa; Yasuko Sekiguchi; Etsuo Nakagawa, all of Ichihara, Japan

[73] Assignee: Chisso Corporation, Osaka, Japan

[21] Appl. No.: 655,965

[22] Filed: May 31, 1996

[30] Foreign Application Priority Data

Jun. 5, 1995 [JP] Japan .................... 7-161417

[51] Int. Cl.$^6$ .................... C09K 19/34; C09K 19/30; C07D 319/06
[52] U.S. Cl. .................... 252/299.61; 252/299.63; 252/299.01; 549/357; 549/369; 549/377
[58] Field of Search .................... 252/299.63, 299.01, 252/299.61; 549/357, 369, 377

[56] References Cited

U.S. PATENT DOCUMENTS

| | | | |
|---|---|---|---|
| 4,565,425 | 1/1986 | Petrzilka et al. | 252/299.61 |
| 4,621,901 | 11/1986 | Petrzilka et al. | 252/299.63 |
| 4,676,604 | 6/1987 | Petrzilka | 252/299.63 |
| 5,013,478 | 5/1991 | Petrzilka | 252/299.63 |
| 5,180,519 | 1/1993 | Uchida et al. | 252/299.63 |
| 5,238,602 | 8/1993 | Petrzilka et al. | 252/299.65 |
| 5,264,149 | 11/1993 | Buchecker et al. | 252/299.63 |
| 5,382,379 | 1/1995 | Onji et al. | 252/299.63 |

FOREIGN PATENT DOCUMENTS

| | | |
|---|---|---|
| 0 388 150 | 9/1990 | European Pat. Off. |
| 0 427 957 | 5/1991 | European Pat. Off. |
| 0 679 707 | 11/1995 | European Pat. Off. |
| 44 14 647 | 11/1995 | Germany |
| 57-165328 | 10/1982 | Japan |
| 59-164788 | 9/1984 | Japan |
| 59-176221 | 10/1984 | Japan |
| 61-56137 | 3/1986 | Japan |
| 61-83136 | 4/1986 | Japan |
| 63-502284 | 9/1988 | Japan |
| 5-286873 | 11/1993 | Japan |
| 6-247886 | 9/1994 | Japan |
| 2 073 175 | 10/1981 | United Kingdom |

OTHER PUBLICATIONS

Journal De Physique, Suppl. No. 3, 36, p. C1–379–383, Mar. 1975, "Liquid Crystals With Hydroaromatic And Hydroheterocyclic Structures;" H. Schubert, et al.

Molecular Crystals and Liquid Crystals, vol. 49, No. 1, pp. 217–222, 1978, Jean Billard, et al., "Mesophases De Derives Du Cyclohexane".

*Primary Examiner*—Shean C. Wu
*Attorney, Agent, or Firm*—Oblon, Spivak, McClelland, Maier & Neustadt, P.C.

[57] ABSTRACT

Liquid crystalline alkenyl cyclohexane compounds of formula (I) having a nematic phase over a broad temperature range, a higher elastic constant ratio $K_{33}/K_{11}$ and a lower viscosity, liquid crystal compositions comprising the above compounds and liquid crystal display elements using the liquid crystal compositions.

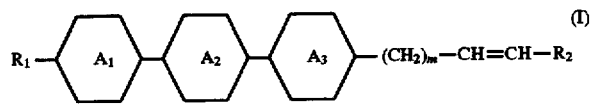

wherein $R_1$ is an alkyl group of 1–15 carbons, an alkenyl group of 2–15 carbons or an alkyl or alkenyl group in which at least one of non-adjacent methylene groups (—$CH_2$—) is replaced by —O—, —S—, —C≡C— or —COO—; $R_2$ is a hydrogen atom or an alkyl group of 1–10 carbons; m is 0–5; when m is 2 or more, any one methylene group in —$(CH_2)_m$— may be replaced by —O—; and the rings $A_1$, $A_2$ and $A_3$ are independently a 1,4-cyclohexylene, a cyclohexene-1,4-diyl or a 6-membered ring group, one or two —$CH_2$— groups in said rings optionally replaced by —O— or —S—.

14 Claims, No Drawings

ALKENYL CYCLOHEXANE DERIVATIVES AND LIQUID CRYSTAL COMPOSITIONS

FIELD OF THE INVENTION

This invention relates to a liquid crystalline compound and a liquid crystal composition containing the same. More particularly, it relates to a new liquid crystalline tricyclic compound having an alkenyl group (alkenyl cyclohexane derivatives), a liquid crystal composition containing the same and a liquid crystal display element using the composition.

BACKGROUND OF THE INVENTION

Many display elements have been prepared utilizing the characteristics of liquid crystalline compounds such as optical anisotropy and dielectric anisotropy. These elements have been widely used as various applications including watch, calculator, word processor, television or the like, a demand for which is increasing.

A liquid crystal phase is positioned between a solid phase and a liquid phase and is classified roughly into a nematic phase, a smectic phase and a cholesteric phase. A display element using a nematic phase has been inter alia most widely used. As a display mode, various modes have been proposed, but presently three types of twisted nematic (TN) mode, supertwisted nematic (STN) mode and thin film transistor (TFT) mode have been mainly used. In particular, the STN mode is a synthetically excellent mode as a liquid crystal display with a simple matrix mode drive, in view of various characteristics such as display capacity, response speed, angle of view, gradient and others. Further, the STN mode has been widely used in a color display, since it is more inexpensive than the TFT mode.

A liquid crystalline compound required for such display modes should show a liquid crystal phase over a broad temperature range centering in room temperature, a sufficient stability under conditions wherein a display element is used, and sufficient characteristics to drive a display element. However, no single liquid crystalline substance has been found satisfying all such requirements. Now, current status is to prepare a liquid crystal composition having the required characteristics by admixing several to several tens types of liquid crystalline compounds and, if necessary, non-liquid crystalline compounds and to use the composition for a display element.

A liquid crystal composition is required to be extremely stable to moisture, light, heat or air under the condition in which a display element is used, to be stable to an electric field or electromagnetic radiation and further to be chemically stable to any compounds to be admixed. Moreover, a liquid crystal composition should have suitable numerical values, depending upon a display mode or a shape of a display element, of various characteristics such as its optical anisotropy ($\Delta n$), dielectric anisotropy ($\Delta \epsilon$), viscosity ($\eta$) and elastic constant ratio $K_{33}/K_{11}$ ($K_{33}$: Bending elastic constant, $K_{11}$: Spraying elastic constant) and the like. In addition, it is important that each component in a liquid crystal composition should have a good solubility. Under the present circumstances wherein colorization of a display and use environments of a display have been diversified, particularly required characteristics are a broad temperature range of a nematic phase, a high elastic constant ratio $K_{33}/K_{11}$, a lower viscosity and a mutual good solubility. As the elastic constant ratio $K_{33}/K_{11}$ is increased, a steep change in transmittance in the neighborhood of the threshold voltage is brought about to provide a display element with a higher contrast. On the other hand, as the viscosity is reduced, there is provided a display element with a rapid response speed. Those two physical characteristics have been required for the colorization of a display, while a broad temperature range of a nematic phase has been required for the diversification of use environments of a display.

As prior tricyclic compounds having a high NI point and a low viscosity, the following compounds are disclosed:

(a) compounds disclosed in Japanese Patent Kokai No. 57-165328

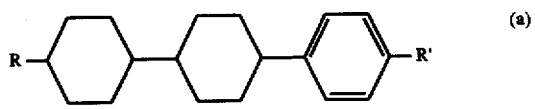

(b) compounds disclosed in Japanese Patent Kokai No. 05-286873

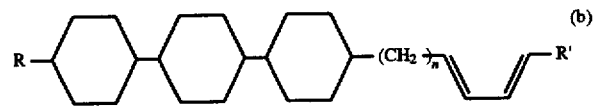

and (c) compounds disclosed in Journal de Physique, Suppl. No. 3, 36, C1-379, March 1975

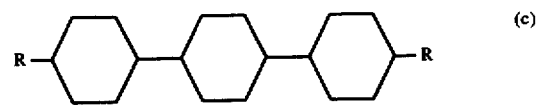

In the above formulae, R and R' represent an alkyl group.

Both compounds (a) and (b) are the tricyclic compounds having alkyl groups at both ends, but compounds (a) have a low NI point and a high viscosity and a lower elastic constant ratio $K_{33}/K_{11}$ with no good compatibility at a lower temperature. Compounds (b) have a relatively lower viscosity, but a very poor stability due to the presence of a conjugated diene in the side chain. Compounds (c) have a lower elastic constant ratio $K_{33}/K_{11}$ similarly to compounds (a) and are not said to have a particularly favorable compatibility at a lower temperature.

The liquid crystalline compounds having an alkenyl group with a higher elastic constant ratio are disclosed in Japanese Patent Kokai Nos. 59-176221, 61-56137 and 61-83136 and Japanese Patent Kohyo No. 63-502284, but none of them could satisfy the requirements for all characteristics of a lower viscosity, a good compatibility at a lower temperature and a higher NI point.

In an effort to overcome these problems, the development of a liquid crystalline compound with improved characteristics has been expected.

DETAILED DESCRIPTION OF THE INVENTION

An object of this invention is to provide a liquid crystalline compound which exhibits a nematic phase particularly over a broad temperature range, has a higher elastic constant ratio $K_{33}/K_{11}$ and a lower viscosity, in order to solve the prior art problems.

Another object of the invention is to provide a liquid crystal composition comprising the liquid crystalline compound.

Further object of the invention is to provide a liquid crystal display element using the liquid crystal composition.

According to the present invention, there is provided a liquid crystalline compound of formula (I)

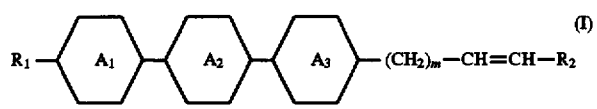

(I)

wherein $R_1$ is an alkyl group of 1–15 carbons, an alkenyl group of 2–15 carbons or an alkyl or alkenyl group in which at least one of non-adjacent methylene groups (—$CH_2$—) is replaced by —O—, —S—, —C≡C— or —COO—; $R_2$ is a hydrogen atom or an alkyl group of 1–10 carbons; m is 0–5; when m is 2 or more, any one methylene group in —$(CH_2)_m$— may be replaced by —O—; and the rings $A_1$, $A_2$ and $A_3$ are independently a 1,4-cyclohexylene or a cyclohexene-1,4-diyl, one or two —$CH_2$— groups in said rings optionally replaced by —O— or —S—.

In the preferred embodiments of the present invention, the liquid crystalline compounds include those of formula (I) wherein m is 0; m is 2; m is 0 and $R_1$ is an alkenyl group; and m is 2 and $R_1$ is an alkenyl group.

It should be understood that all the hydrogen atoms in the compounds of formula (I) may be replaced by deuterium and the corresponding compounds thus replaced are included within the scope of the present invention.

According to another aspect of the present invention, there is provided a liquid crystal composition which comprises at least one of the liquid crystalline compounds of formula (I).

The present invention also provides a liquid crystal composition which comprises:

(i) as a first component, at least one of the compounds of formula (I), and (ii) as a second component, at least one compound selected from the group consisting of the compounds of formulae (II-a), (II-b) and (II-c)

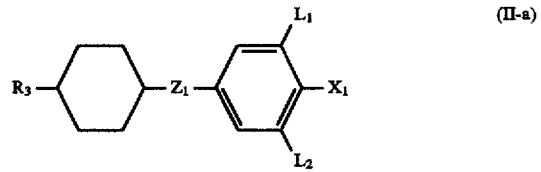

(II-a)

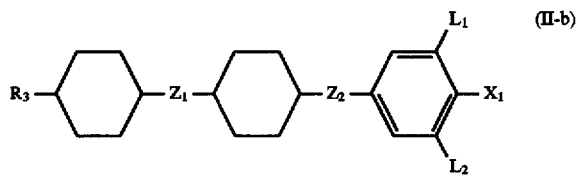

(II-b)

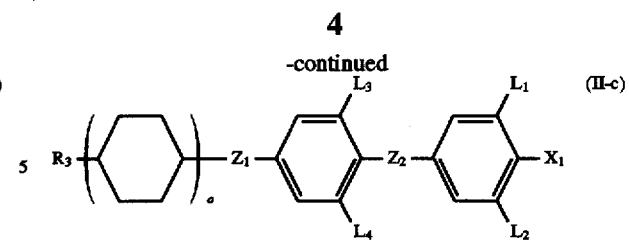

(II-c)

wherein $R_3$ is an alkyl group of 1–10 carbons, $X_1$ is F, Cl, $OCF_3$, $OCF_2H$, $CF_3$, $CF_2H$ or $CFH_2$, $L_1$, $L_2$, $L_3$ and $L_4$ are independently H or F, $Z_1$ and $Z_2$ are independently —$(CH_2)_2$—, —CH=CH— or a covalent bond and a is 1 or 2.

Further, the present invention provides a liquid crystal composition which comprises:

(i) as a first component, at least one of the compounds of formula (I), (ii) as a second component, at least one compound selected from the group consisting of the compounds of formulae (III-a), (III-b), (III-c), (III-d) and (III-e)

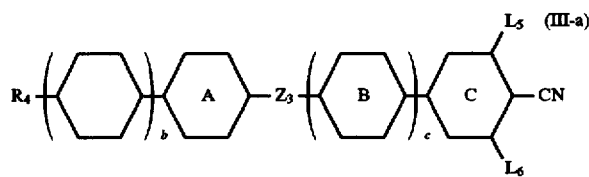

(III-a)

wherein $R_4$ is F, an alkyl group of 1–10 carbons or an alkenyl group of 2–10 carbons, the methylene group (—$CH_2$—) in said alkyl or alkenyl group may be replaced by an oxygen atom (—O—) provided that two or more methylene groups in series are not replaced by an oxygen atom, the ring A is a trans-1,4-cyclohexylene, 1,4-phenylene, pyrimidine-2,5-diyl or 1,3-dioxane-2,5-diyl group, the ring B is a trans-1,4-cyclohexylene, 1,4-phenylene or pyrimidine-2,5-diyl group, the ring C is a trans-1,4-cyclohexylene or 1,4-phenylene group, $Z_3$ is —$(CH_2)_2$—, —COO— or a covalent bond, $L_5$ and $L_6$ are independently H or F, and b and c are independently 0 or 1,

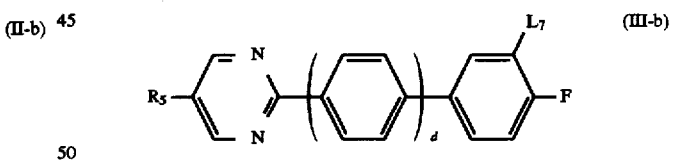

(III-b)

wherein $R_5$ is an alkyl group of 1–10 carbons, $L_7$ is H or F and d is 0 or 1,

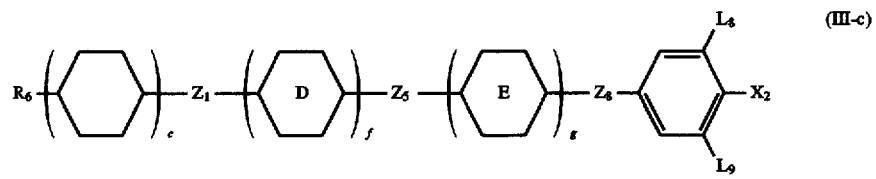

(III-c)

wherein $R_6$ is an alkyl group of 1–10 carbons, the rings D and E are independently a trans-1,4-cyclohexylene or 1,4-phenylene group, $Z_4$ and $Z_5$ are independently —COO— or a covalent bond, $Z_6$ is —COO— or —C≡C—, $L_8$ and $L_9$ are independently H or F, $X_2$ is F, $OCF_3$, $OCF_2H$, $CF_3$, $CF_2H$ or $CFH_2$, provided that when $X_2$ is $OCF_3$, $OCF_2H$, $CF_3$, $CF_2H$ or $CFH_2$, both $L_8$ and $L_9$ represent a hydrogen atom, and e, f and g are independently 0 or 1,

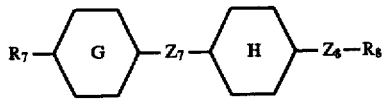
(III-d)

wherein $R_7$ and $R_8$ are independently an alkyl group of 1–10 carbons or an alkenyl group of 2–10 carbons, the methylene group (—CH$_2$—) in said alkyl or alkenyl group may be replaced by an oxygen atom (—O—) provided that two or more methylene groups in series are not replaced by an oxygen atom, the ring G is a trans-1,4-cyclohexylene, 1,4-phenylene or pyrimidine-2,5-diyl group, the ring H is a trans-1,4-cyclohexylene or 1,4-phenylene group, $Z_7$ is —C≡C—, —COO—, —(CH$_2$)$_2$—, —CH=CH—C≡C— or a covalent bond, and $Z_8$ is —COO or a covalent bond,

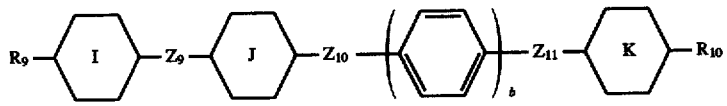
(III-e)

wherein $R_9$ and $R_{10}$ are independently an alkyl group of 1–10 carbons or an alkenyl group of 2–10 carbons, the methylene group (—CH$_2$—) in said alkyl or alkenyl group may be replaced by an oxygen atom (—O—) provided that two or more methylene groups in series are not replaced by an oxygen atom, the ring I is a trans-1,4-cyclohexylene, 1,4-phenylene or pyrimidine-2,5-diyl group, the ring J is a trans-1,4-cyclohexylene group, a 1,4-phenylene or pyrimidine-2,5-diyl group in which one or more hydrogen atoms on the ring may be substituted by F, the ring K is a trans-1,4-cyclohexylene or 1,4-phenylene group, $Z_9$ and $Z_{11}$ are independently —COO—, —(CH$_2$)$_2$—, or a covalent bond, $Z_{10}$ is —CH=CH—, —C≡C—, —COO— or a covalent bond and h is 0 or 1.

In addition, the present invention provides a liquid crystal composition which comprises:

(i) as a first component, at least one of the liquid crystalline compounds of formula (I), (ii) as a part of a second component, at least one compound selected from the group consisting of the compounds of formulae (II-a), (II-b) and (II-c), and (iii) as another part of a second component, at least one compound selected from the group consisting of the compounds of formulae (III-a), (III-b), (III-c), (III-d) and (III-e).

According to further aspects of the present invention, there is provided a liquid crystal display element using any one of the liquid crystal compositions as described above.

The liquid crystalline compounds of formula (I) of the invention are characterized by a tricyclic derivative having an alkenyl group in its molecule. Those liquid crystalline compounds are exceedingly, physically and chemically stable under the condition in which a display element is used, and have a high NI point which enables the working limit of high temperature to increase. Further, it should be noted that the liquid crystalline compounds of the present invention are also characterized by a higher elastic constant ratio $K_{33}/K_{11}$, a lower viscosity and a good solubility in a liquid crystal composition at a lower temperature. The desired physical properties of the compounds can be controlled by a suitable choice of the structure of a substituent or a side chain from the molecular constituion elements. Thus, the compounds of the present invention can be used as a component of a liquid crystal composition to provide a new liquid crystal composition having good characteristics.

Of the compounds of formula (I) preferable are those classified by the following formulae:

| | |
|---|---|
| $R_1$—Cyc—Cyc—Cyc—$R_{11}$—$R_2$ | (I-a) |
| $R_1$—Dio—Cyc—Cyc—$R_{11}$—$R_2$ | (I-b) |
| $R_1$—Cyc—Dio—Cyc—$R_{11}$—$R_2$ | (I-c) |
| $R_1$—Cyc—Cyc—Dio—$R_{11}$—$R_2$ | (I-d) |
| $R_1$—Thp—Cyc—Cyc—$R_{11}$—$R_2$ | (I-e) |
| $R_1$—Cyc—Thp—Cyc—$R_{11}$—$R_2$ | (I-f) |
| $R_1$—Cyc—Cyc—Thp—$R_{11}$—$R_2$ | (I-g) |
| $R_1$—Dit—Cyc—Cyc—$R_{11}$—$R_2$ | (I-h) |
| $R_1$—Cyc—Dit—Cyc—$R_{11}$—$R_2$ | (I-i) |
| $R_1$—Cyc—Cyc—Dit—$R_{11}$—$R_2$ | (I-j) |
| $R_1$—Tht—Cyc—Cyc—$R_{11}$—$R_2$ | (I-k) |
| $R_1$—Cyc—Tht—Cyc—$R_{11}$—$R_2$ | (I-l) |
| $R_1$—Cyc—Cyc—Tht—$R_{11}$—$R_2$ | (I-m) |
| $R_1$—Cyd—Cyc—Cyc—$R_{11}$—$R_2$ | (I-n) |
| $R_1$—Cyc—Cyd—Cyc—$R_{11}$—$R_2$ | (I-o) |
| $R_1$—Cyc—Cyc—Cyd—$R_{11}$—$R_2$ | (I-p) |

In the above formulae, $R_1$ and $R_2$ are as defined above, $R_{11}$ represents

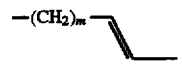

(m is 0 to 5), Cyc stands for a trans-1,4-cyclehexylene group, Dio stands for a 1,3-dioxane-2,5-diyl group, Thp stands for a tetrahydro-pyrane-2,5-diyl group, Dit stands for a 1,3-dithian-2,5-diyl group, Tht stands for a tetrahydrothiopyrane-2,5-diyl group, Cyd stands for a cyclohexene-1,4-diyl group.

In formula (I), $A_1$, $A_2$ and $A_3$ are preferably selected from the group consisting of Cyc, Dio, Thp, Dit, Tht, and Cyd, but those not containing two or more of Dio, Thp, Dit and Tht in the molecule are preferable as shown by the above formulae of (I-a) to (I-p).

Examples of $R_1$ in formula (I) can include alkyl of 1–15 carbons; alkenyl of 2–15 carbons such as 1-alkenyl of 2–15 carbons, 2-alkenyl of 3–15 carbons and 3-alkenyl of 4–15 carbons; alkoxy or alkylthio of 1–14 carbons; alkoxyalkyl or alkylthioalkyl of 1–14 carbons such as alkoxymethyl, 2-alkoxyethyl, alkylthiomethyl and 2-alkylthioethyl; alkoxyalkoxy, alkylthioalkylthio, alkylthioalkoxy or alkoxyalkylthio of 1–13 carbons such as alkoxymethoxy, 2-alkoxyethoxy, alkylthiomethylthio, 2-alkylthioethylthio, alkylthiomethoxy, 2-alkylthioethoxy, alkoxymethylthio, and 2-alkoxyethylthio; alkenyloxy of 2–14 carbons such as 2-alkenyloxy of 3–14 carbons and 3-alkenyloxy of 4–14 carbons; alkynyl of 2–16 carbons such as 1-alkynyl of 2–16 carbons, 2-alkynyl of 3–16 carbons and 3-alkynyl of 4–16 carbons; and alkanoyloxy or alkanoyloxyalkyl of 2–15 carbons such as alkanoyloxymethyl and 2-alkanoyloxyethyl. Of these groups, alkyl of 1–15 carbons, alkenyl of 2–15 carbons, alkoxy of 1–14 carbons and alkenyloxy of 2–14 carbons are preferable. Particularly preferable are methyl, ethyl, n-propyl, n-butyl, n-pentyl, n-hexyl, n-heptyl, n-octyl, n-nonyl, vinyl, 3-butenyl, trans-3-pentenyl, 2-propenyl and trans-2-butenyl.

Examples of $R_2$ can include hydrogen, methyl, ethyl, n-propyl, n-butyl, n-pentyl, n-hexyl, n-heptyl, n-octyl, n-nonyl and n-decyl.

In all compounds as listed above, "—$R_{11}$—$R_2$" represents an alkenyl group of 2–15 carbons. Preferable are the compounds wherein any one methylene group (—$CH_2$—) in $R_{11}$ (when m is 2 or more) is replaced by —O—. Of those compounds, particularly preferable groups include ethenyl, 1-propenyl, 1-butenyl, 3-butenyl, 1-oxy-3-butenyl, 1-pentenyl, 3-pentenyl and 1-oxy-3-pentenyl.

Preferred examples of —$(CH_2)_m$— in $R_{11}$ replaced by —O— can include —O—$CH_2$—, —O—$C_2H_4$—, —O—$C_3H_6$—, —$CH_2$—O—$C_2H_4$—, —$C_2H_4$—O—$CH_2$— and —$CH_2$—O—$CH_2$—.

Of the above-mentioned compounds, those of formulae (I-a), (I-b), (I-c), (I-d), (I-f) and (I-g) are suitable for achieving the object of this invention, examples of which can include those of the following formulae (I-1) to (I-19):

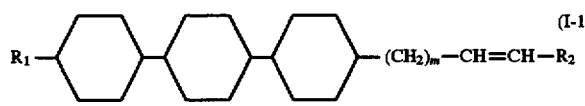
(I-1)

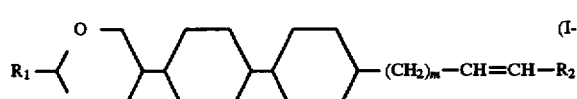
(I-2)

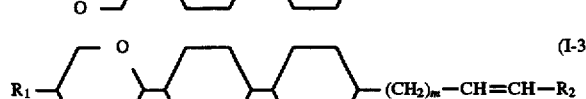
(I-3)

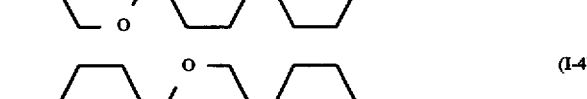
(I-4)

(I-5)

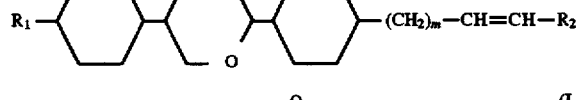
(I-6)

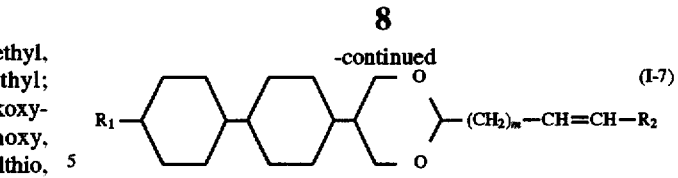
(I-7)

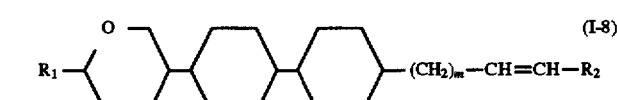
(I-8)

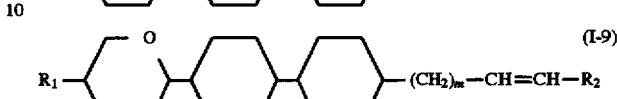
(I-9)

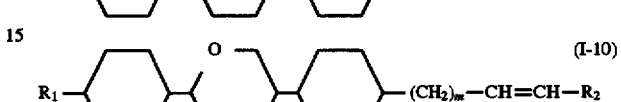
(I-10)

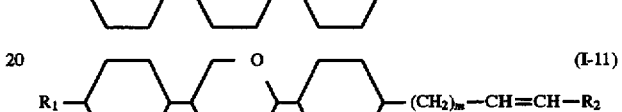
(I-11)

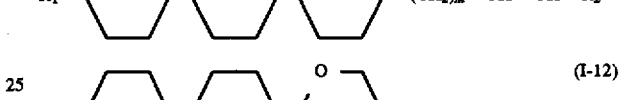
(I-12)

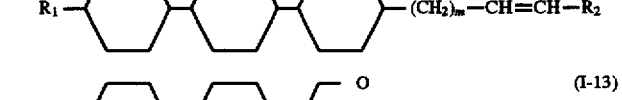
(I-13)

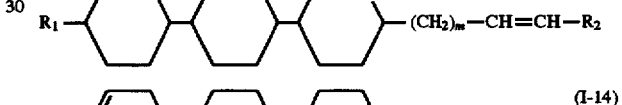
(I-14)

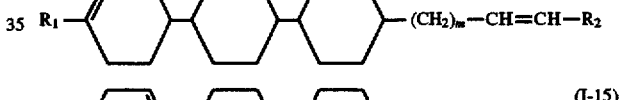
(I-15)

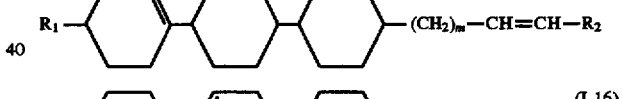
(I-16)

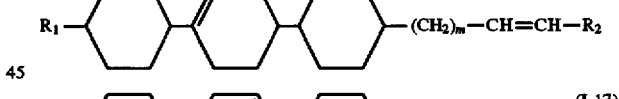
(I-17)

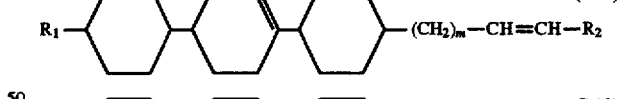
(I-18)

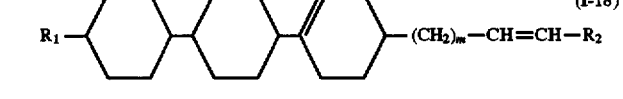
(I-19)

It is preferable that the liquid crystal composition of the invention contains one or more compounds of formula (I) in a proportion of 0.1–99.9% by weight to exhibit excellent characteristics.

More specifically, the liquid crystal composition of the invention is prepared by mixing a first component containing at least one of the compounds of formula (I) with any compound selected from other compounds of formula (I) or the compounds of formulae (II-a) to (II-c) and (III-a) to (III-e) in compliance with the object of the liquid crystal composition.

The liquid crystal composition of the invention may comprise a first component containing at least one of the liquid crystalline compounds of formula (I), but it is preferable that in addition to the first component, the liquid crystal composition comprises as a second component at least one compound selected from the group consisting of the compounds of formulae (II-a), (II-b) and (II-c) (hereinafter called "a second A component") and/or at least one compound selected from the group consisting of the compounds of formulae (III-a), (III-b), (III-c), (III-d) and (III-e) (hereinafter called "a second b component"). Further, known compounds can be mixed as a third component in order to control the threshold voltage, temperature range for a liquid crystal phase, optical anisotropy, dielectric anisotropy, viscosity and others of the liquid crystal composition.

Of the above-mentioned second A components, suitable examples of the compounds of formulae (II-a), (II-b) and (II-c) can include the following compounds of formulae (II-a-1) to (II-a-15), (II-b-1) to (II-b-48) and (II-c-1) to (II-c-55).

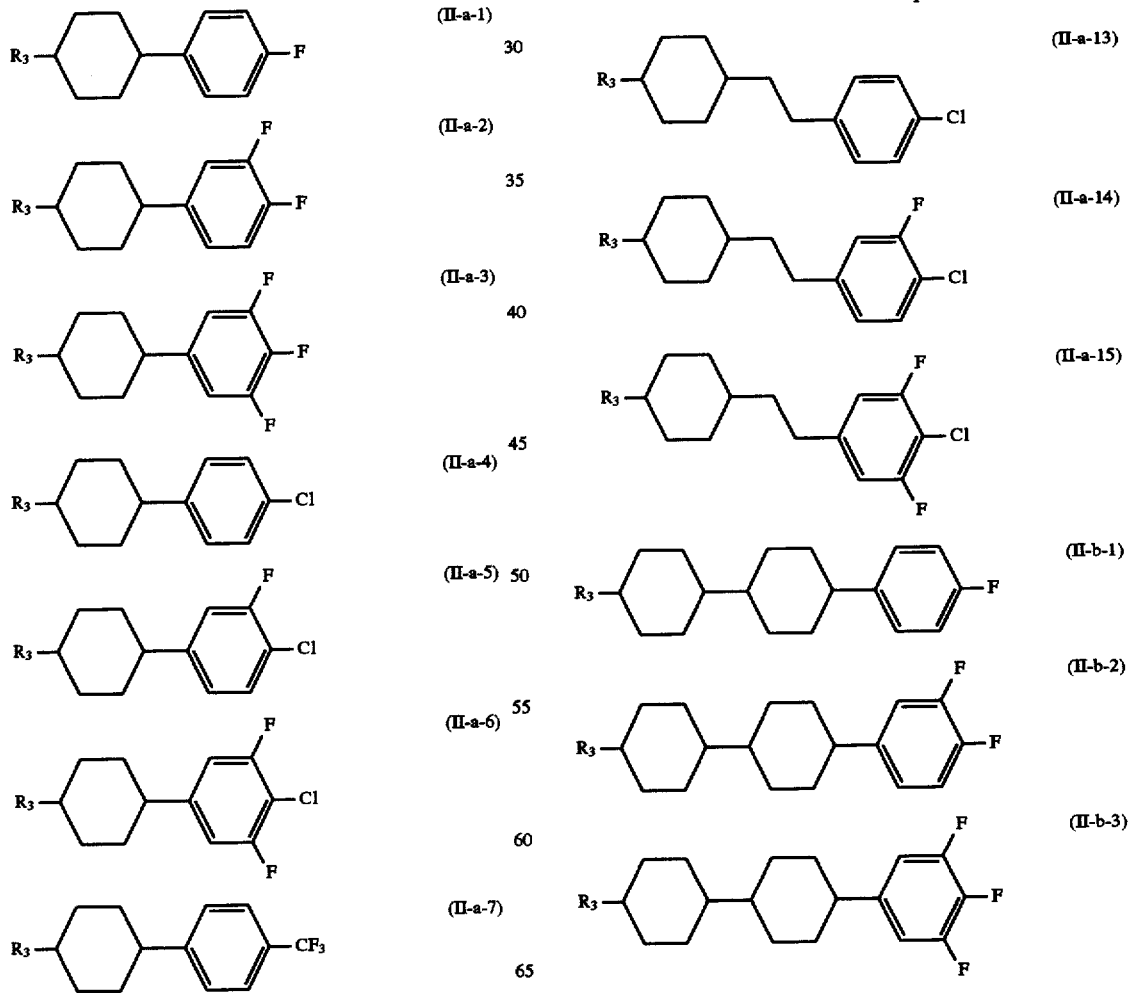

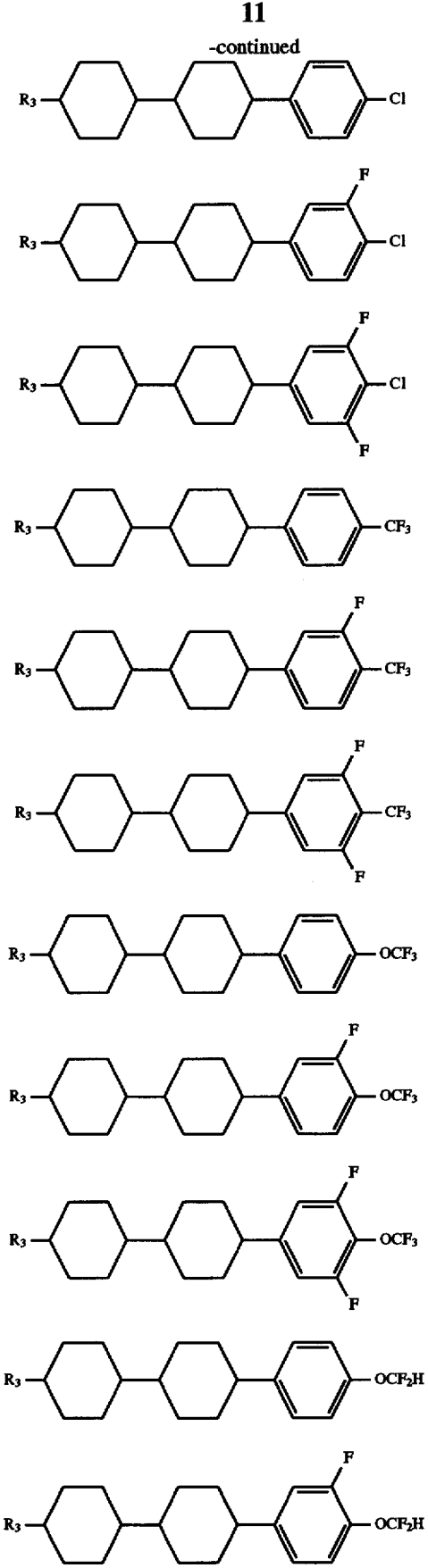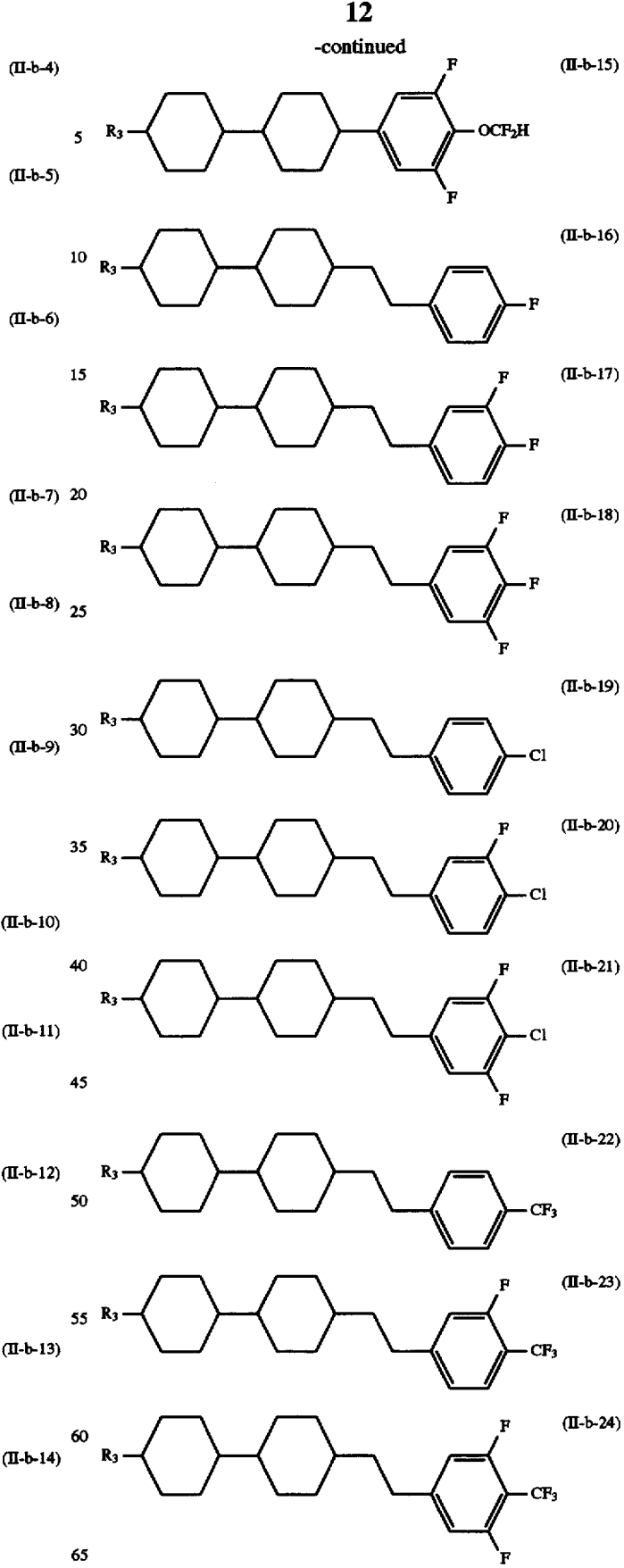

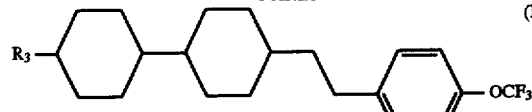 (II-b-25)
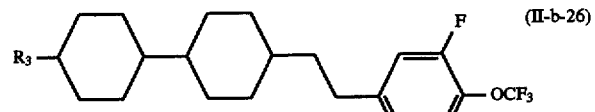 (II-b-26)
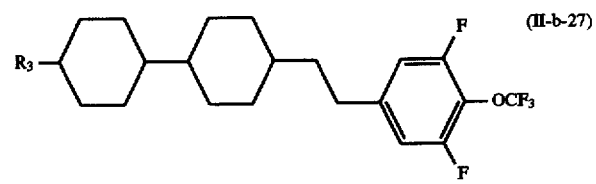 (II-b-27)
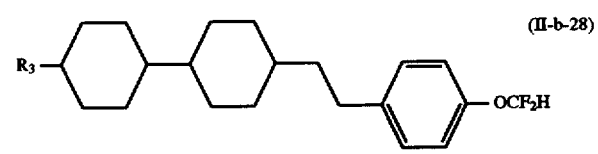 (II-b-28)
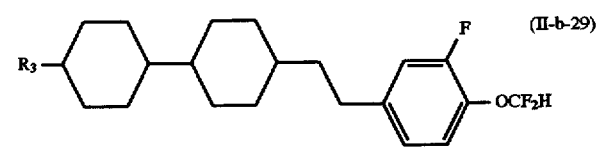 (II-b-29)
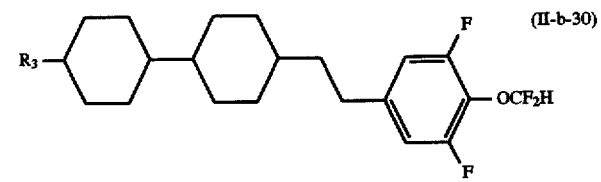 (II-b-30)
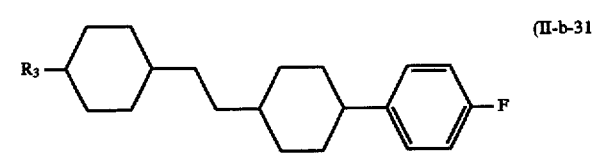 (II-b-31)
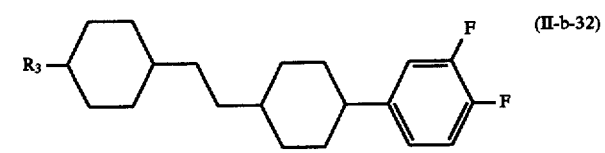 (II-b-32)
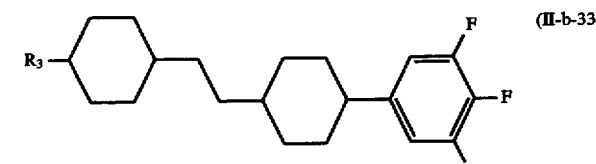 (II-b-33)
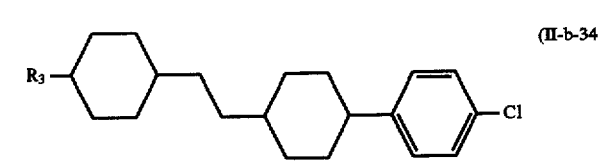 (II-b-34)
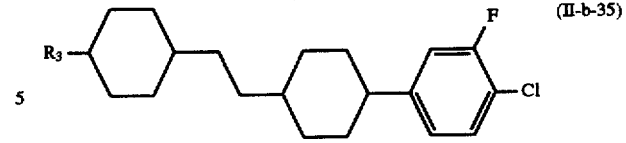 (II-b-35)
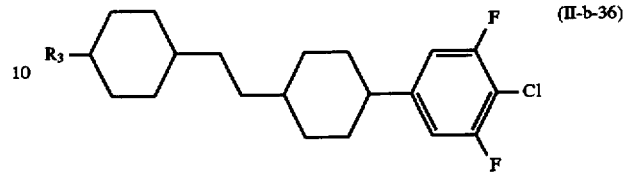 (II-b-36)
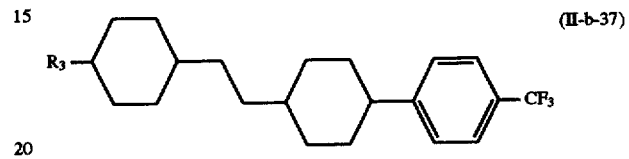 (II-b-37)
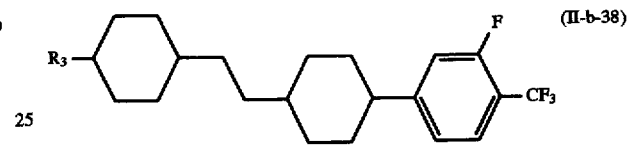 (II-b-38)
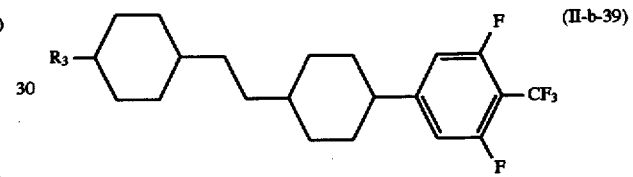 (II-b-39)
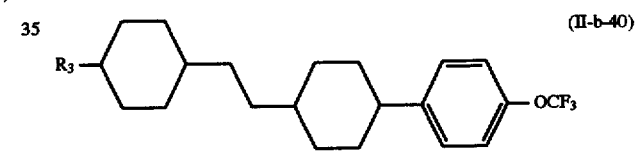 (II-b-40)
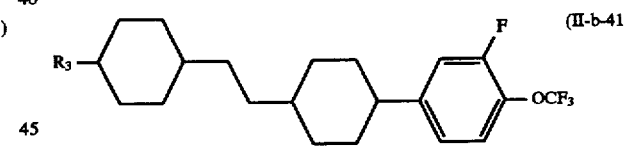 (II-b-41)
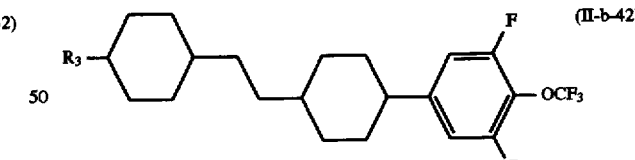 (II-b-42)
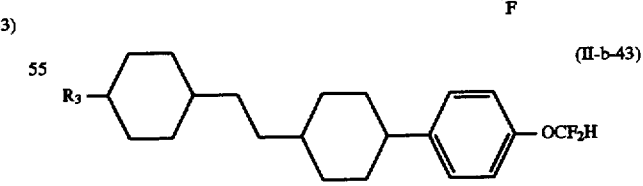 (II-b-43)
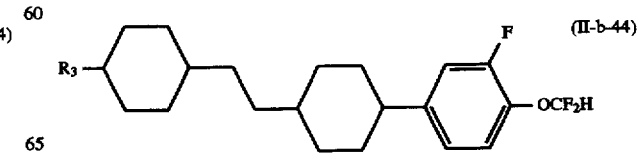 (II-b-44)

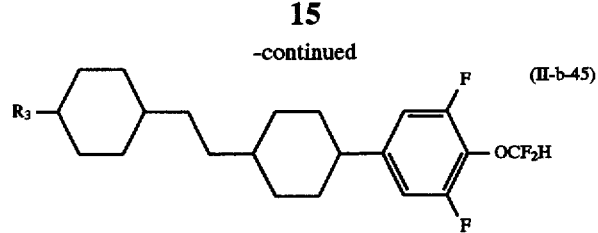 (II-b-45)
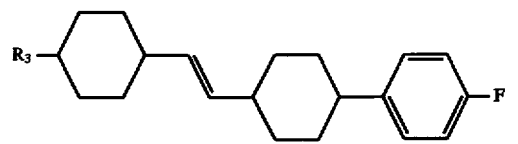 (II-b-46)
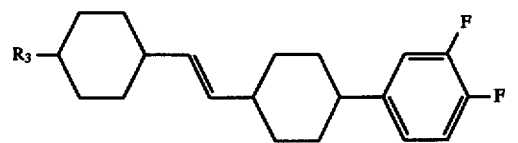 (II-b-47)
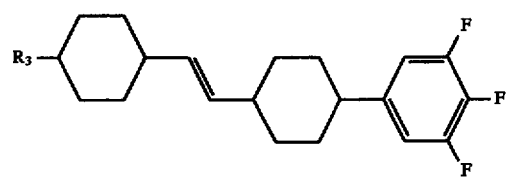 (II-b-48)
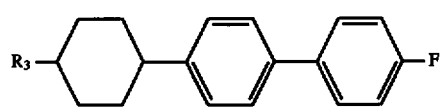 (II-c-1)
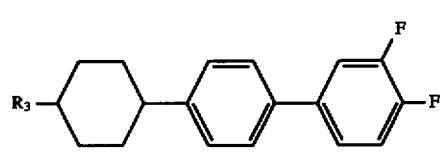 (II-c-2)
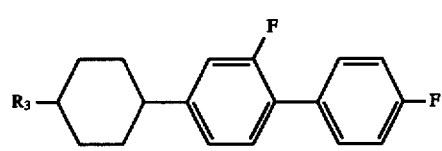 (II-c-3)
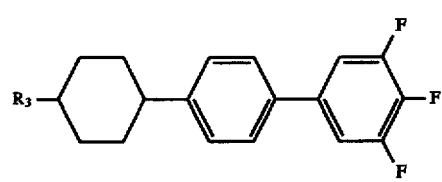 (II-c-4)
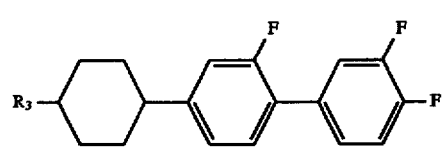 (II-c-5)
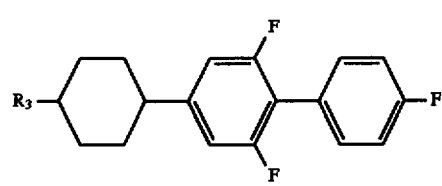 (II-c-6)
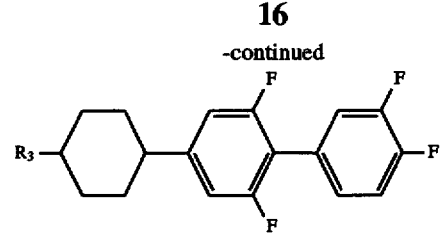 (II-c-7)
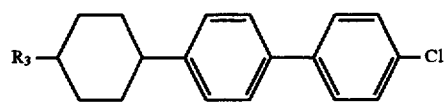 (II-c-8)
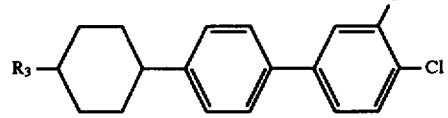 (II-c-9)
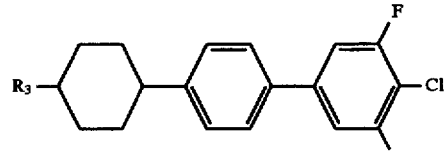 (II-c-10)
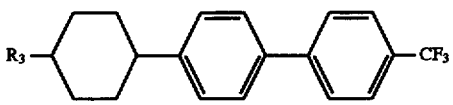 (II-c-11)
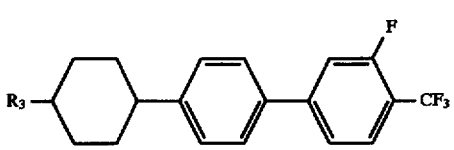 (II-c-12)
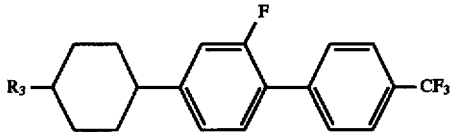 (II-c-13)
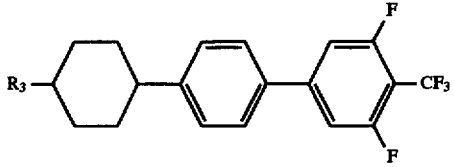 (II-c-14)
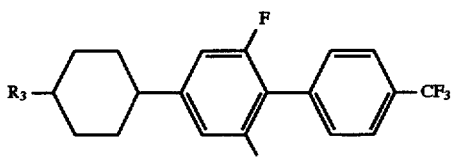 (II-c-15)
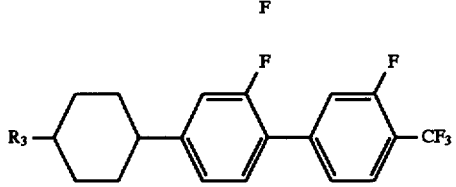 (II-c-16)

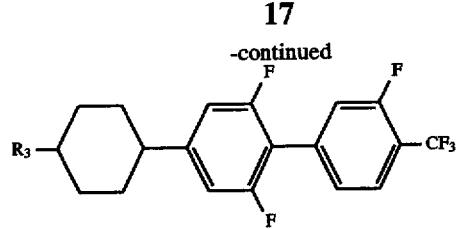 (II-c-17)
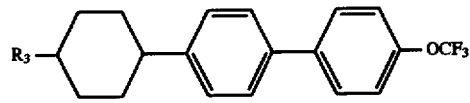 (II-c-18)
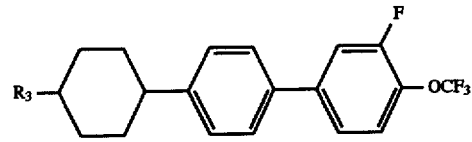 (II-c-19)
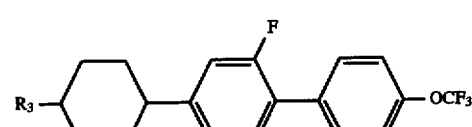 (II-c-20)
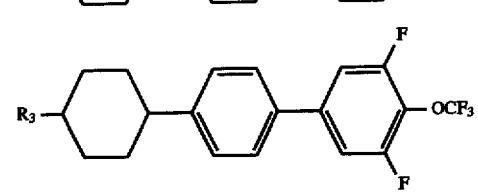 (II-c-21)
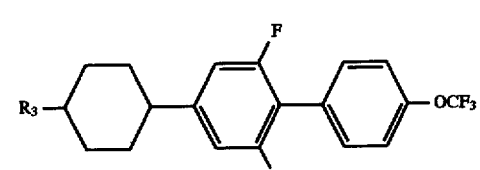 (II-c-22)
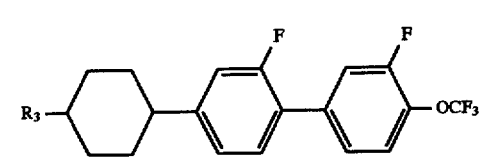 (II-c-23)
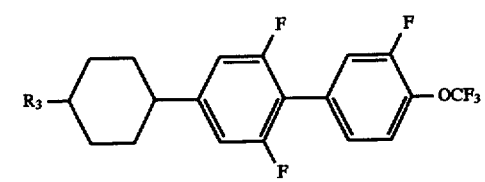 (II-c-24)
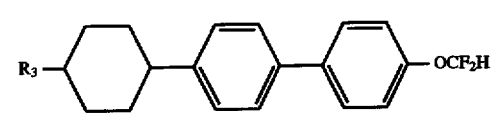 (II-c-25)
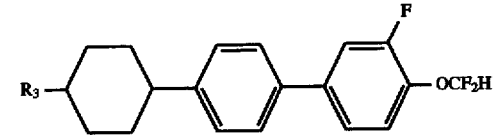 (II-c-26)
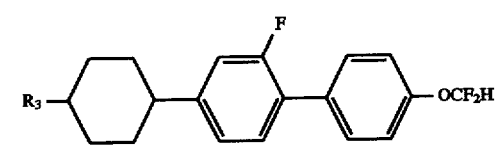 (II-c-27)
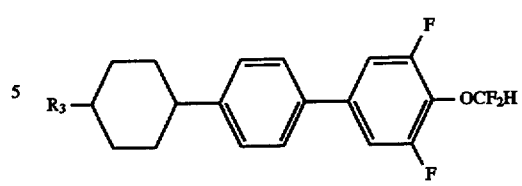 (II-c-28)
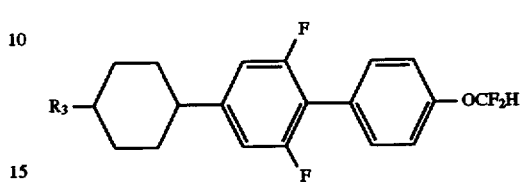 (II-c-29)
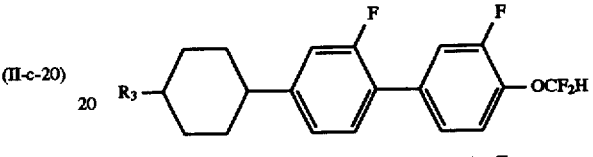 (II-c-30)
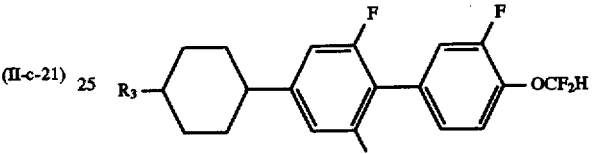 (II-c-31)
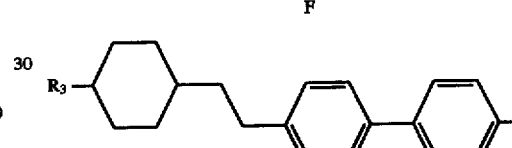 (II-c-32)
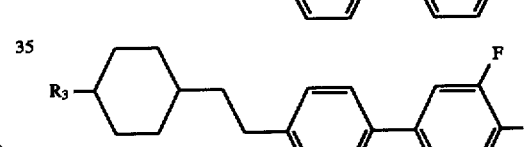 (II-c-33)
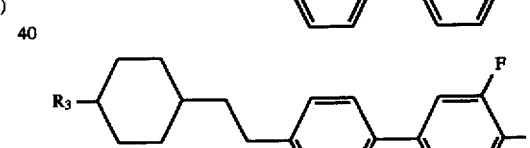 (II-c-34)
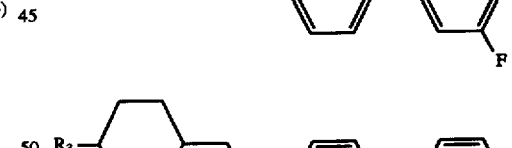 (II-c-35)
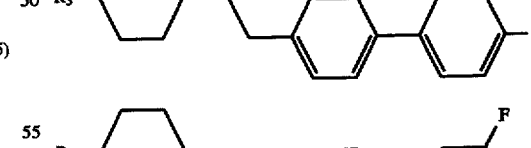 (II-c-36)
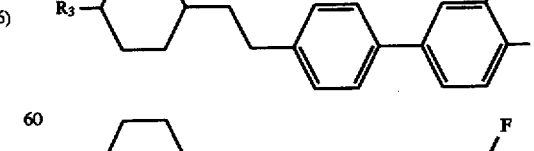 (II-c-37)

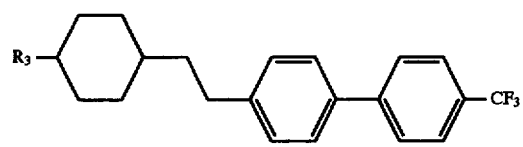 (II-c-38)

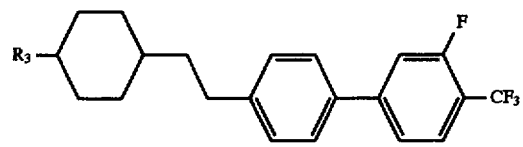 (II-c-39)

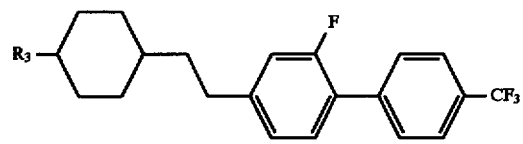 (II-c-40)

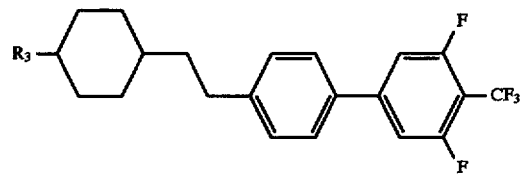 (II-c-41)

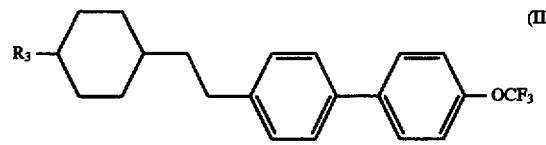 (II-c-42)

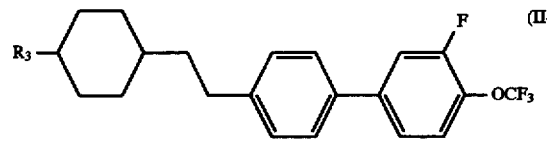 (II-c-43)

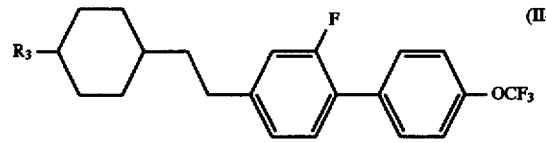 (II-c-44)

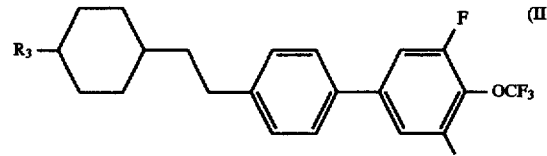 (II-c-45)

 (II-c-46)

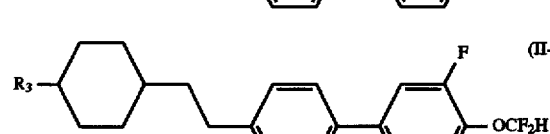 (II-c-47)

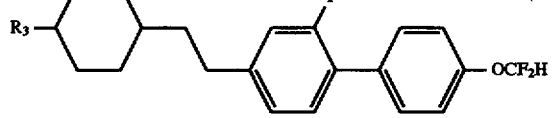 (II-c-48)

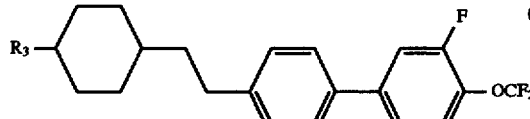 (II-c-49)

 (II-c-50)

 (II-c-51)

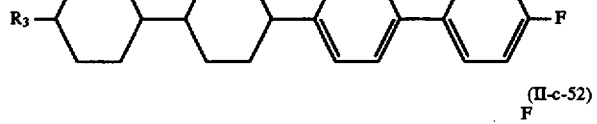 (II-c-52)

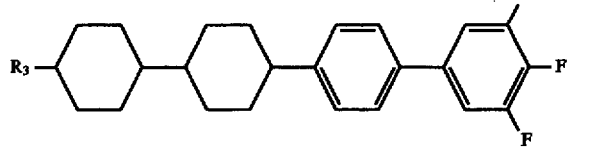 (II-c-53)

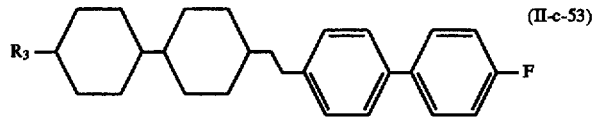 (II-c-54)

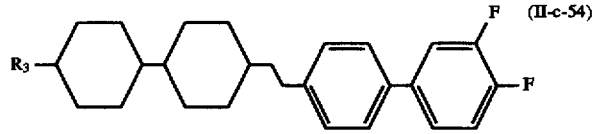 (II-c-55)

In the above formulae, $R_3$ is as defined above.

The compounds of formulae (II-a) to (II-c) show a positive dielectric anisotropy and have very excellent heat stability and chemical stability.

An amount of said compound used is suitably in the range of 1–99% by weight, preferably 10–97% by weight, more preferably 40–95% by weight, based on a total weight of the liquid crystal composition.

Of the above-mentioned second B components, suitable examples of the compounds of formulae (III-a), (III-b) and (III-c) can include the following compounds of formulae (III-a-1) to (III-a-24), (III-b-1) to (III-b-3) and (III-c-1) to (III-c-17).

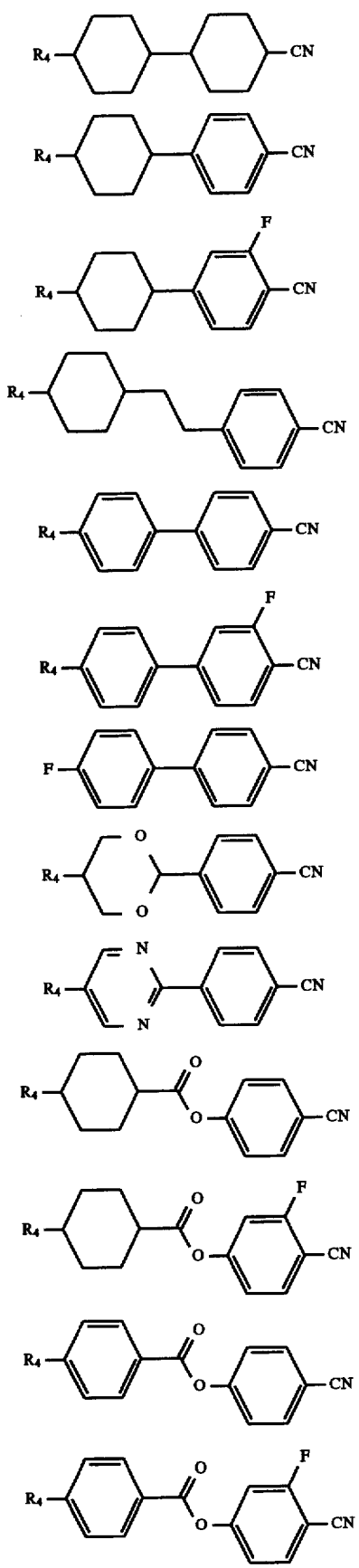
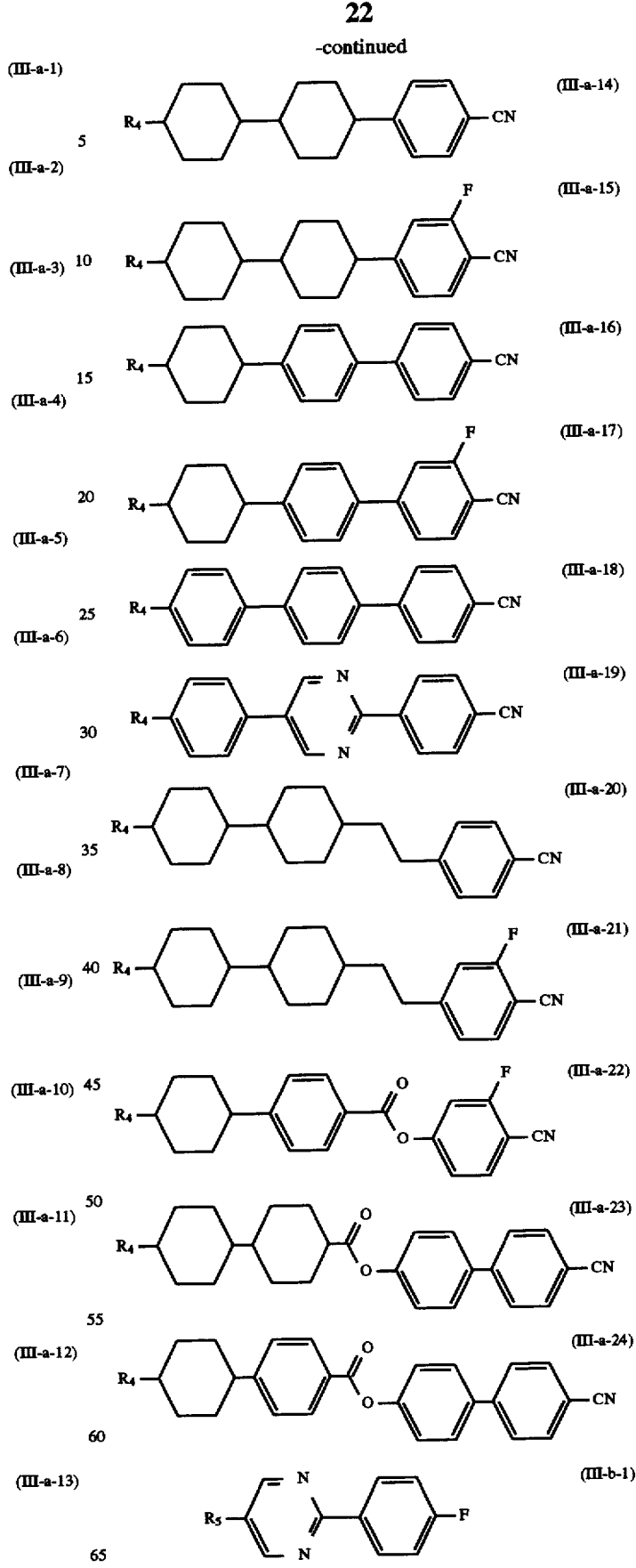

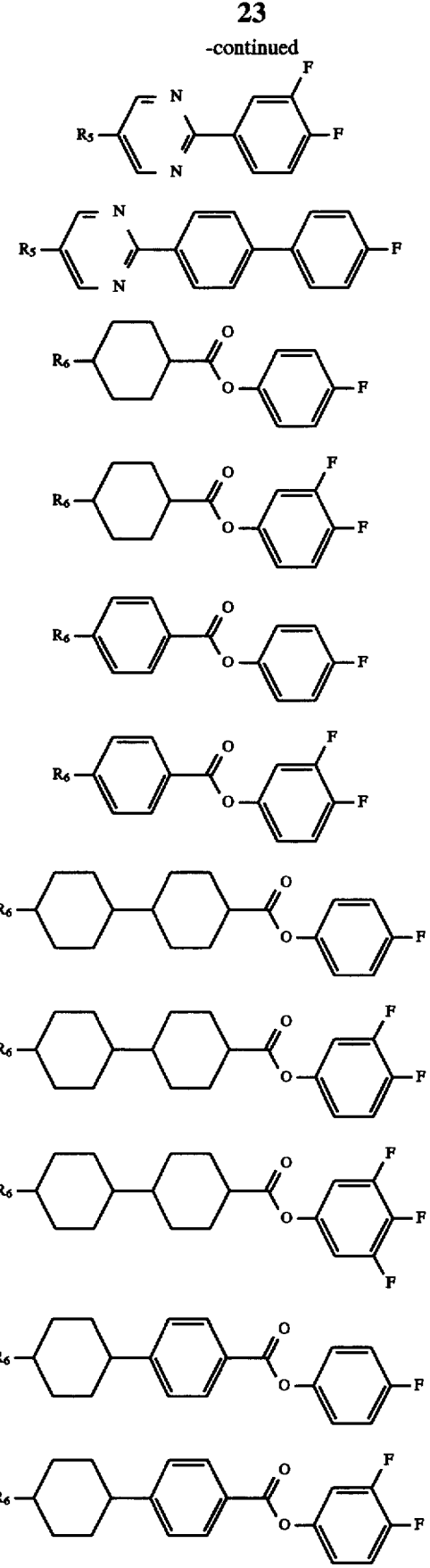

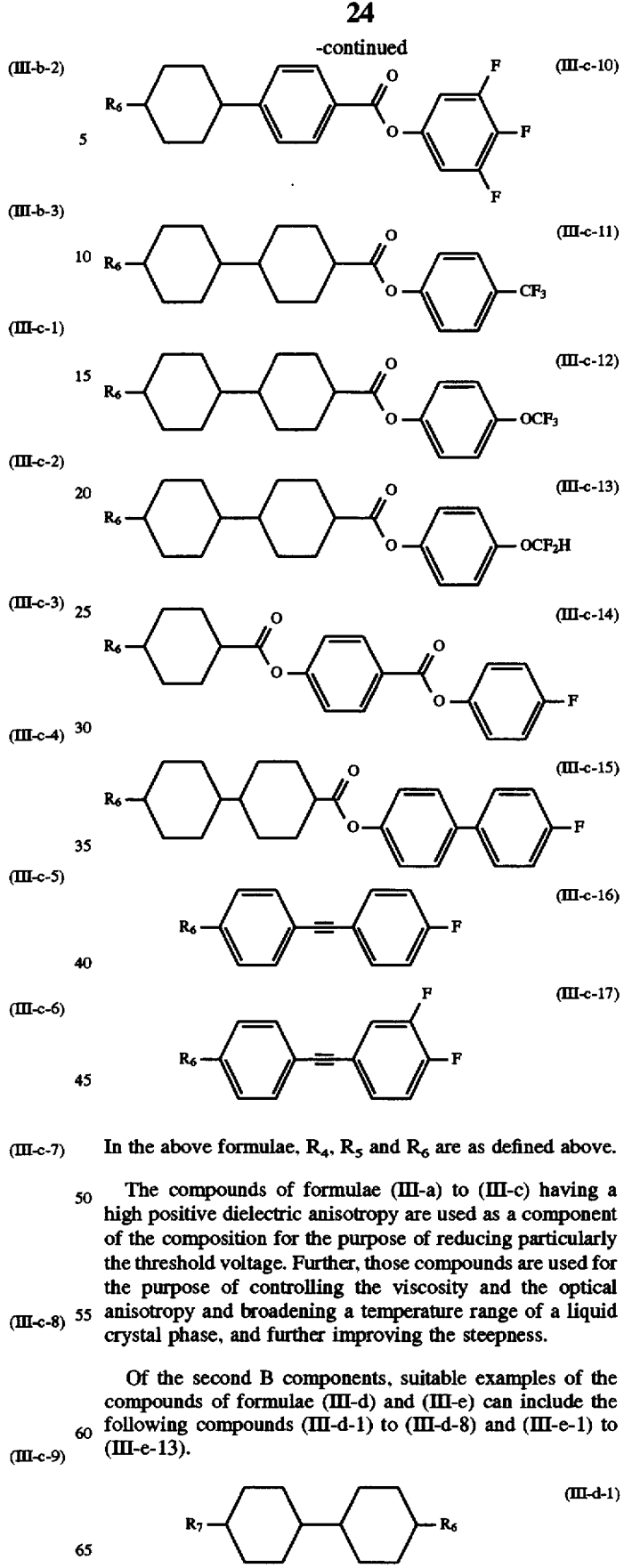

In the above formulae, $R_4$, $R_5$ and $R_6$ are as defined above.

The compounds of formulae (III-a) to (III-c) having a high positive dielectric anisotropy are used as a component of the composition for the purpose of reducing particularly the threshold voltage. Further, those compounds are used for the purpose of controlling the viscosity and the optical anisotropy and broadening a temperature range of a liquid crystal phase, and further improving the steepness.

Of the second B components, suitable examples of the compounds of formulae (III-d) and (III-e) can include the following compounds (III-d-1) to (III-d-8) and (III-e-1) to (III-e-13).

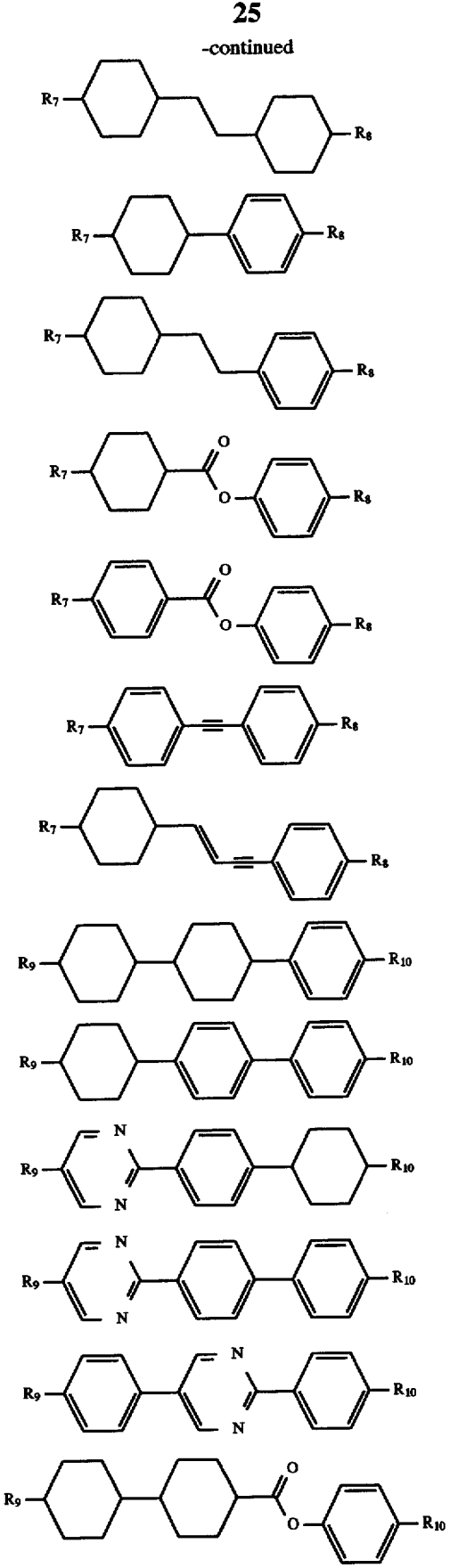

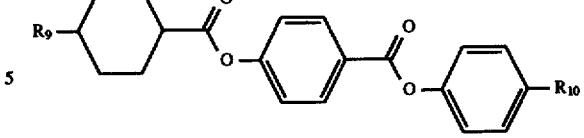
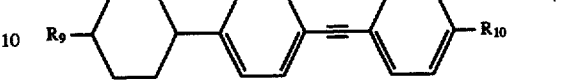
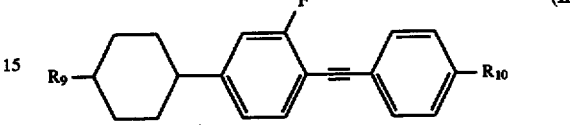
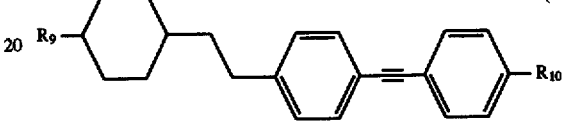
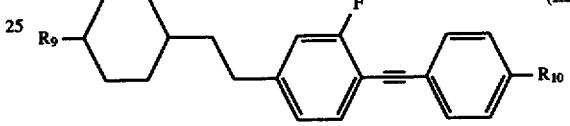
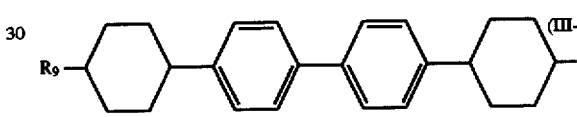
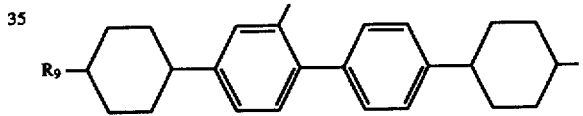
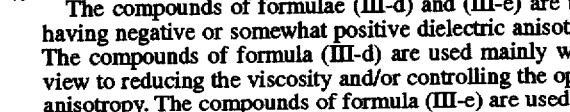
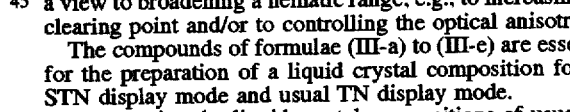
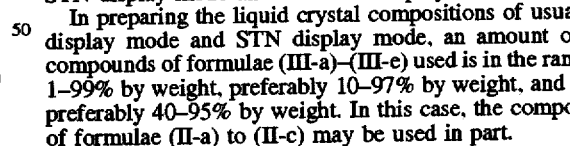
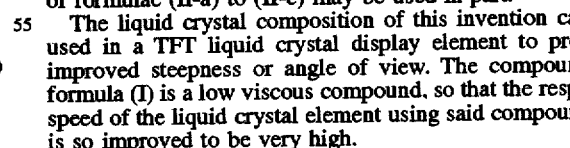
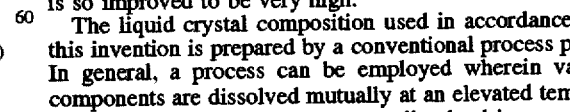
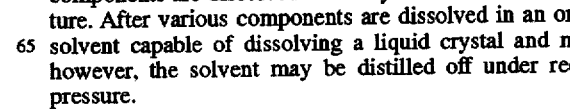

In the above formulae, $R_7$ and $R_8$ are as defined above.

The compounds of formulae (III-d) and (III-e) are those having negative or somewhat positive dielectric anisotropy. The compounds of formula (III-d) are used mainly with a view to reducing the viscosity and/or controlling the optical anisotropy. The compounds of formula (III-e) are used with a view to broadening a nematic range, e.g., to increasing the clearing point and/or to controlling the optical anisotropy.

The compounds of formulae (III-a) to (III-e) are essential for the preparation of a liquid crystal composition for the STN display mode and usual TN display mode.

In preparing the liquid crystal compositions of usual TN display mode and STN display mode, an amount of the compounds of formulae (III-a)–(III-e) used is in the range of 1–99% by weight, preferably 10–97% by weight, and more preferably 40–95% by weight. In this case, the compounds of formulae (II-a) to (II-c) may be used in part.

The liquid crystal composition of this invention can be used in a TFT liquid crystal display element to provide improved steepness or angle of view. The compound of formula (I) is a low viscous compound, so that the response speed of the liquid crystal element using said compound (I) is so improved to be very high.

The liquid crystal composition used in accordance with this invention is prepared by a conventional process per se. In general, a process can be employed wherein various components are dissolved mutually at an elevated temperature. After various components are dissolved in an organic solvent capable of dissolving a liquid crystal and mixed, however, the solvent may be distilled off under reduced pressure.

The liquid crystal compounds of this invention are improved and optimized with any suitable additives, depending on the intended applications. Such additives are well known to those skilled in the art and also disclosed in literatures.

The present liquid crystal compounds can be used as a liquid crystal composition for guest-host (GH) mode by incorporating therein dichroic dyes such as merocyanine type, styryl type, azo type, azomethine type, azoxy type, quinophthalone type, anthraquinone type, tetrazine type and the like. The liquid crystal composition of this invention can be further used for NPCA prepared by micro-capsulating nematic liquid crystals or polymer-dispersion type liquid crystal display elements (PDLCD) represented by polymer network liquid crystal display elements (PNLCD) in which three-dimensional network polymer is formed in the liquid crystal. In addition, the present liquid crystal compounds can be used as a liquid crystal composition for electrically controlled birefringence (ECB) mode or dynamic scattering (DS) mode.

The nematic liquid crystal compositions comprising the compounds of the present invention can be illustrated by the following composition examples.

Composition Example 1

| Structure | Amount |
|---|---|
| $C_3H_7$—⬡—⬡—⬡—CH=CH$_2$ | 8 wt % |
| $C_2H_5$—⬡—⬡—⬡—(CH$_2$)$_2$—CH=CH$_2$ | 7 wt % |
| $C_3H_7$—⬡—⌬—CN | 14 wt % |
| $C_5H_{11}$—⬡—⌬—CN | 8 wt % |
| $C_2H_5$—⌬—⌬—CN | 5 wt % |
| $C_2H_5$—⌬—C≡C—⌬—OCH$_3$ | 3 wt % |
| $C_2H_5$—⌬—C≡C—⌬—CH$_3$ | 5 wt % |
| $CH_3$—⌬—C≡C—⌬—$C_6H_{13}$ | 10 wt % |
| $C_4H_9$—⌬—C≡C—⌬—$C_4H_9$ | 5 wt % |
| $C_3H_7$—⬡—⬡—$C_4H_9$ | 10 wt % |
| $C_2H_5$—⬡—⬡—⌬—CN | 4 wt % |
| $C_3H_7$—⬡—⬡—⌬—CN | 4 wt % |

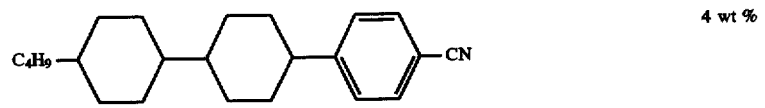 4 wt %
 5 wt %
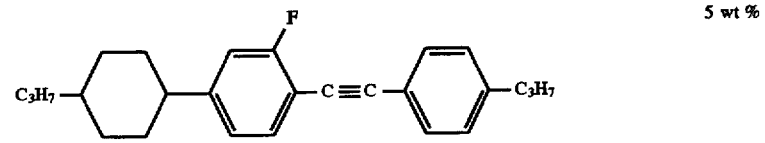 5 wt %
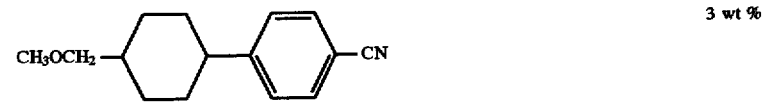 3 wt %
Composition Example 2
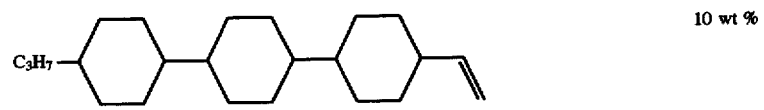 10 wt %
 8 wt %
 10 wt %
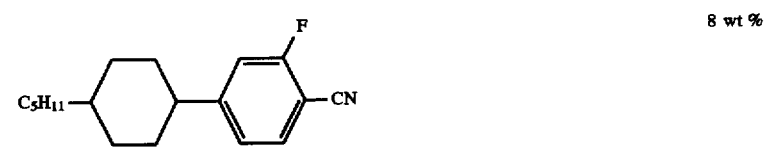 8 wt %
 5 wt %
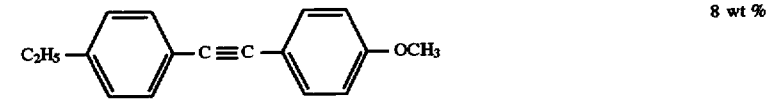 8 wt %
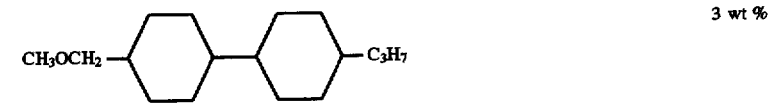 3 wt %
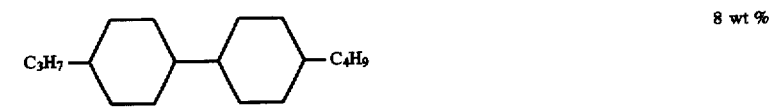 8 wt %
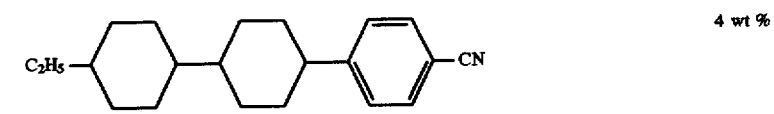 4 wt %

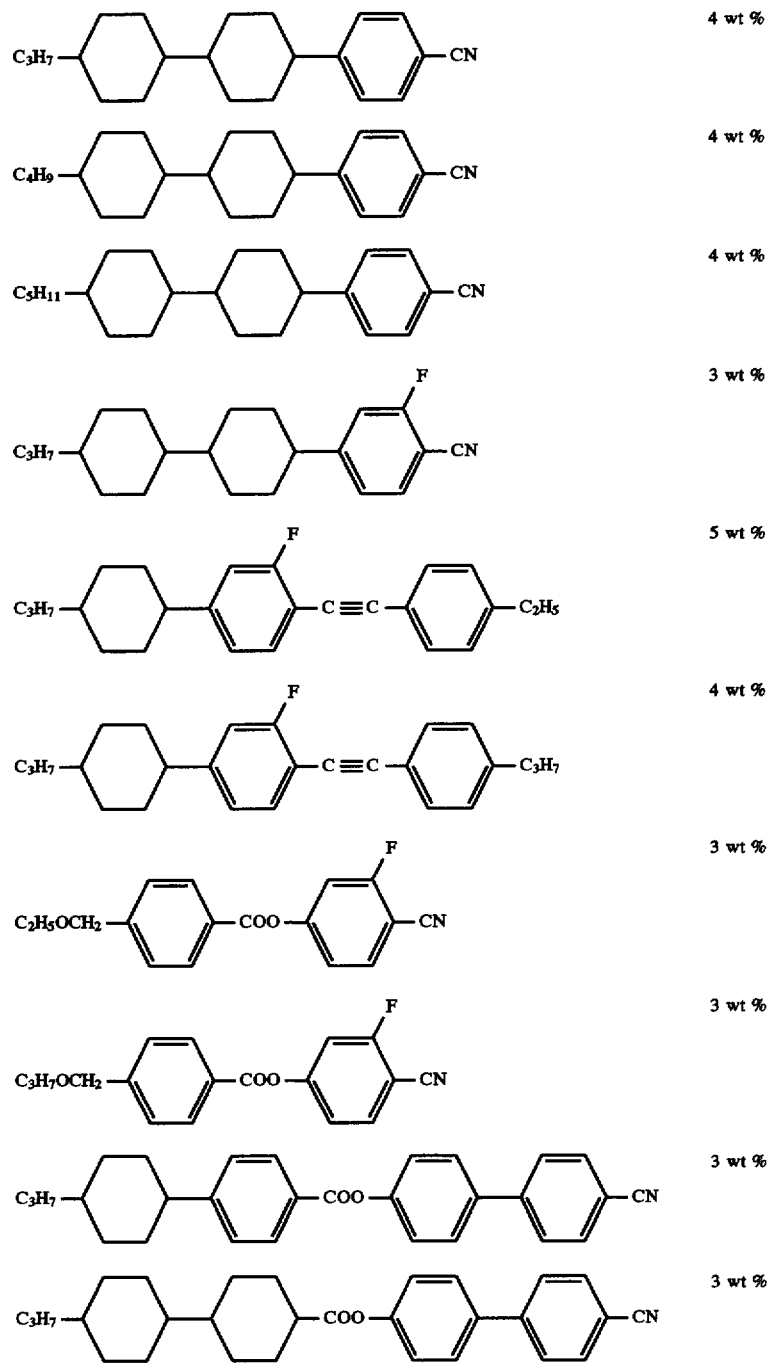
4 wt %
4 wt %
4 wt %
3 wt %
5 wt %
4 wt %
3 wt %
3 wt %
3 wt %
3 wt %
Composition Example 3
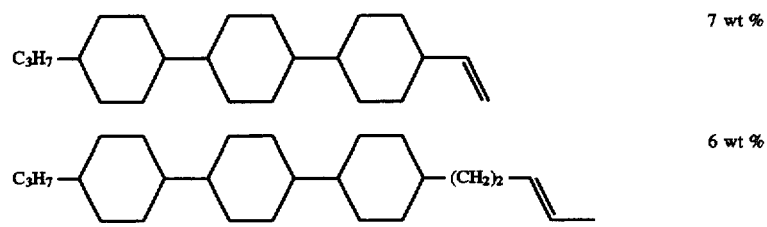
7 wt %
6 wt %

| Structure | wt % |
|---|---|
| C₃H₇–(pyrimidine)–C₆H₃(3,4-F₂) | 9 wt % |
| C₃H₇–Cy–Ph–CN | 10 wt % |
| CH₂=CHC₂H₄–Cy–Ph–CN | 10 wt % |
| CH₃CH=CHC₂H₄–Cy–Ph–CN | 10 wt % |
| C₃H₇–(pyrimidine)–Ph–Ph–F | 7 wt % |
| C₄H₉–(pyrimidine)–Ph–Ph–F | 7 wt % |
| C₅H₁₁–(pyrimidine)–Ph–Ph–F | 7 wt % |
| C₃H₇–Cy–(CH₂)₂–Ph–C≡C–Ph–C₂H₅ | 3 wt % |
| C₃H₇–Cy–(CH₂)₂–Ph–C≡C–Ph–C₃H₇ | 3 wt % |
| C₃H₇–Cy–(CH₂)₂–Ph–C≡C–Ph–C₄H₉ | 3 wt % |
| C₂H₅–(pyrimidine)–Ph–Cy–C₂H₅ | 3 wt % |
| C₃H₇–(pyrimidine)–Ph–Cy–C₂H₅ | 3 wt % |
| C₂H₅–(pyrimidine)–Ph–Cy–C₃H₇ | 3 wt % |
| C₃H₇–(pyrimidine)–Ph–Cy–C₃H₇ | 3 wt % |

-continued
 3 wt %
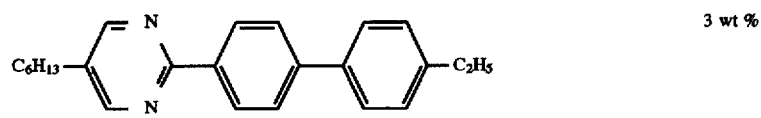 3 wt %
Composition Example 4
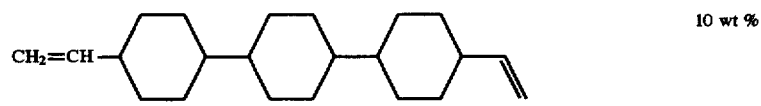 10 wt %
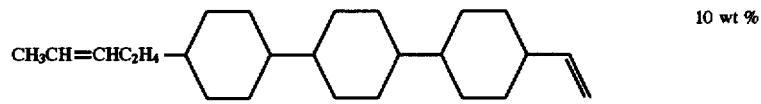 10 wt %
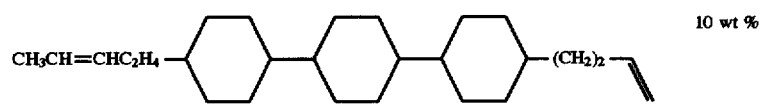 10 wt %
 6 wt %
 4 wt %
 4 wt %
 5 wt %
 4 wt %
 3 wt %
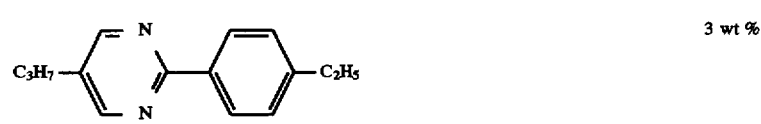 3 wt %
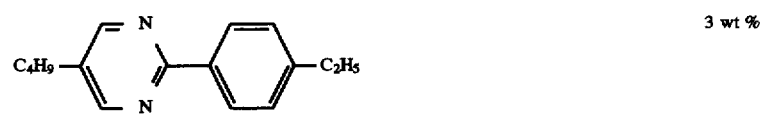 3 wt %
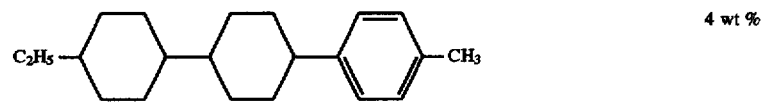 4 wt %

| Structure | Amount |
|---|---|
| C₃H₇–⟨Cy⟩–⟨Cy⟩–⟨Ph⟩–CH₃ | 5 wt % |
| C₃H₇–⟨Cy⟩–⟨Cy⟩–⟨Ph⟩–OCH₃ | 3 wt % |
| C₃H₇–⟨Cy⟩–⟨Cy⟩–⟨Ph⟩–C₃H₇ | 10 wt % |
| C₃H₇–⟨Cy⟩–⟨Cy⟩–⟨Ph⟩–CN | 4 wt % |
| C₃H₇–⟨Cy⟩–⟨Ph⟩–COO–⟨Ph⟩–F | 4 wt % |
| C₂H₅–⟨pyrimidine⟩–⟨Ph⟩–OCH₃ | 2 wt % |
| C₂H₅OC₂H₄O–⟨Ph⟩–⟨Ph⟩–CN | 3 wt % |
| C₃H₇O–⟨Ph⟩–⟨Ph⟩–CN | 3 wt % |

Composition Example 5

| Structure | Amount |
|---|---|
| C₃H₇–⟨Cy⟩–⟨Cy⟩–⟨Cy⟩–CH=CH₂ | 9 wt % |
| C₃H₇–⟨dioxane⟩–⟨Cy⟩–⟨Cy⟩–CH=CH₂ | 9 wt % |
| CH₃CH=CHC₂H₄–⟨Cy⟩–⟨Cy⟩–⟨Cy⟩–CH=CH₂ | 9 wt % |
| CH₃CH=CHC₂H₄–⟨Ph⟩–COO–⟨Ph(F,F)⟩–CN | 5 wt % |
| C₃H₇–⟨dioxane⟩–⟨Ph⟩–CN | 6 wt % |

-continued

| Structure | Amount |
|---|---|
| C₄H₉–[dioxane]–C(=O)–[benzene]–CN | 5 wt % |
| C₂H₅–[cyclohexane]–COO–[benzene]–OC₆H₁₃ | 2 wt % |
| C₃H₇–[cyclohexane]–COO–[benzene]–OC₅H₁₁ | 2 wt % |
| C₄H₉–[cyclohexane]–COO–[benzene]–OC₄H₉ | 2 wt % |
| C₄H₉–[cyclohexane]–COO–[benzene]–C₃H₇ | 3 wt % |
| C₅H₁₁–[cyclohexane]–COO–[benzene]–CH₃ | 3 wt % |
| C₂H₅–[benzene]–C≡C–[benzene]–CH₃ | 3 wt % |
| C₃H₇–[cyclohexane]–[cyclohexane]–[benzene]–CH₃ | 6 wt % |
| C₃H₇–[cyclohexane]–[cyclohexane]–[benzene]–C₃H₇ | 8 wt % |
| C₃H₇–[pyrimidine]–[benzene(3,4-diF)] | 10 wt % |
| C₃H₇–[cyclohexane]–[benzene]–[benzene]–F | 4 wt % |
| C₃H₇–[cyclohexane]–[cyclohexane]–COO–[benzene]–F | 3 wt % |
| C₃H₇–[cyclohexane]–COO–[benzene]–COO–[benzene]–F | 2 wt % |
| C₂H₅–[cyclohexane]–COO–[benzene]–CN | 3 wt % |

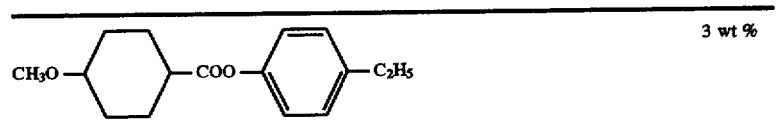 3 wt %
 3 wt %
Composition Example 6
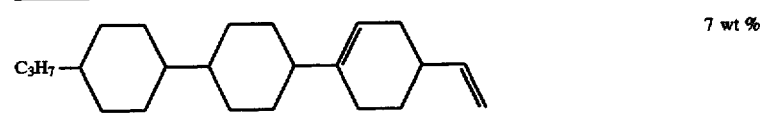 7 wt %
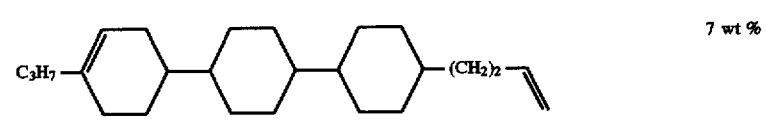 7 wt %
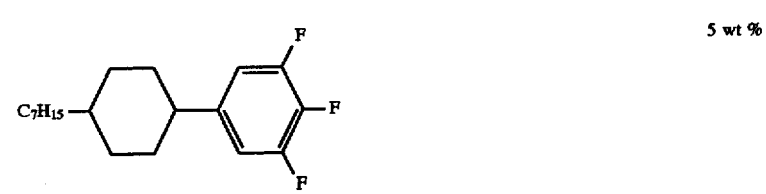 5 wt %
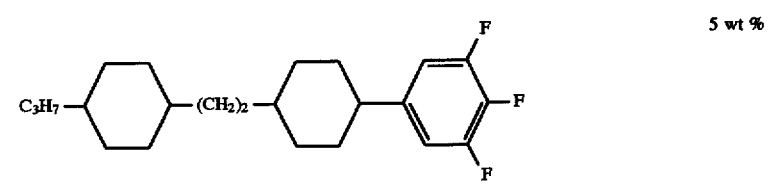 5 wt %
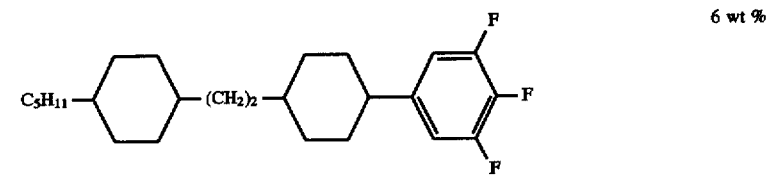 6 wt %
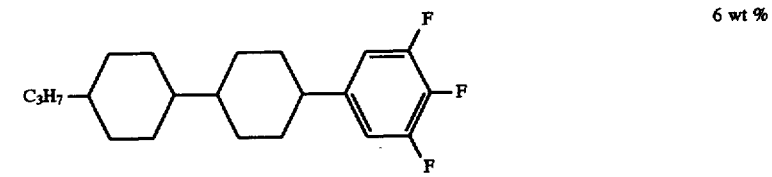 6 wt %
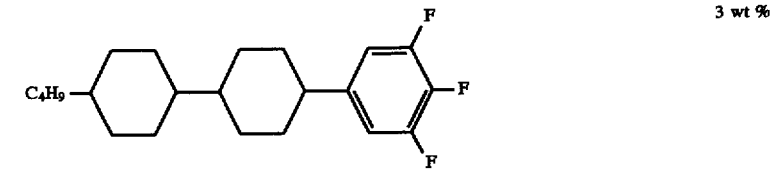 3 wt %
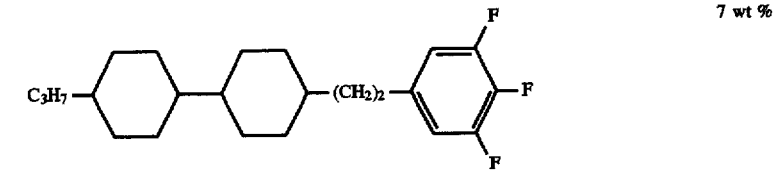 7 wt %

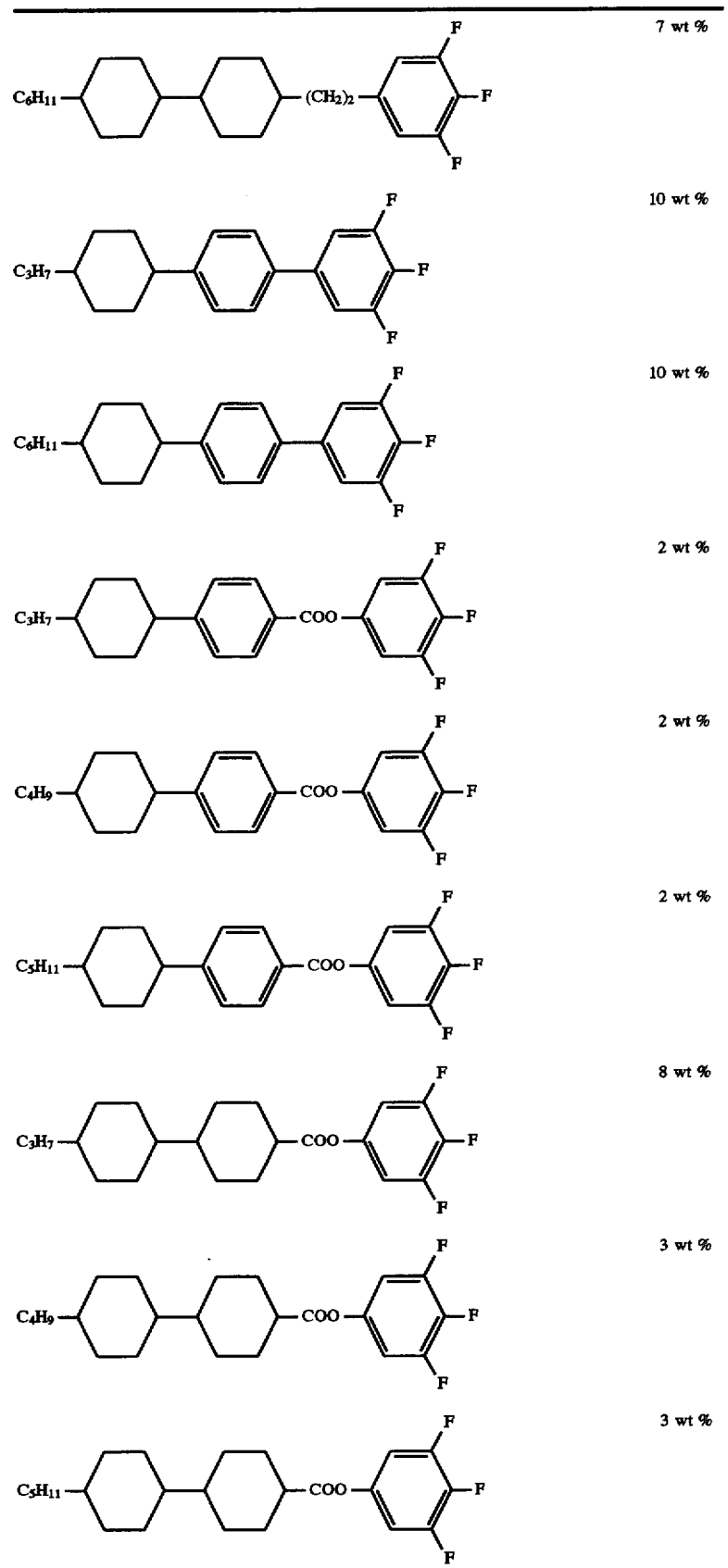

-continued
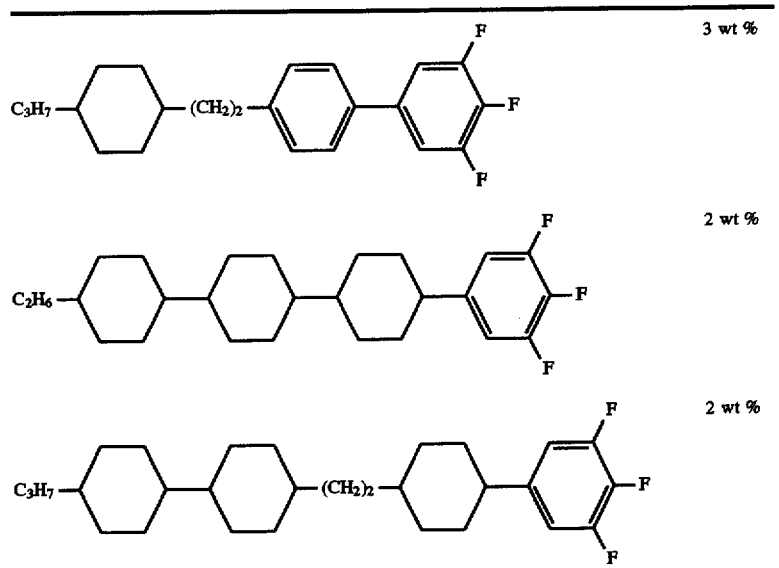
3 wt %
2 wt %
2 wt %
Composition Example 7
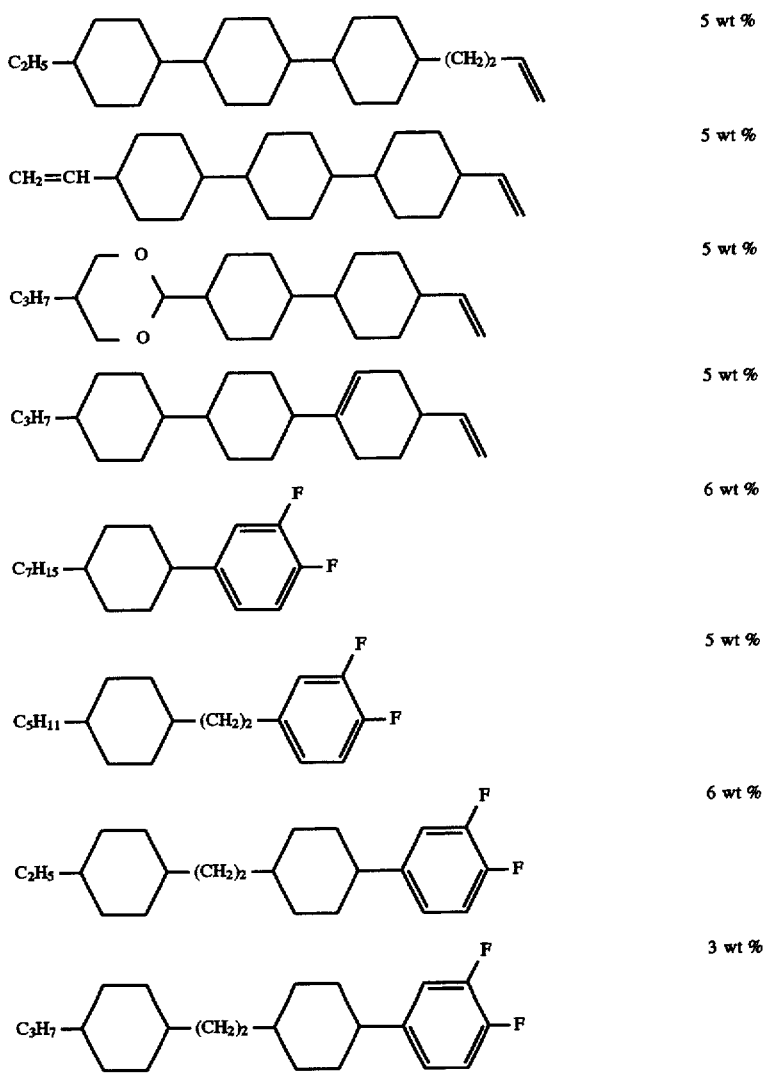
5 wt %
5 wt %
5 wt %
5 wt %
6 wt %
5 wt %
6 wt %
3 wt %

-continued
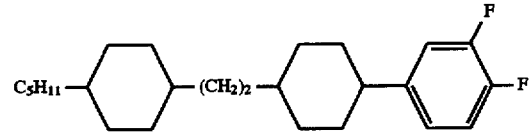 6 wt %
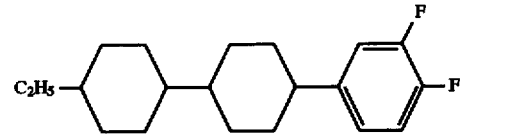 10 wt %
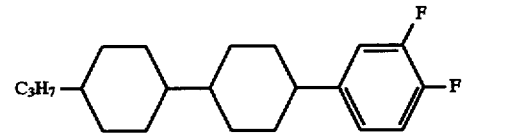 10 wt %
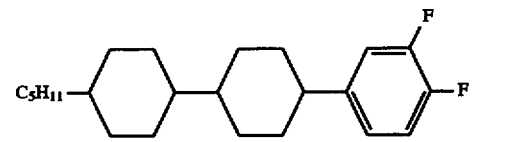 10 wt %
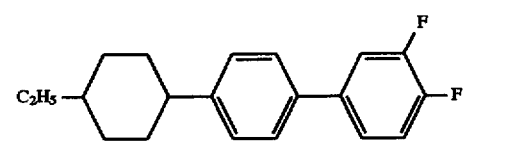 4 wt %
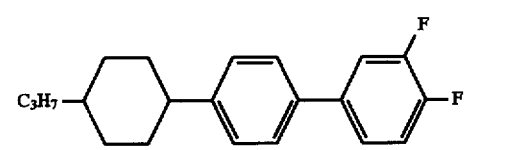 4 wt %
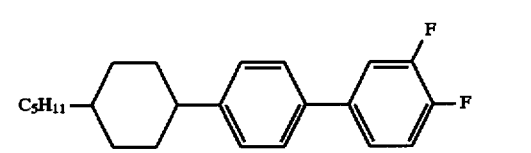 8 wt %
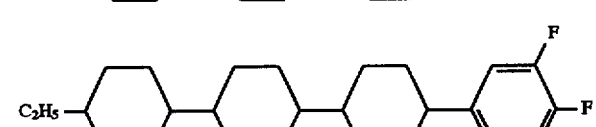 3 wt %
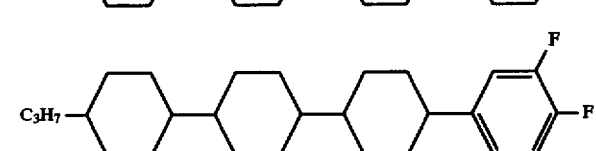 3 wt %
 2 wt %
Composition Example 8
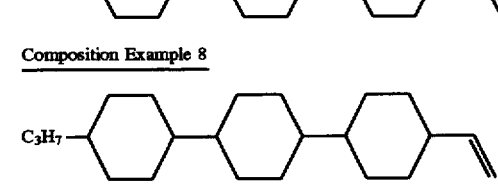 10 wt %

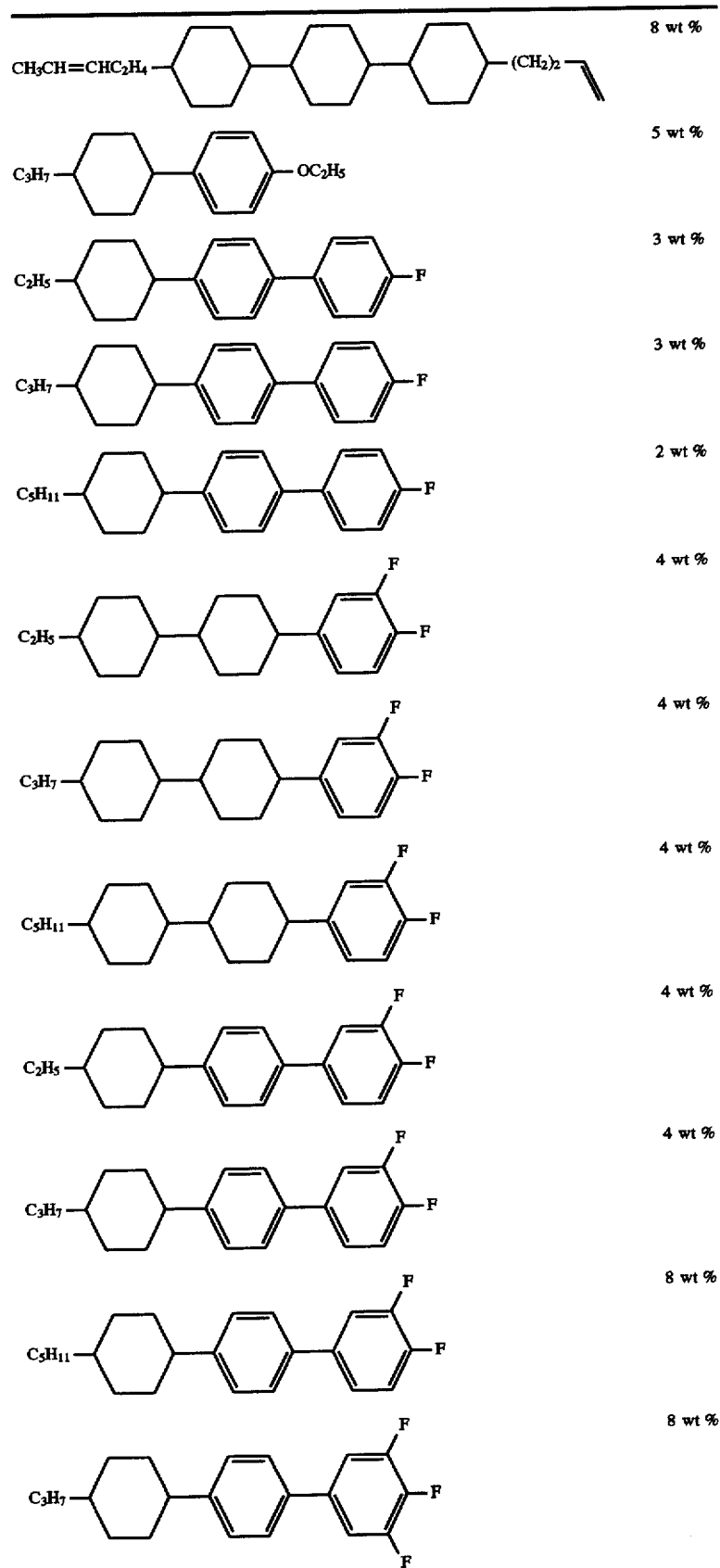

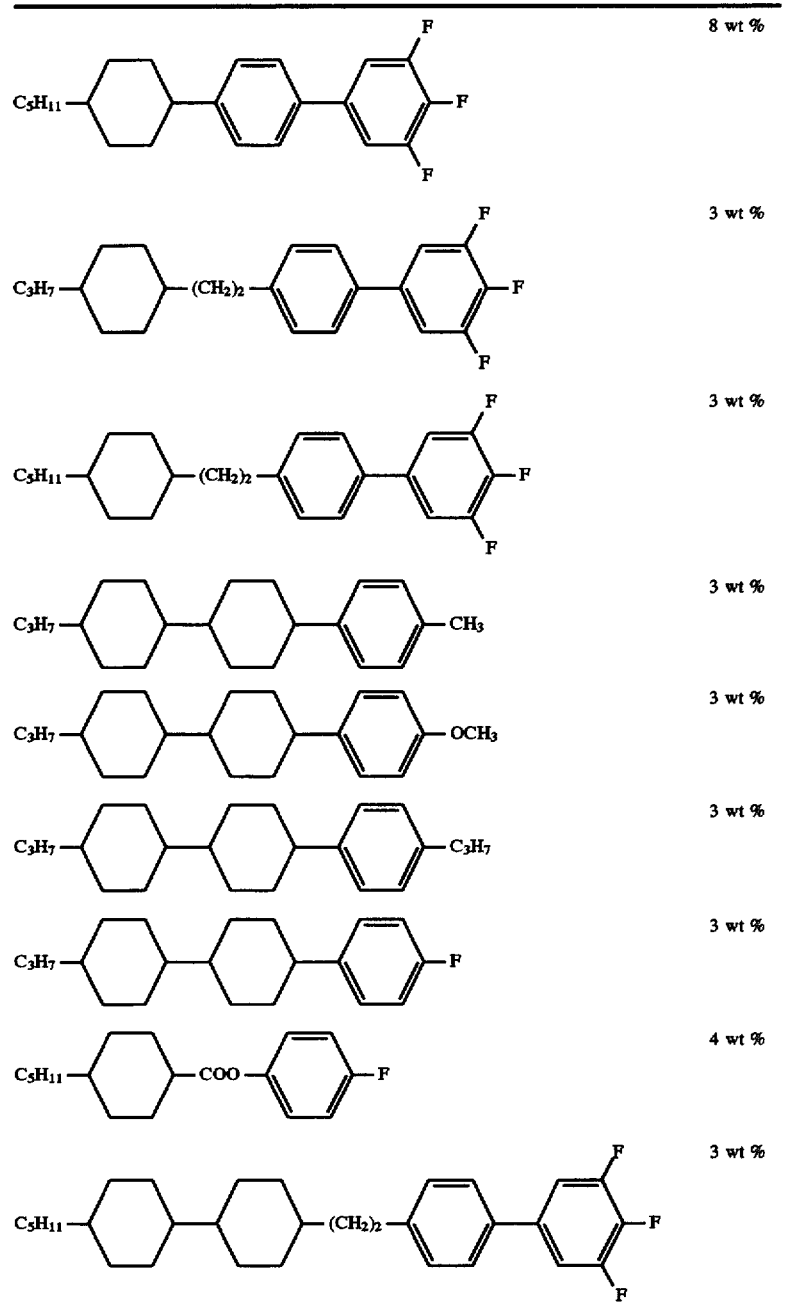
| | |
|---|---|
| | 8 wt % |
| | 3 wt % |
| | 3 wt % |
| | 3 wt % |
| | 3 wt % |
| | 3 wt % |
| | 3 wt % |
| | 4 wt % |
| | 3 wt % |
Composition Example 9
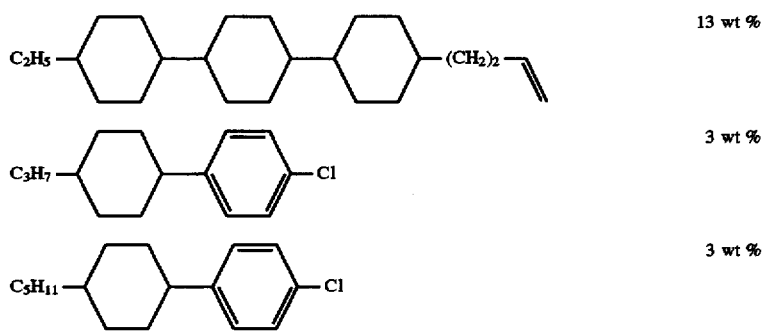
| | |
|---|---|
| | 13 wt % |
| | 3 wt % |
| | 3 wt % |

-continued

| Structure | wt % |
|---|---|
| C₇H₁₅–⟨Cy⟩–⟨Ph⟩–Cl | 4 wt % |
| C₂H₅–⟨Cy⟩–⟨Ph⟩–⟨Ph⟩(3,4-F₂) | 7 wt % |
| C₃H₇–⟨Cy⟩–⟨Ph⟩–⟨Ph⟩(3,4-F₂) | 7 wt % |
| C₅H₁₁–⟨Cy⟩–⟨Ph⟩–⟨Ph⟩(3,4-F₂) | 14 wt % |
| C₂H₅–⟨Cy⟩–⟨Cy⟩–⟨Ph⟩–Cl | 5 wt % |
| C₃H₇–⟨Cy⟩–⟨Cy⟩–⟨Ph⟩–Cl | 5 wt % |
| C₄H₉–⟨Cy⟩–⟨Cy⟩–⟨Ph⟩–Cl | 5 wt % |
| C₃H₇–⟨Cy⟩–⟨Ph⟩(3-F)–C≡C–⟨Ph⟩–C₂H₅ | 3 wt % |
| C₃H₇–⟨Cy⟩–⟨Ph⟩(3-F)–CH=CH–⟨Ph⟩–C₂H₅ | 3 wt % |
| C₃H₇–⟨Cy⟩–⟨Ph⟩–⟨Ph⟩(3,4,5-F₃) | 10 wt % |
| C₅H₁₁–⟨Cy⟩–⟨Ph⟩–⟨Ph⟩(3,4,5-F₃) | 10 wt % |
| C₃H₇–⟨Cy⟩–(CH₂)₂–⟨Cy⟩–⟨Ph⟩(3-F)–Cl | 4 wt % |

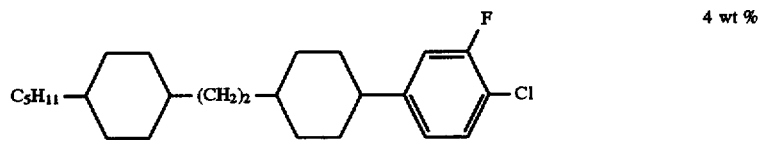 4 wt %
Composition Example 10
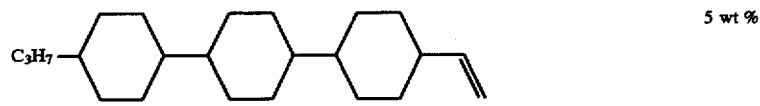 5 wt %
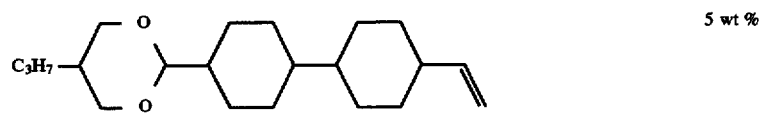 5 wt %
 5 wt %
 10 wt %
 10 wt %
 10 wt %
 5 wt %
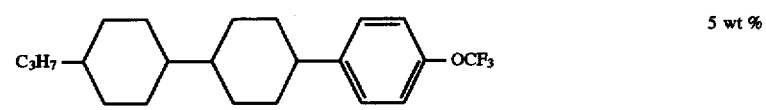 5 wt %
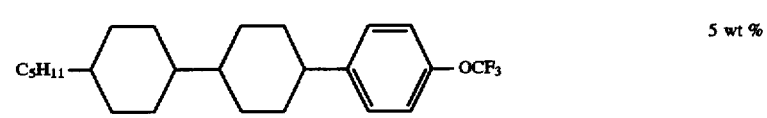 5 wt %
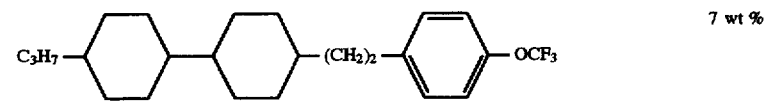 7 wt %
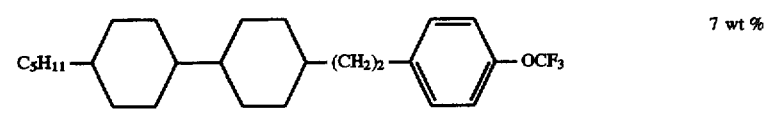 7 wt %
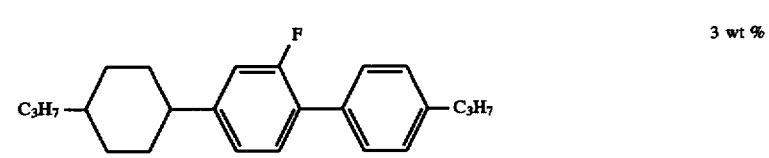 3 wt %

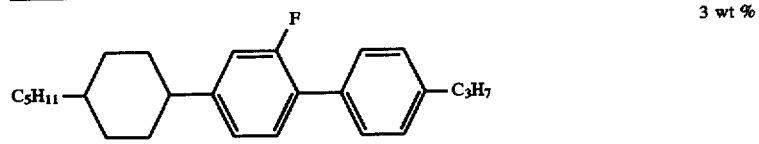 3 wt %
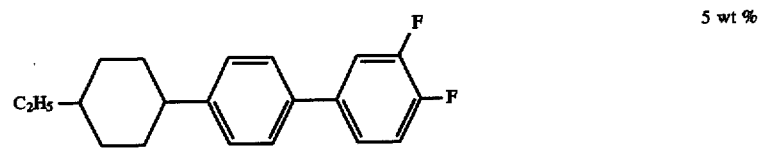 5 wt %
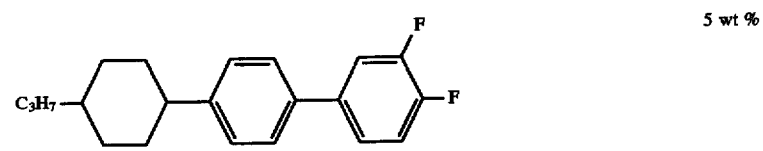 5 wt %
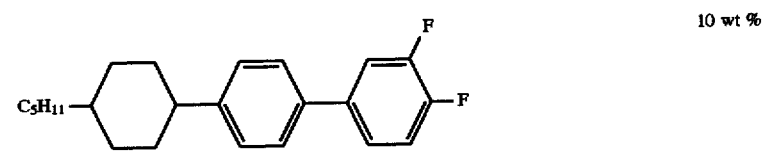 10 wt %
Composition Example 11
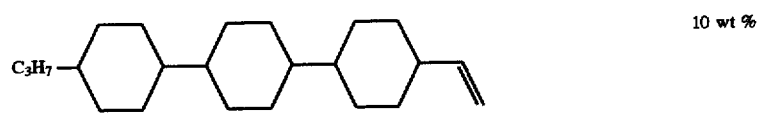 10 wt %
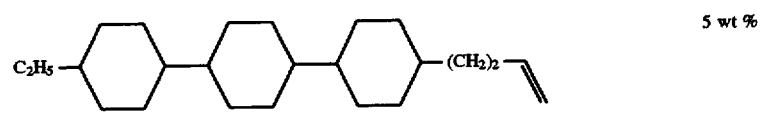 5 wt %
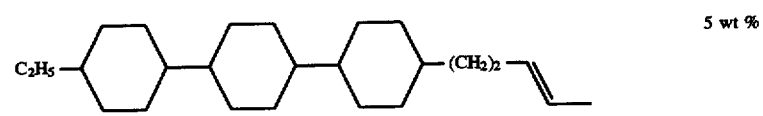 5 wt %
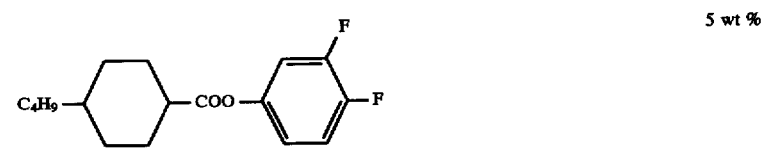 5 wt %
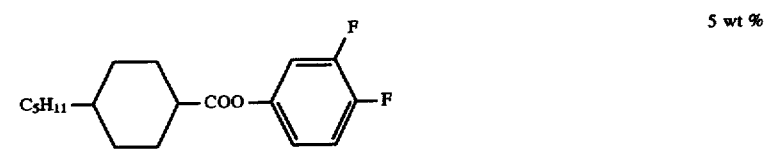 5 wt %
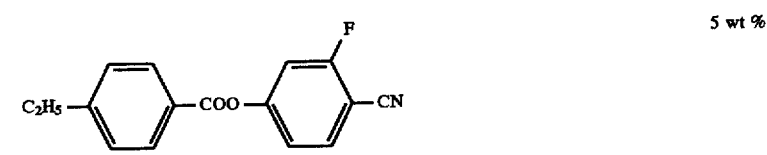 5 wt %
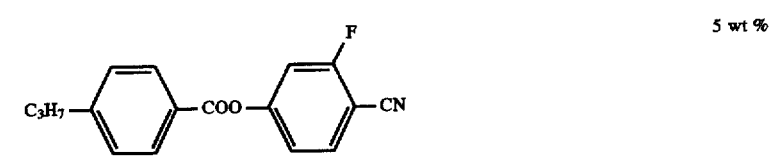 5 wt %

-continued

| Structure | Amount |
|---|---|
| C₄H₉–⟨phenyl⟩–COO–⟨phenyl(3-F,4-CN)⟩ | 5 wt % |
| C₅H₁₁–⟨phenyl⟩–COO–⟨phenyl(3-F,4-CN)⟩ | 5 wt % |
| CH₃OC₃H₆–⟨cyclohexyl⟩–⟨phenyl(3-F,4-CN)⟩ | 6 wt % |
| C₃H₇–⟨cyclohexyl⟩–⟨cyclohexyl⟩–COO–⟨phenyl(3,4-diF)⟩ | 4 wt % |
| C₅H₁₁–⟨cyclohexyl⟩–⟨cyclohexyl⟩–COO–⟨phenyl(3,4-diF)⟩ | 4 wt % |
| C₂H₅–⟨cyclohexyl⟩–⟨phenyl⟩–COO–⟨phenyl(3-F,4-CN)⟩ | 6 wt % |
| C₃H₇–⟨cyclohexyl⟩–⟨phenyl⟩–COO–⟨phenyl(3-F,4-CN)⟩ | 4 wt % |
| C₄H₉–⟨cyclohexyl⟩–⟨phenyl⟩–COO–⟨phenyl(3-F,4-CN)⟩ | 6 wt % |
| C₅H₁₁–⟨cyclohexyl⟩–⟨phenyl⟩–COO–⟨phenyl(3-F,4-CN)⟩ | 4 wt % |
| C₃H₇–⟨cyclohexyl⟩–⟨phenyl⟩–C≡C–⟨phenyl⟩–C₂H₅ | 10 wt % |
| CH₂=CHC₂H₄–⟨cyclohexyl⟩–⟨cyclohexyl⟩–C₃H₇ | 3 wt % |
| CH₂=CHC₂H₄–⟨cyclohexyl⟩–⟨cyclohexyl⟩–⟨phenyl⟩–CH₃ | 3 wt % |

The alkenylcyclohexane derivatives of formula (I) are preferably prepared by the following processes. 1) The compounds of formulae (I-1) to (I-5) and (I-8) to (I-11) can be prepared by known process using Wittig reaction, e.g., a process described in ORGANIC REACTIONS, Vol. 14, Chapter 3, which is illustrated by the following reaction scheme.

phosphonium chloride in the presence of a base such as sodium alcoholate or an alkyl lithium in THF or an ether solvent such as diethyl ether. The ylide is reacted with a cyclohexanone derivative (11) to produce a compound (12). The compound (12) is reacted with a mineral acid such as hydrochloric acid and sulfuric acid or an organic acid such

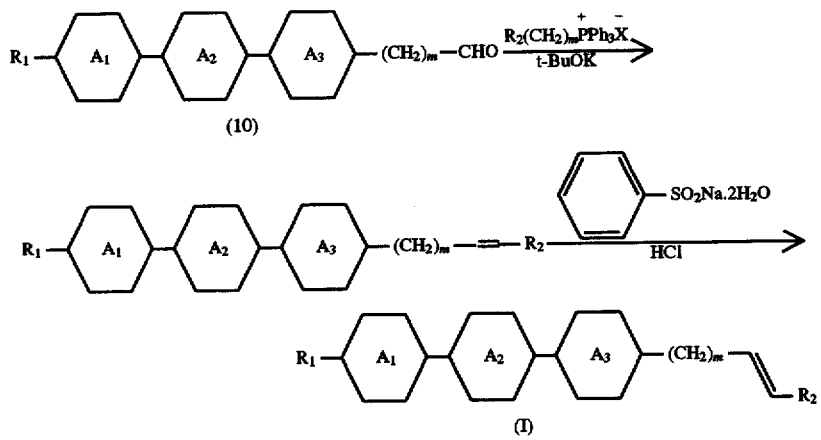

Referring to the above reaction scheme, an aldehyde derivative (10) is reacted with an alkyltriphenylphosphonium halide in an ether solvent such as tetrahydrofuran (THF) or diethyl ether in the presence of a base such as sodium methylate, potassium t-butoxide (t-BuOK) or n-butyl lithium. This reaction is preferably carried out at $-20°$ to $0°$ C. in an inert gas stream. Subsequent reaction with benzenesulfinic acid or p-toluenesulfinic acid can produce the compound (I).

The aldehyde derivatives (10) can be prepared in accordance with the following reaction scheme.

as formic acid and acetic acid to provide an aldehyde derivative of formula (10-1)(m=0).

Alternatively, the compounds (13) and (15) can be prepared by reacting the compound (11) with an ylide prepared from the reaction of ethyl diethylphosphinoacetate and [2-(1,3-dioxoran-2-yl)ethyl]triphenylphosphonium bromide in the presence of the same base as mentioned above. The compound (13) can be reduced with hydrogen in the presence of a palladium/carbon catalyst to provide a compound (14) which is further reduced with diisobutylaluminium hydride (DIBAL) to prepare the aldehyde (10-3)(m=1). The

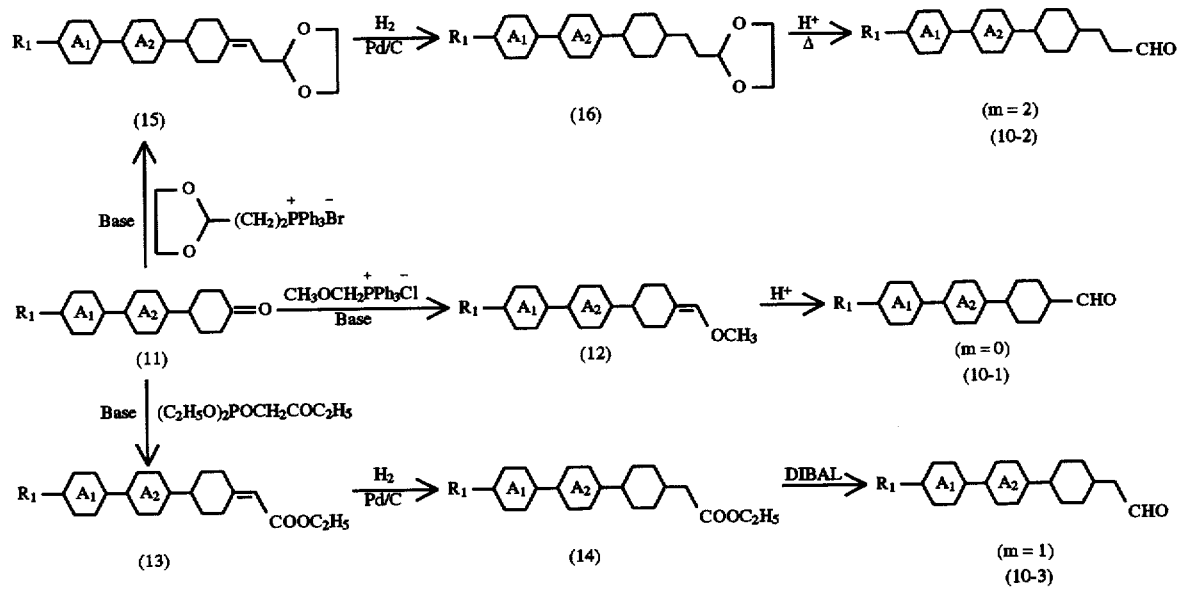

Referring to the above reaction scheme, an ylide is prepared by the reaction with methoxymethyltriphenylcompound (15) can be reduced with hydrogen in the presence of a palladium/carbon catalyst to provide the compound (16), which is further reacted with a mineral acid such as hydrochloric acid and sulfuric acid or an organic acid such as formic acid and acetic acid to prepare the aldehyde derivative (10-2)(m=2).

Other aldehyde derivatives (10) than those of m=0–2 can be prepared from the aldehyde derivatives (10-1 to 10-3) as starting materials by repeating and/or combining the above-mentioned procedures.

The compounds (I-6) and (I-7) can be prepared according to the following reaction scheme.

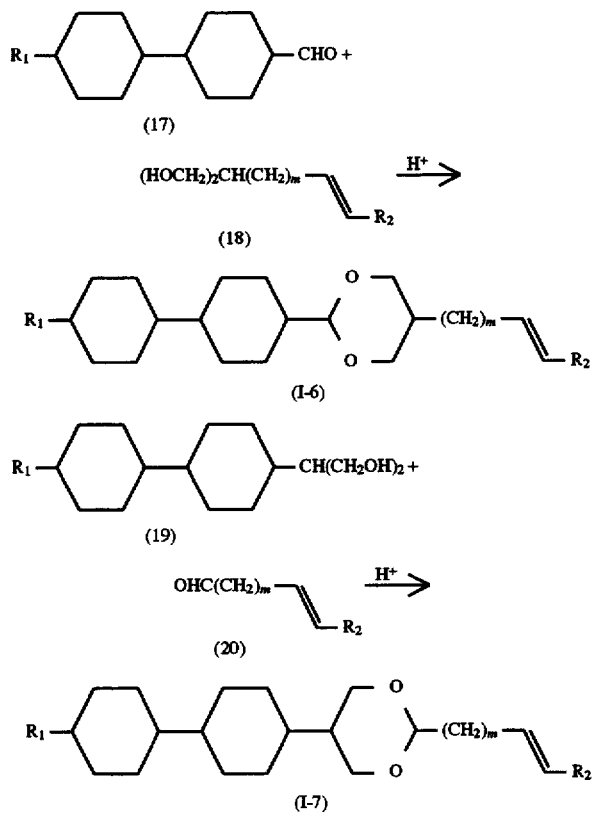

More specifically, the compound (I-6) is prepared by the reaction of the aldehyde derivative (17) with a propylene glycol derivative (18) in the presence of a mineral acid such as hydrochloric acid or sulfuric acid or an organic acid such as formic acid, acetic acid or p-toluenesulfonic acid.

Similarly, the compound (I-7) is prepared from the compounds (19) and (20).

The compounds (I-12) and (I-13) can be prepared according to the following reaction scheme.

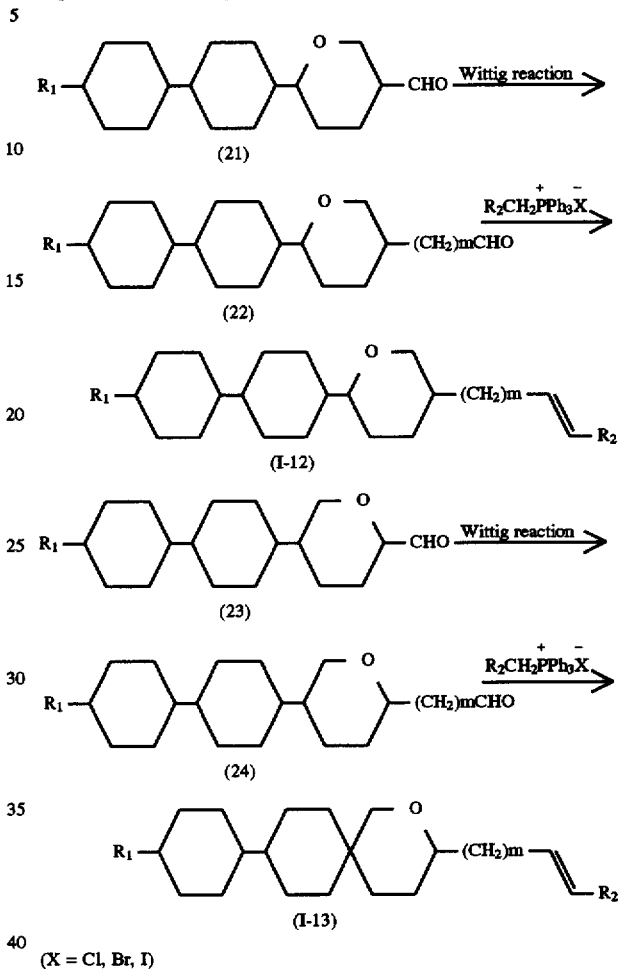

(X = Cl, Br, I)

Starting from the tetrahydropyrane derivatives (21) and (23) obtained by known processes disclosed in COMPREHENSIVE HETEROCYCLIC CHEMISTRY, Vol. 3 and Japanese Patent Kokai 59-164788, repeated Wittig reaction can produce the compounds (I-12) and (I-13).

The compounds of formula (I) wherein $R_1$ is an alkenyl group can be prepared according to the following reaction scheme.

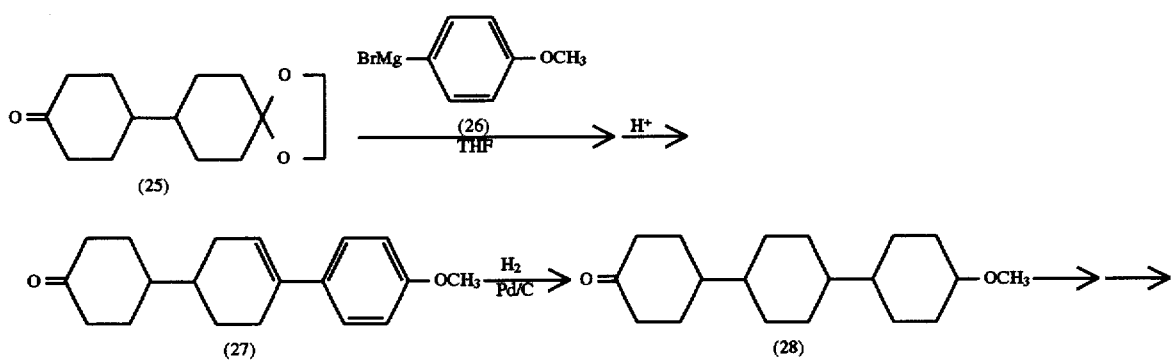

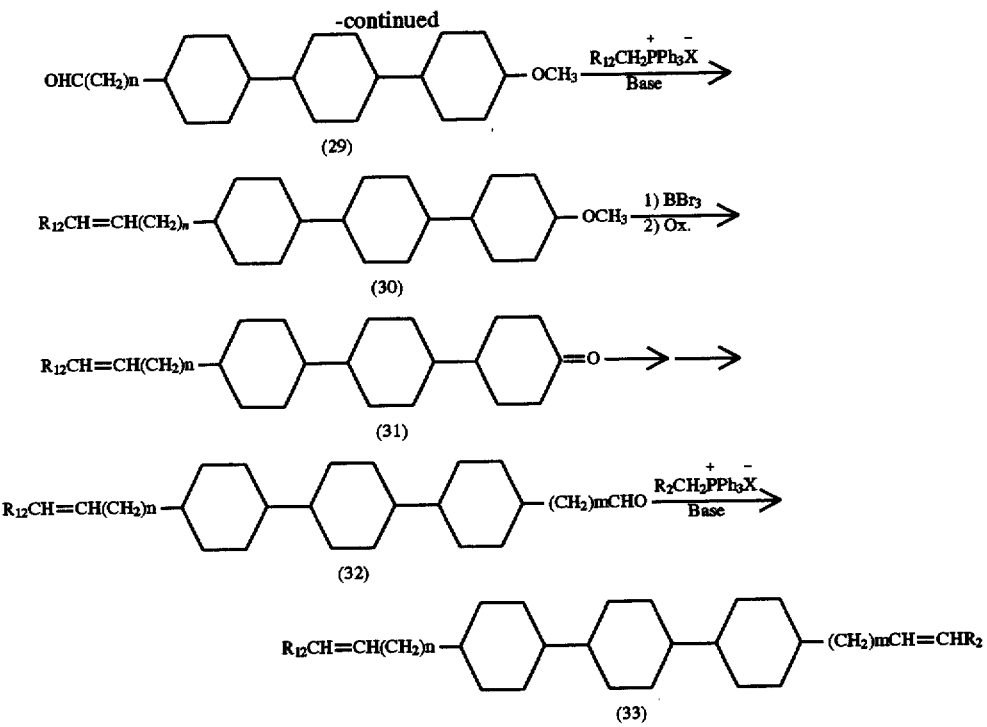

(X = Cl, Br, I)

Referring to the above reaction scheme, the cyclohexanone derivative (25) (as disclosed in Japanese Patent Kokai 6-247886) is reacted with Grignard reagent (26) and subsequently with a mineral acid such as hydrochloric acid and sulfuric acid or an organic acid such as acetic acid and p-toluenesulfonic acid to prepare the compound (27). The compound (27) is reduced with hydrogen in the presence of Raney nickel, palladium, rhodium or platinum catalyst to provide the compound (28). The compound (28) is converted to the aldehyde derivative (29) by the same procedure as mentioned before for the preparation of the compound (10). The compound (29) is reacted with the ylide prepared from an alkyltriphenylphosphonium halide in the presence of a base to produce the compound (30) of the formula wherein $R_{12}$ is a hydrogen atom or an alkyl group of 13-n carbon atoms and n is 0–13. The compound (30) is demethylated by the action of boron tribromide and the resulting alcohol is treated with a suitable oxidizing agent such as Jones reagent or sodium hypochlorite to prepare the compound (31). The compound (31) is converted to the aldehyde derivative (32) according to the same procedure as done for the preparation of the compound (10). The compound (33) is reacted with the ylide prepared from an alkyltriphenylphosphonium halide in the presence of a base to prepare the compound (33).

As an alternative process, the compound (28) is converted by Wittig reaction to the compound (34) which is treated with an oxidizing agent to produce the carboxylic acid derivative (35). The compound (35) is converted to the corresponding methyl ester derivative which is then demethylated and treated with an oxidizing agent in a similar manner as in the preparation of the compound (31) from the compound (30), to prepare the compound (38). The compound (38) is subjected to Wittig reaction to prepare the compound (39) which is then reduced with DIBAL to prepare the compound (40). This compound can be subjected to Wittig reaction to produce the compound (33).

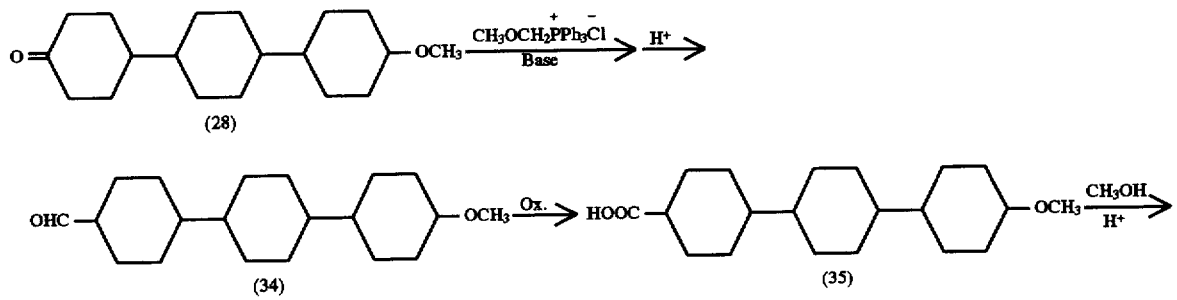

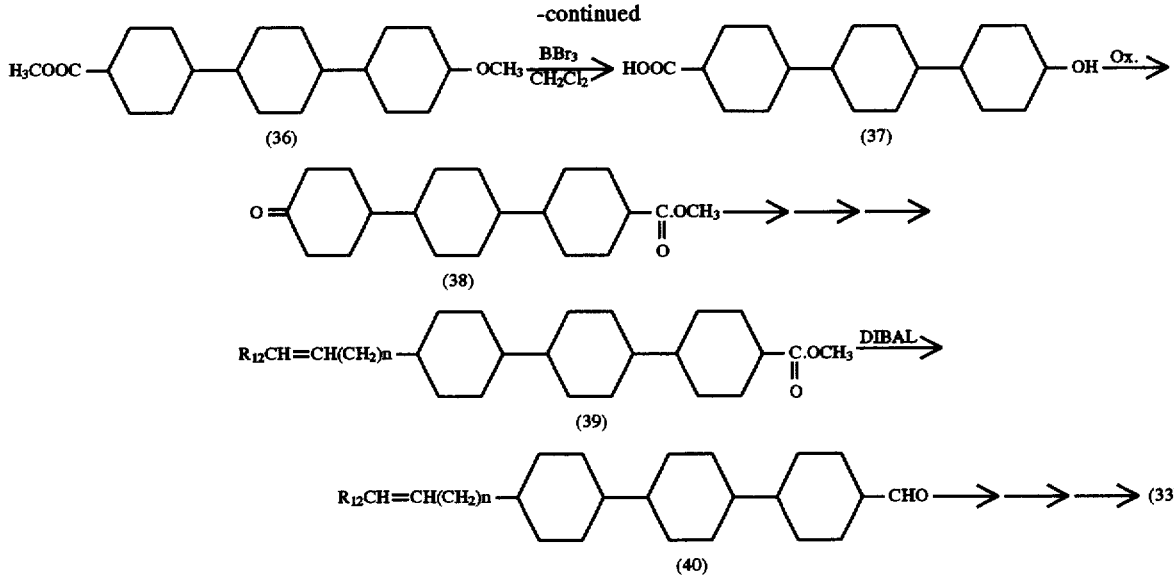

Other compounds having a hetero-ring such as a 1,3-dioxane-2,5-diyl group and a 1,3-dithian-2,5-diyl group can be prepared in a similar manner as described above.

The compound having an ether bond in the alkyl chain can be prepared in accordance with the following reaction scheme.

for a nematic liquid crystal composition, especially that suitable for the STN type display mode.

This invention will be further illustrated by the following examples. The structure of the compound obtained by Examples was confirmed by means of nuclear magnetic resonance spectrum ($^1$H-NMR), mass spectrum (MS). In

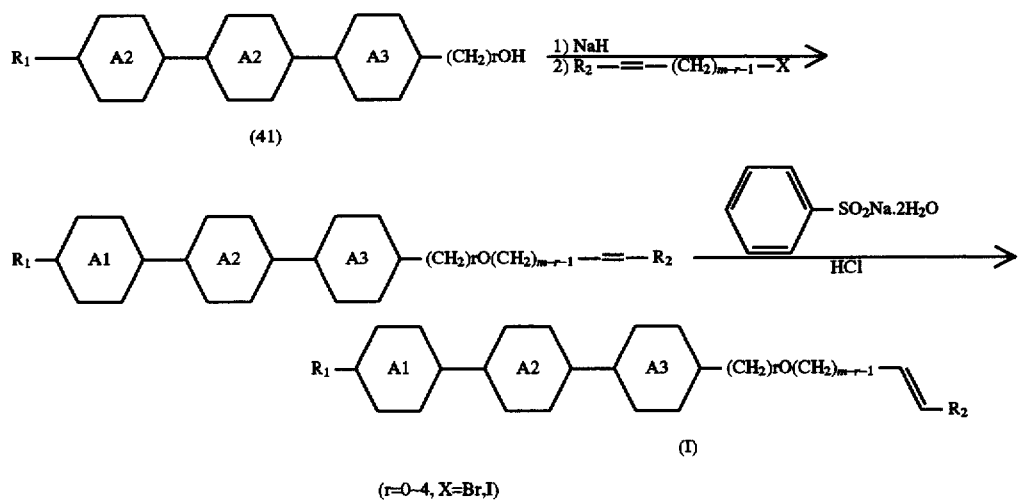

The aldehyde derivative is reduced with lithium aluminum hydride or aluminum borohydride to provide the alcohol derivative (41). The compound (41) is treated with sodium hydride and the like in a polar solvent such as N,N-dimethylformamide (DMF) and THF to provide the corresponding alcoholate. The alcoholate is reacted with an alkenyl halide to afford an intermediate. Isomerization of the intermediate can produce the compound of formula (I).

The present liquid crystalline compounds of formula (I) can exhibit a high elastic constant ratio ($K_{33}/K_{11}$), a low viscosity and a nematic phase over a broad temperature range. In addition, they have good compatibility with other various liquid crystal materials and a good solubility even at a lower temperature. Thus, the liquid crystalline compounds of the present invention are highly excellent as a component NMR of these examples, d represents a doublet, m does a multiplet, and J does a coupling constant, and M$^+$ represents a molecular ion peak. Cr represents a crystal phase, SB does a smectic B phase, N does a nematic phase, Iso does an isotropic liquid phase and all phase transition temperatures are shown by a unit of °C.

EXAMPLE 1

Preparation of 1-ethenyl-trans-4-(trans-4-(trans-4-propylcyclohexyl)cyclohexyl)cyclohexane [Compound No. 1 of formula (I) wherein $R_1$ is $C_3H_7$, the rings $A_1$, $A_2$ and $A_3$ are trans-1,4-cyclohexylene groups, m is 0, and $R_2$ is H]

A mixture of 8.66 g (21.4 mmol) of methyltriphenylphosphonium iodide and 70 ml of THF was cooled to −50° C. To this mixture was added 2.66 g (23.5 mmol) of t-BuOK and the resulting mixture was stirred for one hour. To this mixture was added dropwise, while maintaining a temperature at below −50° C., a solution of 5.46 g (17.1 mmol) of trans-4-(trans-4-(trans-4-propylcyclohexyl)cyclohexyl) cyclohexyl carbaldehyde in 100 ml of THF. After completion of the dropwise addition, the reaction temperature was gradually allowed to rise up to room temperature and the mixture was stirred for further 5 hours. After the reaction was completed by adding 50 ml of water, the reaction mixture was extracted with 300 ml of toluene. The organic layer was washed three times with 100 ml of water and dried over anhydrous magnesium sulfate. The solvent was distilled off under reduced pressure. A silica gel column chromatography (a developing solvent: heptane) of the residue gave crude 1-ethenyl-trans-4-(trans-4-(trans-4-propylcyclohexyl)cyclohexyl)cyclohexane. This crude compound was then recrystallized from heptane to give 2.56 g (Yield, 47.2%) of the title compound.

Phase transition temperature: Cr below room temperature, SB 232.0 Iso

NMR: δ=0.45–2.20(37H, m), 4.86(1H, d d d, J=10.8, 2.2, 0.6 Hz), 4.93(1H, d d d, J=16.2, 2.2, 0.9 Hz), 5.78(1H, d d d, J=16.2, 10.8, 6.3 Hz) MS: m/e=316 (M$^+$)

EXAMPLE 2

Preparation of 1-((E)-1-propenyl)-trans-4-(trans-4-(trans-4-propylcyclohexyl)cyclohexyl)cyclohexane (Compound No. 65 of formula (I) wherein $R_1$ is $C_3H_7$, the rings $A_1$, $A_2$ and $A_3$ are trans-1,4-cyclohexylene groups, m is 0 and $R_2$ is —$CH_3$)

A mixture of 7.28 g (19.6 mmol) of ethyltriphenylphosphonium bromide and 70 ml of THF was cooled to −50° C. To this mixture was added 2.42 g (21.6 mmol) of t-BuOK and the resulting mixture was stirred for one hour. To this mixture was added dropwise, while maintaining a temperature at below −50° C., a solution of 5.00 g (15.7 mmol) of trans-4-(trans-4-(trans-4-propylcyclohexyl)cyclohexyl) cyclohexyl carbaldehyde. After completion of the dropwise addition, the reaction temperature was gradually allowed to rise up to room temperature and the mixture was stirred for further 5 hours. After the reaction was completed by adding 50 ml of water, the reaction mixture was extracted with 300 ml of toluene. The organic layer was washed three times with 100 ml of water and dried over anhydrous magnesium sulfate. The solvent was distilled off under reduced pressure. A silica gel column chromatography (a developing solvent: heptane) of the residue gave 2.70 g of crude 1-((E)-1-propenyl)-trans-4-(trans-4-(trans-4-propylcyclohexyl) cyclohexyl)cyclo-hexane.

2.70 g (8.17 mmol) of the crude product was mixed with 2.45 g (12.3 mmol) of sodium benzenesulfinate dihydrate, 2.0 ml (12.3 mmol) of 6N hydrochloric acid and 20 ml of a mixed solvent of toluene/ethanol (1/1) and the resulting mixture was heated under reflux for 16 hours. After cooling to room temperature, 50 ml of water was added to the reaction mixture which was then extracted with 150 ml of toluene. The organic layer was washed three times with a saturated aqueous solution of sodium carbonate and three times with water and dried over anhydrous magnesium sulfate. The solvent was distilled off under reduced pressure and the residue was subjected to a silica gel column chromatography (developing solvent=toluene) to give 2.32 g of crude 1-((E)-1-propenyl)-trans-4-(trans-4-(trans-4-propylcyclohexyl)cyclohexyl)cyclohexane. Recrystallization of the crude compound from a mixed solvent of ethyl acetate/heptane (13/7) gave 2.16 g (Yield, 41.6%) of the title compound.

MS: m/e=330 (M$^+$)

EXAMPLE 3

Preparation of 1-(2-propenyloxy)-trans-4-(trans-4-(trans-4-propylcyclohexyl)cyclohexyl)cyclohexane (Compound No. 206 of formula (I) wherein $R_1$ is $C_3H_7$, the rings $A_1$, $A_2$ and $A_3$ are trans-1,4-cyclohexylene groups, $(CH_2)_m$ is $OCH_2$ and $R_2$ is H)

To a solution of 10.0 g (33.1 mmol) of trans-4-(trans-4-(trans-4-propylcyclohexyl)cyclohexyl)cyclohexanol in 100 ml of DMF was added dropwise, while stirring the solution at room temperature, a suspension of 1.19 g (49.6 mmol) of NaH in 10 ml of DMF. After completion of the dropwise addition, the reaction mixture was stirred for 2 hours and then the temperature of the reaction mixture was gradually allowed to rise up to 80° C. and a solution of 4.80 g (39.7 mmol) of 1-bromo-3-propene in 20 ml of DMF was added dropwise. After completion of the dropwise addition, the mixture was heated under reflux at the same temperature for 5 hours. After the reaction solution was allowed to cool down to room temperature, the reaction product was poured into an ice-water and extracted with 500 ml of toluene. The organic layer was washed three times with water, dried over anhydrous magnesium sulfate and the solvent was distilled off under reduced pressure. A silica gel column chromatography (developing solvent: toluene) of the residue gave crude 1-(2-propenyloxy)-trans-4-(trans-4-(trans-4-propylcyclohexyl)cyclohexyl)cyclohexane. This crude product was recrystallized from heptane to give 5.74 g (Yield, 50.1%) of the title compound. MS: m/e=346 (M$^+$)

EXAMPLE 4

Preparation of 1-((E)-2-butenyloxy)-trans-4-(trans-4-(trans-4-propylcyclohexyl)cyclohexyl)cyclohexane (Compound No. 279 of formula (I) wherein $R_1$ is $C_3H_7$, the rings $A_1$, $A_2$ and $A_3$ are trans-1,4-cyclohexylene groups, $(CH_2)_m$ is $OCH_2$ and $R_2$ is —$CH_3$)

To a solution of 10.0 g (33.1 mmol) of trans-4-(trans-4-(trans-4-propylcyclohexyl)cyclohexyl)cyclohexanol in 100 ml of DMF was added dropwise, while stirring the solution at room temperature, a suspension of 1.19 g (49.6 mmol) of NaH in 10 ml of DMF. After completion of the dropwise addition, the reaction mixture was stirred for 2 hours and then the temperature of the reaction mixture was gradually allowed to rise up to about 80° C. and a solution of 5.35 g (39.7 mmol) of 1-bromo-2-butene in 20 ml of DMF was added dropwise. After completion of the dropwise addition, the mixture was heated under reflux at the same temperature for 5 hours. After the reaction solution was allowed to cool down to room temperature, the reaction product was poured into an ice-water and extracted with 500 ml of toluene. The organic layer was washed three times with water, dried over anhydrous magnesium sulfate and the solvent was distilled off under reduced pressure. A silica gel column chromatography (developing solvent: toluene) of the residue gave 5.96 g of crude 1-(2-butenyloxy)-trans-4-(trans-4-(trans-4-propylcyclohexyl)cyclohexyl)cyclohexane.

5.96 g (16.5 mmol) of the crude product was mixed with 4.96 g (24.8 mmol) of sodium benzenesulfinate dihydrate, 4.1 ml (24.8 mmol) of 6N hydrochloric acid and 40 ml of a mixed solvent of toluene/ethanol (1/1) and the resulting mixture was heated under reflux for 16 hours. After completion of the reaction, 100 ml of water was added to the reaction mixture and extracted with 300 ml of toluene. The organic layer was washed three times with a saturated aqueous solution of sodium carbonate and three times with water and dried over anhydrous magnesium sulfate. The solvent was distilled off under reduced pressure and the residue was subjected to a silica gel column chromatography (developing solvent=toluene) to give 4.89 g of crude 1-((E)-2-butenyloxy)-trans-4-(trans-4-(trans-4-propylcyclohexyl) cyclohexyl)cyclohexane. Recrystallization of the crude compound from a mixed solvent of ethyl acetate/heptane (3/7) gave 4.40 g (Yield, 36.9%) of the title compound. MS: m/e=360 (M$^+$)

EXAMPLE 5

Preparation of 1-ethenyl-trans-4-(trans-4-(trans-4-ethenylcyclohexyl)cyclohexyl)cyclohexane (Compound No. 419 of formula (I) wherein $R_1$ is $CH_2$=CH, the rings $A_1$, $A_2$ and $A_3$ are trans-1,4-cyclohexylene groups, m is 0, and $R_2$ is H)

A mixture of 30.2 g (74.7 mmol) of methyltriphenylphosphonium iodide and 400 ml of THF was cooled to −50° C. To this mixture was added 9.23 g (82.2 mmol) of t-BuOK and the resulting mixture was stirred for one hour. To this mixture was added dropwise a solution of 20.0 g (59.8 mmol) of trans-4-(trans-4-(trans-4-formylcyclohexyl) cyclohexyl)cyclohexane carboxylic acid methyl ester in 500 ml of THF, while maintaining a temperature at below −50° C. After the dropwise addition, the reaction temperature was gradually allowed to rise up to room temperature. After 300 ml of water was added to the reaction mixture, the reaction mixture was extracted with 1000 ml of toluene. The organic layer was washed three times with water and dried over anhydrous magnesium sulfate. The solvent was distilled off under reduced pressure and the residue was subjected to a silica gel column chromatography (a developing solvent: heptane) to give 9.90 g of crude trans-4-(trans-4-(trans-4-ethenylcyclohexyl)cyclohexyl)-cyclohexane carboxylic acid methyl ester.

A solution of 9.90 g (29.8 mmol) of the crude product in 100 ml of THF was cooled to −50° C. and stirred. To this solution was added dropwise 35.8 ml of a 1.0M solution of DIBAL in THF while maintaining a temperature at below −50° C. After stirring at the same temperature for 5 hours, 30 ml of methanol was added to the reaction mixture, the mixture was filtered through Celite and the filtrate was extracted with 150 ml of toluene. The organic layer was washed three times with water, dried over anhydrous magnesium sulfate and the solvent was distilled off under reduced pressure. The residue was subjected to a silica gel column chromatography (developing solvent: mixed solution of toluene/ethyl acetate (3/7)) to give crude trans-4-(trans-4-(trans-4-ethenylcyclohexyl)-cyclohexyl)cyclohexyl carbaldehyde. Recrystallization of this crude compound from ethyl acetate/heptane (2/3) gave 8.11 g of the purified product.

A mixture of 13.5 g (33.5 mmol) of methyltriphenylphosphonium iodide and 200 ml of THF was cooled to −50° C. To this mixture was added 4.13 g (36.8 mmol) of t-BuOK and the resulting mixture was stirred for one hour. To this mixture was added dropwise, while maintaining a temperature at below −50° C., a solution of 8.11 g (26.8 mmol) of trans-4-(trans-4-(trans-4-ethenylcyclohexyl)cyclohexyl) cyclohexyl carbaldehyde in 250 ml of THF. After the dropwise addition, the temperature of the reaction solution was gradually allowed to rise up to room temperature. After 150 ml of water was added to the reaction mixture, the reaction mixture was then extracted with 500 ml of toluene. The organic layer was washed three times with water and dried over anhydrous magnesium sulfate. The solvent was distilled off under reduced pressure and the residue was subjected to a silica gel column chromatography (a developing solvent: heptane) to give 4.12 g of crude 1-ethenyl-trans-4-(trans-4-(trans-4-ethenylcyclohexyl)-cyclohexyl) cyclohexane. Recrystallization from heptane gave 2.99 g (Yield, 16.7%) of the title compound. MS: m/e=300 (M$^+$)

EXAMPLE 6

Preparation of 1-ethenyl-trans-4-(trans-4-(trans-4-((E)-3-pentenyl)cyclohexyl)cyclohexyl)cyclohexane (Compound No. 473 of formula (I) wherein $R_1$ is $CH_3CH$=$CH(CH_2)_2$, the rings $A_1$, $A_2$ and $A_3$ are trans-1-cyclohexylene groups, m is 0, and $R_2$ is H)

A mixture of 45.4 g (122 mmol) of ethyltriphenylphosphonium iodide and 600 ml of THF was cooled to −50° C. To this mixture was added 15.1 g (135 mmol) of t-BuOK and the resulting mixture was stirred for one hour. To this mixture was added dropwise, while maintaining a temperature at below −50° C., a solution of 30.0 g (97.9 mmol) of trans-4-(trans-4-(trans-4-formylethyl)-cyclohexyl) cyclohexyl)cyclohexane carboxylic acid methyl ester in 750 ml of THF. After the dropwise addition, the reaction temperature was gradually raised to room temperature. After 450 ml of water were added to the reaction mixture, the reaction mixture was extracted with 1500 ml of toluene. The organic layer thus obtained was washed three times with water and dried over anhydrous magnesium sulfate. The solvent was distilled off under reduced pressure and the residue was subjected to a silica gel column chromatography (a developing solvent: heptane) to give 16.9 g of crude trans-4-(trans-4-(trans-4-(3-pentenyl)cyclohexyl) cyclohexyl)cyclohexane carboxylic acid methyl ester.

A solution of 16.9 g (45.1 mmol) of the crude product thus obtained in 150 ml of THF was cooled to −50° C. To this solution was added dropwise 54.1 ml of a 1.0M solution of DIBAL in THF was added dropwise, while stirring and maintaining a temperature at below −50° C. After stirring at the same temperature for 5 hours, 45 ml of methanol was added to the reaction mixture, the resulting mixture was filtered through Celite and the filtrate was extracted with 250 ml of toluene. The organic layer was washed three times with water, dried over anhydrous magnesium sulfate and the solvent was distilled off under reduced pressure. The residue was subjected to a silica gel column chromatography (developing solvent: mixed solution of toluene/ethyl acetate (3/7)) to give crude trans-4-(trans-4-(trans-4-(3-pentenyl) cyclohexyl)cyclohexyl)cyclohexyl carbaldehyde. Recrystallization of this crude compound from a mixed solvent of ethyl acetate/heptane (2/3) to give 14.3 g of the purified product.

A mixture of 21.0 g (51.9 mmol) of methyltriphenylphosphonium iodide and 300 ml of THF was cooled to −50° C. To this mixture was added 6.40 g (57.1 mmol) of t-BuOK and the resulting mixture was stirred for one hour. To this mixture was added dropwise, while maintaining a temperature at below −50° C., a solution of 14.3 g (41.5 mmol) of trans-4-(trans-4-(trans-4-(3-pentenyl)-cyclohexyl) cyclohexyl)cyclohexyl carbaldehyde in 400 ml of THF. After the dropwise addition, the reaction temperature was gradually raised to room temperature. After 250 ml of water was added to the reaction mixture, the reaction mixture was then extracted with 750 ml of toluene. The organic layer was washed three times with water and dried over anhydrous magnesium sulfate. The solvent was distilled off under reduced pressure and the residue was subjected to a silica gel column chromatography (a developing solvent: heptane) to give 6.92 g of crude 1-ethenyl-trans-4-(trans-4-(trans-4-(3-pentenyl)cyclohexyl)cyclohexyl)cyclohexane.

6.92 g (20.2 mmol) of the crude product was mixed with 12.2 g (60.5 mmol) of sodium benzenesulfinate dihydrate, 10.1 ml (60.5 mmol) of 6N hydrochloric acid and 100 ml of a mixed solvent of toluene/ethanol (1/1) and the resulting mixture was heated under reflux for 16 hours. After completion of the reaction, 200 ml of water was added to the reaction mixture and extracted with 600 ml of toluene. The organic layer was washed three times with a saturated aqueous solution of sodium carbonate and three times with water and dried over anhydrous magnesium sulfate. The solvent was distilled off under reduced pressure and the residue was subjected to a silica gel column chromatography (developing solvent: toluene) to give 5.71 g of crude 1-ethenyl-trans-4-(trans-4-(trans-4-((E)-3-pentenyl)-cyclohexyl)cyclohexyl)cyclohexane. Recrystallization from a mixed solvent of ethyl acetate/heptane (3/7) gave 4.47 g (Yield, 14.5%) of the title compound. MS: m/e=342 (M$^+$)

EXAMPLE 7

Preparation of 2-((E)-3-pentenyl)-5-(trans-4-(trans-4-propylcyclohexyl)cyclohexyl-1,3-dioxane (Compound No. 127 of formula (I) wherein $R_1$ is $C_3H_7$, the rings $A_1$ and $A_2$ are trans-1,4-cyclohexylene groups, $A_3$ is 1,3-dioxane, m is 2, and $R_2$ is $CH_3$)

A mixture of 20.00 g (84.6 mmol) of trans-4-(trans-4-propylcyclohexyl)cyclohexyl carbaldehyde, 18.30 g (127 mmol) of 2-((E)-3-pentenyl)-1,3-propylene glycol and 4.15 g (4.23 mmol) of sulfuric acid in 500 ml of toluene was heated under reflux for 3 hours while azeotropically dehydrating. After allowing to cool, the reaction mixture was washed three times with a saturated aqueous solution of sodium carbonate and three times with water and dried over anhydrous sodium sulfate. The solvent was distilled off under reduced pressure to give crude 2-((E)-3-pentenyl)-5-(trans-4-(trans-4-propylcyclo-hexyl)cyclohexyl)-1,3-dioxane. Recrystallization from heptane gave 20.5 g (Yield, 66.7%) of the title compound. MS: m/e=362 (M$^+$)

EXAMPLE 8

Preparation of 1-(3-butenyl)-trans-4-(trans-4-(trans-4-ethenylcyclohexyl)cyclohexyl)cyclohexane (Compound No. 421 of formula (I) wherein $R_1$ is an ethenyl group, the rings $A_1$, $A_2$ and $A_3$ are trans-1,4-cyclohexylene groups, m is 2, and $R_2$ is H)

A mixture of 645 g (1420 mmol) of 2-(1,3-dioxane-2-yl) ethyltriphenylphosphonium bromide and 6.5 liters of THF was cooled to −50° C. To this mixture was added 147 g (1310 mmol) of t-BuOK and the resulting mixture was stirred for one hour. To this mixture was added dropwise a solution of 350 g (1090 mmol) of trans-4-(trans-4-(4-oxocyclohexyl)-cyclohexyl)chclohexane carboxylic acid methyl in 3.0 liters of THF, while maintaining a temperature at below −50° C. After the dropwise addition, the reaction temperature was gradually allowed to rise up to room temperature and the mixture was stirred for further 5 hours. After the reaction was completed by adding 1.0 liter of water, the reaction mixture was filtered through Celite, the solvent was distilled off under reduced pressure and the filtrate was extracted with 3.0 liters of toluene. The organic layer was washed three times with 1.0 liter portions of water and dried over anhydrous magnesium sulfate. The solvent was distilled off under reduced pressure and the residue was subjected to a silica gel column chromatography (a developing solvent: mixed solution of ethyl acetate/toluene (3/17)) to give 328 g of crude trans-4-(trans-4-(4-(2-(1,3-dioxane-2-yl)ethenyl)cyclohexyl)cyclohexyl)cyclohexane carboxylic acid methyl ester.

To 328 g (784 mmol) of the crude porduct dissolved in 3.0 liters of a mixed solvent of toluene/solmix (1/1) were added 16.4 g of 5% by weight of palladium/carbon catalyst and the mixture was stirred at room temperature for 6 hours under a hydrogen pressure of 1–2 kg/cm$^2$. After filtering off the catalyst, the solvent was distilled off under reduced pressure. The residue was subjected to a silca gel column chromatography (developing solvent: ethyl acetate). Recrystallization from a mixed solution of ethyl acetate/toluene (7/1) gave 140 g of trans-4-(trans-4-(trans-4-(2-(1,3-dioxane-2-yl)ethyl)cyclohexyl)cyclohexyl)-cyclohexane carboxylic acid methyl ester.

To 140 g (333 mmol) of trans-4-(trans-4-(trans-4-(2-(1,3-dioxane-2-yl)ethyl)cyclohexyl)cyclohexyl)cyclohexane carboxylic acid methyl ester dissolved in 1.5 liters of toluene were added 153 g (3330 mmol) of formic acid and the mixture was heated under reflux for one hour. The reaction solution was washed three times with 500 ml of an aqueous saturated sodium carbonate and then with 750 ml of water, and dried over anhydorus magnesium sulfate. Distilling off the solvent under reduced pressure gave 90.0 g of crude trans-4-(trans-4-(trans-4-(2-formylethyl)cyclohexyl)-cyclohexyl)cyclohexane carboxylic acid methyl ester.

A mixture of 130 g (322 mmol) of methyltriphenylphosphonium iodide and 1.3 liters of THF was cooled to −50° C. To this mixture was added 33.4 g (110 mmol) of t-BuOK and the resulting mixture was stirred for one hour. To this mixture was added dropwise, while maintaining a temperature at below −50° C., a solution of 90.0 g (248 mmol) of crude trans-4-(trans-4-(trans-4-(2-formylethyl)-cyclohexyl) cyclohexyl)cyclohexane carboxylic acid methyl ester in 900 ml of THF. After the dropwise addition, the temperature of the reaction solution was gradually allowed to rise up to room temperature and the mixture was stirred for further 5 hours. After the reaction was completed by adding 500 ml of water, the reaction mixture was filtered through Celite, the solvent was distilled off under reduced pressure and the filtrate was extracted with 1.0 liter of toluene. The organic layer was washed three times with 500 ml of water and dried over anhydrous magnesium sulfate. The solvent was distilled off under reduced pressure and the residue was subjected to a silica gel column chromatography (a developing solvent: toluene) to give 40.0 g of crude trans-4-(trans-4-(trans-4-(3-butenyl)cyclohexyl)cyclohexyl)-cyclohexane carboxylic acid methyl ester.

40.0 g (110 mmol) of the crude product was dissolved in 1.5 liters of toluene and the solution was cooled to −50° C. To this solution was added dropwise 111 ml (111 mmol) of DIBAL (1.0M solution of toluene), while maintaining a temperature at below −50° C. and the resulting mixture was stirred at the same temperature for 3 hours. After the reaction was completed by adding 500 ml of water, the reaction mixture was filtered through Celite. The organic layer was washed three times with 500 ml of water and dried over anhydrous magnesium sulfate. The solvent was distilled off under reduced pressure and the residue was subjected to a silica gel column chromatography (a developing solvent: chloroform) to give 27.6 g of crude trans-4-(trans-4-(trans-4-(3-butenyl)cyclohexyl)cyclohexyl)-cyclohexyl carbaldehyde.

A mixture of 43.9 g (109 mmol) of methyltriphenylphosphonium iodide and 500 ml of THF was cooled to −50° C.

To this mixture was added 11.2 g (100 mmol) of t-BuOK and the resulting mixture was stirred for one hour. To this mixture was added dropwise, while maintaining a temperature at below −50° C., a solution of 27.6 g (83.5 mmol) of crude trans-4-(trans-4-(trans-4-(3-butenyl)cyclohexyl)cyclohexyl)cyclohexyl carbaldehyde in 300 ml of THF. After the dropwise addition, the reaction temperature was gradually raised to room temperature and the mixture was stirred for further 5 hours. After the reaction was completed by adding 300 ml of water, the reaction mixture was filtered through Celite, the solvent was distilled off under reduced pressure and the filtrate was extracted with 700 ml of toluene. The organic layer was washed three times with 300 ml of water and dried over anhydrous magnesium sulfate. The solvent was distilled off under reduced pressure and the residue was subjected to a silica gel column chromatography (a developing solvent: heptane) to give crude 1-(3-butenyl)-trans-4-(trans-4-(trans-4-(ethenylcyclohexyl)cyclohexyl)cyclohexane. Recrystallization of the crude product from a mixed solution of heptane/ethanol gave 8.00 g (Yield, 2.23%) of the title compound.

Phase transfer temperature: Cr below room temperature,

SB 221.3 Iso NMR: δ=0.40–2.25(34H, m), 4.70–5.25 (4H, m), 5.50–6.15(2H, m) MS: m/e=328 (M$^+$)

According to the process as described in the Examples 1–8, there can be produced Compounds No. 1 to No. 535 shown in the following table.

| | $R_1$ | $A_1$ | $A_2$ | $A_3$ | $(CH_2)_m$ | $R_2$ |
|---|---|---|---|---|---|---|
| 1 | $C_3H_7$ | ⬡ | ⬡ | ⬡ | | H |
| 2 | $C_2H_5$ | ⬡ | ⬡ | ⬡ | | H |
| 3 | $C_5H_{11}$ | ⬡ | ⬡ | ⬡ | | H |
| 4 | $C_6H_{13}$ | ⬡ | ⬡ | ⬡ | | H |
| 5 | $C_9H_{19}$ | ⬡ | ⬡ | ⬡ | | H |
| 6 | $C_2H_5$ | ⬡ | ⬡ | ⬡ | $(CH_2)_2$ | H |
| 7 | $C_3H_7$ | ⬡ | ⬡ | ⬡ | $(CH_2)_2$ | H |
| 8 | $C_5H_{11}$ | ⬡ | ⬡ | ⬡ | $(CH_2)_2$ | H |
| 9 | $C_6H_{13}$ | ⬡ | ⬡ | ⬡ | $(CH_2)_2$ | H |
| 10 | $C_9H_{19}$ | ⬡ | ⬡ | ⬡ | $(CH_2)_2$ | H |
| 11 | $C_2H_5$ | ⬡ | ⬡ | ⬡ | $(CH_2)_5$ | H |

5,709,820

-continued

| R₁ | A₁ | A₂ | A₃ | (CH₂)ₘ | R₂ |
|---|---|---|---|---|---|
| 12 C₃H₇ | ⬡ | ⬡ | ⬡ | (CH₂)₅ | H |
| 13 C₅H₁₁ | ⬡ | ⬡ | ⬡ | (CH₂)₅ | H |
| 14 C₆H₁₃ | ⬡ | ⬡ | ⬡ | (CH₂)₅ | H |
| 15 C₉H₁₉ | ⬡ | ⬡ | ⬡ | (CH₂)₅ | H |
| 16 C₃H₇ | dioxane | ⬡ | ⬡ |  | H |
| 17 C₅H₁₁ | dioxane | ⬡ | ⬡ |  | H |
| 18 C₃H₇ | dioxane | ⬡ | ⬡ | CH₂ | H |
| 19 C₅H₁₁ | dioxane | ⬡ | ⬡ | CH₂ | H |
| 20 C₂H₅ | ⬡ | dioxane | ⬡ |  | H |
| 21 C₃H₇ | ⬡ | dioxane | ⬡ |  | H |
| 22 C₂H₅ | ⬡ | dioxane | ⬡ | (CH₂)₄ | H |
| 23 C₃H₇ | ⬡ | dioxane | ⬡ | (CH₂)₄ | H |
| 24 C₃H₇ | ⬡ | ⬡ | dioxane |  | H |

-continued
| R₁ | A₁ | A₂ | A₃ | (CH₂)ₘ | R₂ |
|---|---|---|---|---|---|
| 25 C₅H₁₁ |  |  |  | | H |
| 26 C₃H₇ |  |  |  | (CH₂)₄ | H |
| 27 C₅H₁₁ |  |  |  | (CH₂)₄ | H |
| 28 C₂H₅ |  |  |  | | H |
| 29 C₃H₇ |  |  |  | | H |
| 30 C₂H₅ |  |  |  | (CH₂)₃ | H |
| 31 C₃H₇ |  |  |  | (CH₂)₃ | H |
| 32 C₃H₇ |  |  |  | | H |
| 33 C₄H₉ |  |  |  | | H |
| 34 C₃H₇ |  |  |  | (CH₂)₂ | H |
| 35 C₄H₉ |  |  |  | (CH₂)₂ | H |
| 36 C₃H₇ |  |  |  | | H |
| 37 C₅H₁₁ |  |  |  | | H |

-continued
| | R₁ | A₁ | A₂ | A₃ | (CH₂)ₘ | R₂ |
|---|---|---|---|---|---|---|
| 38 | C₃H₇ |  |  |  O | CH₂ | H |
| 39 | C₅H₁₁ |  |  |  O | CH₂ | H |
| 40 | C₃H₅ |  S,S |  |  | | H |
| 41 | C₅H₁₁ |  S,S |  |  | | H |
| 42 | C₃H₇ |  S,S |  |  | (CH₂)₅ | H |
| 43 | C₅H₁₁ |  S,S |  |  | (CH₂)₅ | H |
| 44 | C₂H₅ |  |  S,S |  | | H |
| 45 | C₃H₇ |  |  S,S |  | | H |
| 46 | C₂H₅ |  |  S,S |  | (CH₂)₄ | H |
| 47 | C₃H₇ |  |  S,S |  | (CH₂)₄ | H |
| 48 | C₃H₇ |  |  |  S,S | | H |
| 49 | C₄H₉ |  |  |  S,S | | H |
| 50 | C₃H₇ |  |  |  S,S | (CH₂)₄ | H |

-continued

| | R₁ | A₁ | A₂ | A₃ | (CH₂)ₘ | R₂ |
|---|---|---|---|---|---|---|
| 51 | C₄H₉ | hexagon | hexagon | hexagon with S,S | (CH₂)₄ | H |
| 52 | C₃H₅ | hexagon with S | hexagon | hexagon | | H |
| 53 | C₅H₁₁ | hexagon with S | hexagon | hexagon | | H |
| 54 | C₃H₇ | hexagon with S | hexagon | hexagon | (CH₂)₂ | H |
| 55 | C₅H₁₁ | hexagon with S | hexagon | hexagon | (CH₂)₂ | H |
| 56 | C₂H₅ | hexagon | hexagon with S | hexagon | | H |
| 57 | C₃H₇ | hexagon | hexagon with S | hexagon | | H |
| 58 | C₂H₅ | hexagon | hexagon with S | hexagon | CH₂ | H |
| 59 | C₃H₇ | hexagon | hexagon with S | hexagon | CH₂ | H |
| 60 | C₃H₇ | hexagon | hexagon | hexagon with S | | H |
| 61 | C₄H₉ | hexagon | hexagon | hexagon with S | | H |
| 62 | C₃H₇ | hexagon | hexagon | hexagon with S | (CH₂)₅ | H |
| 63 | C₄H₉ | hexagon | hexagon | hexagon with S | (CH₂)₅ | H |
| 64 | C₂H₅ | hexagon | hexagon | hexagon | | CH₃ |

-continued

| | R₁ | A₁ | A₂ | A₃ | (CH₂)ₘ | R₂ |
|---|---|---|---|---|---|---|
| 65 | C₃H₇ | ⬡ | ⬡ | ⬡ | | CH₃ |
| 66 | C₅H₁₁ | ⬡ | ⬡ | ⬡ | | CH₃ |
| 67 | C₂H₅ | ⬡ | ⬡ | ⬡ | (CH₂)₂ | CH₃ |
| 68 | C₃H₇ | ⬡ | ⬡ | ⬡ | (CH₂)₂ | CH₃ |
| 69 | C₅H₁₁ | ⬡ | ⬡ | ⬡ | (CH₂)₂ | CH₃ |
| 70 | C₂H₅ | ⬡ | ⬡ | ⬡ | (CH₂)₄ | CH₃ |
| 71 | C₃H₇ | ⬡ | ⬡ | ⬡ | (CH₂)₄ | CH₃ |
| 72 | C₅H₁₁ | ⬡ | ⬡ | ⬡ | (CH₂)₄ | CH₃ |
| 73 | C₂H₅ | ⬡ | ⬡ | ⬡ | | C₃H₇ |
| 74 | C₃H₇ | ⬡ | ⬡ | ⬡ | | C₃H₇ |
| 75 | C₅H₁₁ | ⬡ | ⬡ | ⬡ | | C₃H₇ |
| 76 | C₂H₅ | ⬡ | ⬡ | ⬡ | (CH₂)₂ | C₃H₇ |
| 77 | C₃H₇ | ⬡ | ⬡ | ⬡ | (CH₂)₂ | C₃H₇ |
| 78 | C₅H₁₁ | ⬡ | ⬡ | ⬡ | (CH₂)₂ | C₃H₇ |

-continued
| | $R_1$ | $A_1$ | $A_2$ | $A_3$ | $(CH_2)_m$ | $R_2$ |
|---|---|---|---|---|---|---|
| 79 | $C_2H_5$ |  |  |  | $(CH_2)_4$ | $C_3H_7$ |
| 80 | $C_3H_7$ |  |  |  | $(CH_2)_4$ | $C_3H_7$ |
| 81 | $C_5H_{11}$ |  |  |  | $(CH_2)_4$ | $C_3H_7$ |
| 82 | $C_2H_5$ |  |  |  | | $C_4H_9$ |
| 83 | $C_3H_7$ |  |  |  | | $C_4H_9$ |
| 84 | $C_5H_{11}$ |  |  |  | | $C_4H_9$ |
| 85 | $C_2H_5$ |  |  |  | $(CH_2)_2$ | $C_4H_9$ |
| 86 | $C_3H_7$ |  |  |  | $(CH_2)_2$ | $C_4H_9$ |
| 87 | $C_5H_{11}$ |  |  |  | $(CH_2)_2$ | $C_4H_9$ |
| 88 | $C_2H_5$ |  |  |  | $(CH_2)_4$ | $C_4H_9$ |
| 89 | $C_3H_7$ |  |  |  | $(CH_2)_4$ | $C_4H_9$ |
| 90 | $C_5H_{11}$ |  |  |  | $(CH_2)_4$ | $C_4H_9$ |
| 91 | $C_2H_5$ |  |  |  | | $C_5H_{11}$ |
| 92 | $C_3H_7$ |  |  |  | | $C_5H_{11}$ |
| 93 | $C_5H_{11}$ |  |  |  | | $C_5H_{11}$ |

-continued
| | R₁ | A₁ | A₂ | A₃ | (CH₂)ₘ | R₂ |
|---|---|---|---|---|---|---|
| 94 | C₂H₅ |  |  |  | (CH₂)₂ | C₅H₁₁ |
| 95 | C₃H₇ |  |  |  | (CH₂)₂ | C₅H₁₁ |
| 96 | C₅H₁₁ |  |  |  | (CH₂)₂ | C₅H₁₁ |
| 97 | C₂H₅ |  |  |  | (CH₂)₄ | C₅H₁₁ |
| 98 | C₃H₇ |  |  |  | (CH₂)₄ | C₅H₁₁ |
| 99 | C₅H₁₁ |  |  |  | (CH₂)₄ | C₅H₁₁ |
| 100 | C₂H₅ |  |  |  | | C₆H₁₃ |
| 101 | C₃H₇ |  |  |  | | C₆H₁₃ |
| 102 | C₅H₁₁ |  |  |  | | C₆H₁₃ |
| 103 | C₂H₅ |  |  |  | (CH₂)₂ | C₆H₁₃ |
| 104 | C₃H₇ |  |  |  | (CH₂)₂ | C₆H₁₃ |
| 105 | C₅H₁₁ |  |  |  | (CH₂)₂ | C₆H₁₃ |
| 106 | C₂H₅ |  |  |  | (CH₂)₄ | C₆H₁₃ |
| 107 | C₃H₇ |  |  |  | (CH₂)₄ | C₆H₁₃ |

-continued
| R₁ | A₁ | A₂ | A₃ | (CH₂)ₘ | R₂ |
|---|---|---|---|---|---|
| 108 C₅H₁₁ |  |  |  | (CH₂)₄ | C₆H₁₃ |
| 109 C₃H₇ | 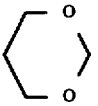 | 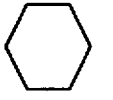 | 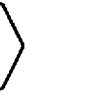 |  | C₂H₅ |
| 110 C₅H₁₁ | 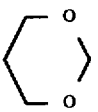 |  |  |  | C₂H₅ |
| 111 C₃H₇ |  |  |  | (CH₂)₂ | C₂H₅ |
| 112 C₅H₁₁ |  |  |  | (CH₂)₂ | C₂H₅ |
| 113 C₃H₇ |  |  |  |  | C₃H₇ |
| 114 C₅H₁₁ | 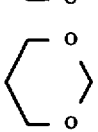 | 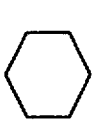 | 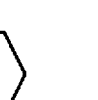 |  | C₃H₇ |
| 115 C₃H₇ |  |  |  | (CH₂)₂ | C₃H₇ |
| 116 C₅H₁₁ |  |  |  | (CH₂)₂ | C₃H₇ |
| 117 C₅H₁₁ |  | 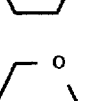 |  |  | C₄H₉ |
| 118 C₅H₁₁ |  |  |  |  | C₄H₉ |
| 119 C₃H₇ | 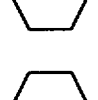 | 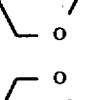 | 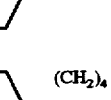 | (CH₂)₄ | C₄H₉ |
| 120 C₅H₁₁ |  |  |  | (CH₂)₄ | C₄H₉ |

-continued
| | R₁ | A₁ | A₂ | A₃ | (CH₂)ₘ | R₂ |
|---|---|---|---|---|---|---|
| 121 | C₅H₁₁ |  | 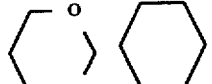 |  | | C₅H₁₁ |
| 122 | C₅H₁₁ |  |  |  | | C₅H₁₁ |
| 123 | C₃H₇ |  | 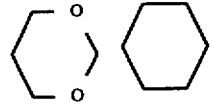 |  | (CH₂)₄ | C₅H₁₁ |
| 124 | C₅H₁₁ |  |  |  | (CH₂)₄ | C₅H₁₁ |
| 125 | C₃H₇ |  |  |  | | CH₃ |
| 126 | C₅H₁₁ |  |  |  | | CH₃ |
| 127 | C₃H₇ |  |  |  | (CH₂)₂ | CH₃ |
| 128 | C₅H₁₁ |  |  |  | (CH₂)₂ | CH₃ |
| 129 | C₃H₇ |  |  |  | | C₆H₁₃ |
| 130 | C₅H₁₁ |  |  |  | | C₆H₁₃ |
| 131 | C₃H₇ |  |  |  | (CH₂)₂ | C₆H₁₃ |
| 132 | C₅H₁₁ |  |  |  | (CH₂)₂ | C₆H₁₃ |
| 133 | C₃H₇ |  |  |  | | C₅H₁₁ |

-continued

| | R₁ | A₁ | A₂ | A₃ | (CH₂)ₘ | R₂ |
|---|---|---|---|---|---|---|
| 134 | C₅H₁₁ | ⬡-O | ⬡ | ⬡ | | C₅H₁₁ |
| 135 | C₃H₇ | ⬡-O | ⬡ | ⬡ | (CH₂)₄ | C₅H₁₁ |
| 136 | C₅H₁₁ | ⬡-O | ⬡ | ⬡ | (CH₂)₄ | C₅H₁₁ |
| 137 | C₃H₇ | ⬡-O | ⬡ | ⬡ | | C₈H₁₇ |
| 138 | C₅H₁₁ | ⬡-O | ⬡ | ⬡ | | C₈H₁₇ |
| 139 | C₃H₇ | ⬡-O | ⬡ | ⬡ | (CH₂)₄ | C₈H₁₇ |
| 140 | C₅H₁₁ | ⬡-O | ⬡ | ⬡ | (CH₂)₄ | C₈H₁₇ |
| 141 | C₃H₇ | ⬡ | ⬡-O | ⬡ | | C₃H₇ |
| 142 | C₅H₁₁ | ⬡ | ⬡-O | ⬡ | | C₃H₇ |
| 143 | C₃H₇ | ⬡ | ⬡-O | ⬡ | (CH₂)₂ | C₃H₇ |
| 144 | C₅H₁₁ | ⬡ | ⬡-O | ⬡ | (CH₂)₂ | C₃H₇ |
| 145 | C₃H₇ | ⬡ | ⬡-O | ⬡ | | C₉H₁₉ |
| 146 | C₅H₁₁ | ⬡ | ⬡-O | ⬡ | | C₉H₁₉ |
| 147 | C₃H₇ | ⬡ | ⬡-O | ⬡ | (CH₂)₂ | C₉H₁₉ |

-continued

| R₁ | A₁ | A₂ | A₃ | (CH₂)ₘ | R₂ |
|---|---|---|---|---|---|
| 148 C₅H₁₁ | ⬡ | ⬡O | ⬡ | (CH₂)₂ | C₉H₁₉ |
| 149 C₃H₇ | ⬡ | ⬡ | ⬡O | | C₅H₁₁ |
| 150 C₅H₁₁ | ⬡ | ⬡ | ⬡O | | C₅H₁₁ |
| 151 C₃H₇ | ⬡ | ⬡ | ⬡O | (CH₂)₄ | C₅H₁₁ |
| 152 C₅H₁₁ | ⬡ | ⬡ | ⬡O | (CH₂)₄ | C₅H₁₁ |
| 153 C₃H₇ | ⬡ | ⬡ | ⬡O | | C₁₀H₂₁ |
| 154 C₅H₁₁ | ⬡ | ⬡ | ⬡O | | C₁₀H₂₁ |
| 155 C₃H₇ | ⬡ | ⬡ | ⬡O | (CH₂)₄ | C₁₀H₂₁ |
| 156 C₅H₁₁ | ⬡ | ⬡ | ⬡O | (CH₂)₄ | C₁₀H₂₁ |
| 157 C₃H₇ | ⬡(S,S) | ⬡ | ⬡ | | C₃H₇ |
| 158 C₅H₁₁ | ⬡(S,S) | ⬡ | ⬡ | | C₃H₇ |
| 159 C₃H₇ | ⬡(S,S) | ⬡ | ⬡ | (CH₂)₂ | C₃H₇ |
| 160 C₅H₁₁ | ⬡(S,S) | ⬡ | ⬡ | (CH₂)₂ | C₃H₇ |

-continued

| R₁ | A₁ | A₂ | A₃ | (CH₂)ₘ | R₂ |
|---|---|---|---|---|---|
| 161 C₃H₇ | dithiane | benzene | benzene | | C₄H₉ |
| 162 C₅H₁₁ | dithiane | benzene | benzene | | C₄H₉ |
| 163 C₃H₇ | dithiane | benzene | benzene | (CH₂)₂ | C₄H₉ |
| 164 C₅H₁₁ | dithiane | benzene | benzene | (CH₂)₂ | C₄H₉ |
| 165 C₃H₇ | benzene | dithiane | benzene | | C₂H₅ |
| 166 C₅H₁₁ | benzene | dithiane | benzene | | C₂H₅ |
| 167 C₃H₇ | benzene | dithiane | benzene | (CH₂)₄ | C₂H₅ |
| 168 C₅H₁₁ | benzene | dithiane | benzene | (CH₂)₄ | C₂H₅ |
| 169 C₃H₇ | benzene | dithiane | benzene | | C₅H₁₁ |
| 170 C₅H₁₁ | benzene | dithiane | benzene | | C₅H₁₁ |
| 171 C₃H₇ | benzene | dithiane | benzene | (CH₂)₄ | C₅H₁₁ |
| 172 C₅H₁₁ | benzene | dithiane | benzene | (CH₂)₄ | C₅H₁₁ |
| 173 C₃H₇ | benzene | benzene | dithiane | | C₃H₇ |

-continued

| | R₁ | A₁ | A₂ | A₃ | (CH₂)ₘ | R₂ |
|---|---|---|---|---|---|---|
| 174 | C₅H₁₁ | ⬡ | ⬡ | S-S ring | | C₃H₇ |
| 175 | C₃H₇ | ⬡ | ⬡ | S-S ring | (CH₂)₂ | C₃H₇ |
| 176 | C₅H₁₁ | ⬡ | ⬡ | S-S ring | (CH₂)₂ | C₃H₇ |
| 177 | C₃H₇ | ⬡ | ⬡ | S-S ring | | C₈H₁₇ |
| 178 | C₅H₁₁ | ⬡ | ⬡ | S-S ring | | C₈H₁₇ |
| 179 | C₃H₇ | ⬡ | ⬡ | S-S ring | (CH₂)₂ | C₈H₁₇ |
| 180 | C₅H₁₁ | ⬡ | ⬡ | S-S ring | (CH₂)₂ | C₈H₁₇ |
| 181 | C₃H₇ | S-ring | ⬡ | ⬡ | | CH₃ |
| 182 | C₅H₁₁ | S-ring | ⬡ | ⬡ | | CH₃ |
| 183 | C₃H₇ | S-ring | ⬡ | ⬡ | (CH₂)₄ | CH₃ |
| 184 | C₅H₁₁ | S-ring | ⬡ | ⬡ | (CH₂)₄ | CH₃ |
| 185 | C₃H₇ | S-ring | ⬡ | ⬡ | | C₅H₁₁ |
| 186 | C₃H₇ | S-ring | ⬡ | ⬡ | | C₅H₁₁ |

-continued

| | R₁ | A₁ | A₂ | A₃ | (CH₂)ₘ | R₂ |
|---|---|---|---|---|---|---|
| 187 | C₃H₇ | ⬡-S | ⬡ | ⬡ | (CH₂)₄ | C₅H₁₁ |
| 188 | C₅H₁₁ | ⬡-S | ⬡ | ⬡ | (CH₂)₄ | C₅H₁₁ |
| 189 | C₃H₇ | ⬡ | ⬡-S | ⬡ | | C₃H₇ |
| 190 | C₅H₁₁ | ⬡ | ⬡-S | ⬡ | | C₃H₇ |
| 191 | C₃H₇ | ⬡ | ⬡-S | ⬡ | (CH₂)₂ | C₃H₇ |
| 192 | C₅H₁₁ | ⬡ | ⬡-S | ⬡ | (CH₂)₂ | C₃H₇ |
| 193 | C₃H₇ | ⬡ | ⬡-S | ⬡ | | C₇H₁₅ |
| 194 | C₅H₁₁ | ⬡ | ⬡-S | ⬡ | | C₇H₁₅ |
| 195 | C₃H₇ | ⬡ | ⬡-S | ⬡ | (CH₂)₂ | C₇H₁₅ |
| 196 | C₅H₁₁ | ⬡ | ⬡-S | ⬡ | (CH₂)₂ | C₇H₁₅ |
| 197 | C₃H₇ | ⬡ | ⬡ | ⬡-S | | C₄H₉ |
| 198 | C₅H₁₁ | ⬡ | ⬡ | ⬡-S | | C₄H₉ |
| 199 | C₃H₇ | ⬡ | ⬡ | ⬡-S | (CH₂)₄ | C₄H₉ |
| 200 | C₅H₁₁ | ⬡ | ⬡ | ⬡-S | (CH₂)₄ | C₄H₉ |

-continued
| | $R_1$ | $A_1$ | $A_2$ | $A_3$ | $(CH_2)_m$ | $R_2$ |
|---|---|---|---|---|---|---|
| 201 | $C_3H_7$ |  |  | S | | $C_5H_{11}$ |
| 202 | $C_5H_{11}$ |  |  | S | | $C_5H_{11}$ |
| 203 | $C_3H_7$ |  |  | S | $(CH_2)_4$ | $C_5H_{11}$ |
| 204 | $C_5H_{11}$ |  |  | S | $(CH_2)_4$ | $C_5H_{11}$ |
| 205 | $C_2H_5$ |  |  |  | $OCH_2$ | H |
| 206 | $C_3H_7$ |  |  |  | $OCH_2$ | H |
| 207 | $C_5H_{11}$ |  |  |  | $OCH_2$ | H |
| 208 | $C_6H_{13}$ |  |  |  | $OCH_2$ | H |
| 209 | $C_9H_{19}$ |  |  |  | $OCH_2$ | H |
| 210 | $C_2H_5$ |  |  |  | $OC_2H_4$ | H |
| 211 | $C_3H_7$ |  |  |  | $OC_2H_4$ | H |
| 212 | $C_5H_{11}$ |  |  |  | $OC_2H_4$ | H |
| 213 | $C_6H_{13}$ |  |  |  | $OC_2H_4$ | H |
| 214 | $C_9H_{19}$ |  |  |  | $OC_2H_4$ | H |

-continued
| R₁ | A₁ | A₂ | A₃ | (CH₂)ₘ | R₂ |
|---|---|---|---|---|---|
| 215 C₂H₅ |  |  |  | OC₃H₆ | H |
| 216 C₃H₇ |  |  |  | OC₃H₆ | H |
| 217 C₅H₁₁ |  |  |  | OC₃H₆ | H |
| 218 C₆H₁₃ |  |  |  | OC₃H₆ | H |
| 219 C₉H₁₉ |  |  |  | OC₃H₆ | H |
| 220 C₂H₅ |  |  |  | CH₂OC₂H₄ | H |
| 221 C₃H₇ |  |  |  | CH₂OC₂H₄ | H |
| 222 C₅H₁₁ |  |  |  | CH₂OC₂H₄ | H |
| 223 C₆H₁₃ |  |  |  | CH₂OC₂H₄ | H |
| 224 C₉H₁₉ |  |  |  | CH₂OC₂H₄ | H |
| 225 C₂H₅ |  |  |  | C₂H₄OCH₂ | H |
| 226 C₃H₇ |  |  |  | C₂H₄OCH₂ | H |
| 227 C₅H₁₁ |  |  |  | C₂H₄OCH₂ | H |
| 228 C₆H₁₃ |  |  |  | C₂H₄OCH₂ | H |
| 229 C₉H₁₉ |  |  |  | C₂H₄OCH₂ | H |

-continued

| | $R_1$ | $A_1$ | $A_2$ | $A_3$ | $(CH_2)_m$ | $R_2$ |
|---|---|---|---|---|---|---|
| 230 | $C_2H_5$ | dioxane | phenyl | phenyl | $OCH_2$ | H |
| 231 | $C_3H_7$ | dioxane | phenyl | phenyl | $OCH_2$ | H |
| 232 | $C_2H_5$ | dioxane | phenyl | phenyl | $CH_2OC_2H_4$ | H |
| 233 | $C_3H_7$ | dioxane | phenyl | phenyl | $CH_2OC_2H_4$ | H |
| 234 | $C_3H_7$ | phenyl | dioxane | phenyl | $OCH_2$ | H |
| 235 | $C_5H_{11}$ | phenyl | dioxane | phenyl | $OCH_2$ | H |
| 236 | $C_3H_7$ | phenyl | dioxane | phenyl | $CH_2OCH_2$ | H |
| 237 | $C_5H_{11}$ | phenyl | dioxane | phenyl | $CH_2OCH_2$ | H |
| 238 | $C_2H_5$ | phenyl | phenyl | dioxane | $OCH_2$ | H |
| 239 | $C_3H_7$ | phenyl | phenyl | dioxane | $OCH_2$ | H |
| 240 | $C_2H_5$ | phenyl | phenyl | dioxane | $OC_3H_6$ | H |
| 241 | $C_3H_7$ | phenyl | phenyl | dioxane | $OC_3H_6$ | H |
| 242 | $C_3H_7$ | pyran | phenyl | phenyl | $OCH_2$ | H |

-continued

| | R₁ | A₁ | A₂ | A₃ | (CH₂)ₘ | R₂ |
|---|---|---|---|---|---|---|
| 243 | C₅H₁₁ | pyran (O) | cyclohexane | cyclohexane | OCH₂ | H |
| 244 | C₃H₇ | pyran (O) | cyclohexane | cyclohexane | C₂H₄OCH₂ | H |
| 245 | C₅H₁₁ | pyran (O) | cyclohexane | cyclohexane | C₂H₄OCH₂ | H |
| 246 | C₂H₅ | cyclohexane | pyran (O) | cyclohexane | OCH₂ | H |
| 247 | C₅H₁₁ | cyclohexane | pyran (O) | cyclohexane | OCH₂ | H |
| 248 | C₂H₅ | cyclohexane | pyran (O) | cyclohexane | OC₂H₄ | H |
| 249 | C₅H₁₁ | cyclohexane | pyran (O) | cyclohexane | OC₂H₄ | H |
| 250 | C₃H₇ | cyclohexane | cyclohexane | pyran (O) | OCH₂ | H |
| 251 | C₅H₁₁ | cyclohexane | cyclohexane | pyran (O) | OCH₂ | H |
| 252 | C₃H₇ | cyclohexane | cyclohexane | pyran (O) | OC₃H₆ | H |
| 253 | C₅H₁₁ | cyclohexane | cyclohexane | pyran (O) | OC₃H₆ | H |
| 254 | C₃H₇ | dithiane (S,S) | cyclohexane | cyclohexane | OCH₂ | H |
| 255 | C₅H₁₁ | dithiane (S,S) | cyclohexane | cyclohexane | OCH₂ | H |

-continued

| | $R_1$ | $A_1$ | $A_2$ | $A_3$ | $(CH_2)_m$ | $R_2$ |
|---|---|---|---|---|---|---|
| 256 | $C_3H_7$ | dithiolane | hexagon | hexagon | $OC_3H_6$ | H |
| 257 | $C_5H_{11}$ | dithiolane | hexagon | hexagon | $OC_3H_6$ | H |
| 258 | $C_2H_5$ | hexagon | dithiolane | hexagon | $OCH_2$ | H |
| 259 | $C_3H_7$ | hexagon | dithiolane | hexagon | $OCH_2$ | H |
| 260 | $C_2H_5$ | hexagon | dithiolane | hexagon | $C_2H_4OCH_2$ | H |
| 261 | $C_3H_7$ | hexagon | dithiolane | hexagon | $C_2H_4OCH_2$ | H |
| 262 | $C_3H_7$ | hexagon | hexagon | dithiolane | $OCH_2$ | H |
| 263 | $C_5H_{11}$ | hexagon | hexagon | dithiolane | $OCH_2$ | H |
| 264 | $C_3H_7$ | hexagon | hexagon | dithiolane | $CH_2OC_2H_4$ | H |
| 265 | $C_5H_{11}$ | hexagon | hexagon | dithiolane | $CH_2OC_2H_4$ | H |
| 266 | $C_2H_5$ | thiahexagon | hexagon | hexagon | $OCH_2$ | H |
| 267 | $C_3H_7$ | thiahexagon | hexagon | hexagon | $OCH_2$ | H |
| 268 | $C_2H_5$ | thiahexagon | hexagon | hexagon | $OC_2H_4$ | H |

-continued

| | $R_1$ | $A_1$ | $A_2$ | $A_3$ | $(CH_2)_m$ | $R_2$ |
|---|---|---|---|---|---|---|
| 269 | $C_3H_7$ | ⬡−S | ⬡ | ⬡ | $OC_2H_4$ | H |
| 270 | $C_3H_7$ | ⬡ | ⬡−S | ⬡ | $OCH_2$ | H |
| 271 | $C_5H_{11}$ | ⬡ | ⬡−S | ⬡ | $OCH_2$ | H |
| 272 | $C_3H_7$ | ⬡ | ⬡−S | ⬡ | $OC_3H_6$ | H |
| 273 | $C_5H_{11}$ | ⬡ | ⬡−S | ⬡ | $OC_3H_6$ | H |
| 274 | $C_2H_5$ | ⬡ | ⬡ | ⬡−S | $OCH_2$ | H |
| 275 | $C_3H_7$ | ⬡ | ⬡ | ⬡−S | $OCH_2$ | H |
| 276 | $C_2H_5$ | ⬡ | ⬡ | ⬡−S | $C_2H_4OCH_2$ | H |
| 277 | $C_3H_7$ | ⬡ | ⬡ | ⬡−S | $C_2H_4OCH_2$ | H |
| 278 | $C_2H_5$ | ⬡ | ⬡ | ⬡ | $OCH_2$ | $CH_3$ |
| 279 | $C_3H_7$ | ⬡ | ⬡ | ⬡ | $OCH_2$ | $CH_3$ |
| 280 | $C_5H_{11}$ | ⬡ | ⬡ | ⬡ | $OCH_2$ | $CH_3$ |
| 281 | $C_2H_5$ | ⬡ | ⬡ | ⬡ | $CH_2OCH_2$ | $CH_3$ |
| 282 | $C_3H_7$ | ⬡ | ⬡ | ⬡ | $CH_2OCH_2$ | $CH_3$ |

-continued
| R₁ | A₁ | A₂ | A₃ | (CH₂)ₘ | R₂ |
|---|---|---|---|---|---|
| 283 C₅H₁₁ |  |  |  | CH₂OCH₂ | CH₃ |
| 284 C₂H₅ |  |  |  | OC₃H₆ | CH₃ |
| 285 C₃H₇ |  |  |  | OC₃H₆ | CH₃ |
| 286 C₅H₁₁ |  |  |  | OC₃H₆ | CH₃ |
| 287 C₂H₅ |  |  |  | OCH₂ | C₃H₇ |
| 288 C₃H₇ |  |  |  | OCH₂ | C₃H₇ |
| 289 C₅H₁₁ |  |  |  | OCH₂ | C₃H₇ |
| 290 C₂H₅ |  |  |  | CH₂OCH₂ | C₃H₇ |
| 291 C₃H₇ |  |  |  | CH₂OCH₂ | C₃H₇ |
| 292 C₅H₁₁ |  |  |  | CH₂OCH₂ | C₃H₇ |
| 293 C₂H₅ |  |  |  | OC₃H₆ | C₃H₇ |
| 294 C₃H₇ |  |  |  | OC₃H₆ | C₃H₇ |
| 295 C₅H₁₁ |  |  |  | OC₃H₆ | C₃H₇ |
| 296 C₂H₅ |  |  |  | OCH₂ | C₄H₉ |
| 297 C₃H₇ |  |  |  | OCH₂ | C₄H₉ |

-continued
| R₁ | A₁ | A₂ | A₃ | (CH₂)ₘ | R₂ |
|---|---|---|---|---|---|
| 298 C₅H₁₁ |  |  |  | OCH₂ | C₄H₉ |
| 299 C₂H₅ |  |  |  | CH₂OCH₂ | C₄H₉ |
| 300 C₃H₇ |  |  |  | CH₂OCH₂ | C₄H₉ |
| 301 C₅H₁₁ |  |  |  | CH₂OCH₂ | C₄H₉ |
| 302 C₂H₅ |  |  |  | OC₃H₆ | C₄H₉ |
| 303 C₃H₇ |  |  |  | OC₃H₆ | C₄H₉ |
| 304 C₅H₁₁ |  |  |  | OC₃H₆ | C₄H₉ |
| 305 C₂H₅ |  |  |  | OCH₂ | C₅H₁₁ |
| 306 C₃H₇ |  |  |  | OCH₂ | C₅H₁₁ |
| 307 C₅H₁₁ |  |  |  | OCH₂ | C₅H₁₁ |
| 308 C₂H₅ |  |  |  | CH₂OCH₂ | C₅H₁₁ |
| 309 C₃H₇ |  |  |  | CH₂OCH₂ | C₅H₁₁ |
| 310 C₅H₁₁ |  |  |  | CH₂OCH₂ | C₅H₁₁ |
| 311 C₂H₅ |  |  |  | OC₃H₆ | C₅H₁₁ |

-continued

| R₁ | A₁ | A₂ | A₃ | (CH₂)ₘ | R₂ |
|---|---|---|---|---|---|
| 312 C₃H₇ | ⬡ | ⬡ | ⬡ | OC₃H₆ | C₅H₁₁ |
| 313 C₅H₁₁ | ⬡ | ⬡ | ⬡ | OC₃H₆ | C₅H₁₁ |
| 314 C₂H₅ | ⬡ | ⬡ | ⬡ | OCH₂ | C₆H₁₃ |
| 315 C₃H₇ | ⬡ | ⬡ | ⬡ | OCH₂ | C₆H₁₃ |
| 316 C₅H₁₁ | ⬡ | ⬡ | ⬡ | OCH₂ | C₆H₁₃ |
| 317 C₂H₅ | ⬡ | ⬡ | ⬡ | CH₂OCH₂ | C₆H₁₃ |
| 318 C₃H₇ | ⬡ | ⬡ | ⬡ | CH₂OCH₂ | C₆H₁₃ |
| 319 C₅H₁₁ | ⬡ | ⬡ | ⬡ | CH₂OCH₂ | C₆H₁₃ |
| 320 C₂H₅ | ⬡ | ⬡ | ⬡ | OC₃H₆ | C₆H₁₃ |
| 321 C₃H₇ | ⬡ | ⬡ | ⬡ | OC₃H₆ | C₆H₁₃ |
| 322 C₅H₁₁ | ⬡ | ⬡ | ⬡ | OC₃H₆ | C₆H₁₃ |
| 323 C₃H₇ | dioxane | ⬡ | ⬡ | OCH₂ | C₃H₇ |
| 324 C₅H₁₁ | dioxane | ⬡ | ⬡ | OCH₂ | C₃H₇ |
| 325 C₃H₇ | dioxane | ⬡ | ⬡ | C₂H₄OCH₂ | C₃H₇ |

-continued

| R₁ | A₁ | A₂ | A₃ | (CH₂)ₘ | R₂ |
|---|---|---|---|---|---|
| 326 C₅H₁₁ | dioxane | hexagon | hexagon | C₂H₄OCH₂ | C₃H₇ |
| 327 C₃H₇ | dioxane | hexagon | hexagon | OCH₂ | C₆H₁₃ |
| 328 C₅H₁₁ | dioxane | hexagon | hexagon | OCH₂ | C₆H₁₃ |
| 329 C₃H₇ | dioxane | hexagon | hexagon | C₂H₄OCH₂ | C₆H₁₃ |
| 330 C₅H₁₁ | dioxane | hexagon | hexagon | C₂H₄OCH₂ | C₆H₁₃ |
| 331 C₃H₇ | hexagon | dioxane | hexagon | OCH₂ | C₅H₁₁ |
| 332 C₅H₁₁ | hexagon | dioxane | hexagon | OCH₂ | C₅H₁₁ |
| 333 C₃H₇ | hexagon | dioxane | hexagon | OC₃H₁₃ | C₅H₁₁ |
| 334 C₅H₁₁ | hexagon | dioxane | hexagon | OC₃H₁₃ | C₅H₁₁ |
| 335 C₃H₇ | hexagon | dioxane | hexagon | OCH₂ | C₈H₁₇ |
| 336 C₅H₁₁ | hexagon | dioxane | hexagon | OCH₂ | C₈H₁₇ |
| 337 C₃H₇ | hexagon | dioxane | hexagon | OC₃H₆ | C₈H₁₇ |
| 338 C₅H₁₁ | hexagon | dioxane | hexagon | OC₃H₆ | C₈H₁₇ |

-continued

| R₁ | A₁ | A₂ | A₃ | (CH₂)ₘ | R₂ |
|---|---|---|---|---|---|
| 339 C₃H₇ | hexagon | hexagon | dioxane | OCH₂ | C₃H₇ |
| 340 C₅H₁₁ | hexagon | hexagon | dioxane | OCH₂ | C₃H₇ |
| 341 C₃H₇ | hexagon | hexagon | dioxane | OC₂H₄ | C₃H₇ |
| 342 C₅H₁₁ | hexagon | hexagon | dioxane | OC₂H₄ | C₃H₇ |
| 343 C₃H₇ | hexagon | hexagon | dioxane | OCH₂ | C₉H₁₉ |
| 344 C₅H₁₁ | hexagon | hexagon | dioxane | OCH₂ | C₉H₁₉ |
| 345 C₃H₇ | hexagon | hexagon | dioxane | OC₂H₄ | C₉H₁₉ |
| 346 C₅H₁₁ | hexagon | hexagon | dioxane | OC₂H₄ | C₉H₁₉ |
| 347 C₃H₇ | pyran | hexagon | hexagon | OCH₂ | C₅H₁₁ |
| 348 C₅H₁₁ | pyran | hexagon | hexagon | OCH₂ | C₅H₁₁ |
| 349 C₃H₇ | pyran | hexagon | hexagon | OC₂H₄ | C₅H₁₁ |
| 350 C₅H₁₁ | pyran | hexagon | hexagon | OC₂H₄ | C₅H₁₁ |
| 351 C₃H₇ | pyran | hexagon | hexagon | OCH₂ | C₁₀H₂₁ |

-continued

| R₁ | A₁ | A₂ | A₃ | (CH₂)ₘ | R₂ |
|---|---|---|---|---|---|
| 352 C₅H₁₁ | pyran-O | cyclohexyl | cyclohexyl | OCH₂ | C₁₀H₂₁ |
| 353 C₃H₇ | pyran-O | cyclohexyl | cyclohexyl | OC₂H₄ | C₁₀H₂₁ |
| 354 C₅H₁₁ | pyran-O | cyclohexyl | cyclohexyl | OC₂H₄ | C₁₀H₂₁ |
| 355 C₃H₇ | cyclohexyl | pyran-O | cyclohexyl | OCH₂ | C₃H₇ |
| 356 C₅H₁₁ | cyclohexyl | pyran-O | cyclohexyl | OCH₂ | C₃H₇ |
| 357 C₃H₇ | cyclohexyl | pyran-O | cyclohexyl | CH₂H₄OCH₂ | C₃H₇ |
| 358 C₅H₁₁ | cyclohexyl | pyran-O | cyclohexyl | CH₂H₄OCH₂ | C₃H₇ |
| 359 C₃H₇ | cyclohexyl | pyran-O | cyclohexyl | OCH₂ | C₄H₉ |
| 360 C₅H₁₁ | cyclohexyl | pyran-O | cyclohexyl | OCH₂ | C₄H₉ |
| 361 C₃H₇ | cyclohexyl | pyran-O | cyclohexyl | CH₂H₄OCH₂ | C₄H₉ |
| 362 C₅H₁₁ | cyclohexyl | pyran-O | cyclohexyl | CH₂H₄OCH₂ | C₄H₉ |
| 363 C₃H₇ | cyclohexyl | cyclohexyl | pyran-O | OCH₂ | C₂H₅ |
| 364 C₅H₁₁ | cyclohexyl | cyclohexyl | pyran-O | OCH₂ | C₂H₅ |
| 365 C₃H₇ | cyclohexyl | cyclohexyl | pyran-O | C₂H₄OCH₂ | C₂H₅ |

-continued

| | R₁ | A₁ | A₂ | A₃ | (CH₂)ₘ | R₂ |
|---|---|---|---|---|---|---|
| 366 | C₅H₁₁ | ⬡ | ⬡ | ⬡—O | C₂H₄OCH₂ | C₂H₅ |
| 367 | C₃H₇ | ⬡ | ⬡ | ⬡—O | OCH₂ | C₅H₁₁ |
| 368 | C₅H₁₁ | ⬡ | ⬡ | ⬡—O | OCH₂ | C₅H₁₁ |
| 369 | C₃H₇ | ⬡ | ⬡ | ⬡—O | C₂H₄OCH₂ | C₅H₁₁ |
| 370 | C₅H₁₁ | ⬡ | ⬡ | ⬡—O | C₂H₄OCH₂ | C₅H₁₁ |
| 371 | C₃H₇ | dithiane | ⬡ | ⬡ | OCH₂ | C₃H₇ |
| 372 | C₅H₁₁ | dithiane | ⬡ | ⬡ | OCH₂ | C₃H₇ |
| 373 | C₃H₇ | dithiane | ⬡ | ⬡ | OC₂H₄ | C₃H₇ |
| 374 | C₅H₁₁ | dithiane | ⬡ | ⬡ | OC₂H₄ | C₃H₇ |
| 375 | C₃H₇ | dithiane | ⬡ | ⬡ | OCH₂ | C₈H₁₇ |
| 376 | C₅H₁₁ | dithiane | ⬡ | ⬡ | OCH₂ | C₈H₁₇ |
| 377 | C₃H₇ | dithiane | ⬡ | ⬡ | OC₂H₄ | C₈H₁₇ |
| 378 | C₅H₁₁ | dithiane | ⬡ | ⬡ | OC₂H₄ | C₈H₁₇ |

5,709,820
-continued
| R₁ | A₁ | A₂ | A₃ | (CH₂)ₘ | R₂ |
|---|---|---|---|---|---|
| 379 C₃H₇ |  | 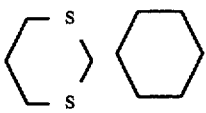 | 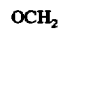 | OCH₂ | CH₃ |
| 380 C₅H₁₁ | 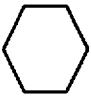 | 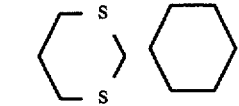 | 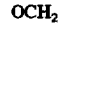 | OCH₂ | CH₃ |
| 381 C₃H₇ | 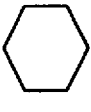 | 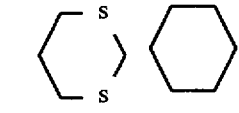 | 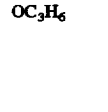 | OC₃H₆ | CH₃ |
| 382 C₅H₁₁ | 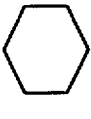 | 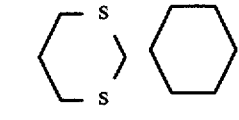 | 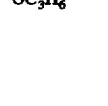 | OC₃H₆ | CH₃ |
| 383 C₃H₇ |  | 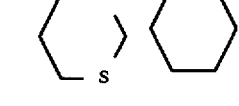 |  | OCH₂ | C₅H₁₁ |
| 384 C₅H₁₁ |  | 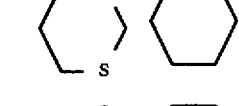 |  | OCH₂ | C₅H₁₁ |
| 385 C₃H₇ | 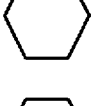 | 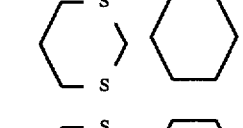 |  | OC₃H₆ | C₅H₁₁ |
| 386 C₅H₁₁ |  | 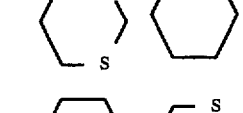 |  | OC₃H₆ | C₅H₁₁ |
| 387 C₃H₇ | 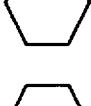 | 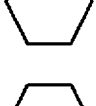 | 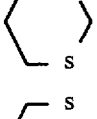 | OCH₂ | C₃H₇ |
| 388 C₅H₁₁ | 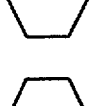 | 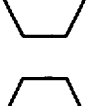 | 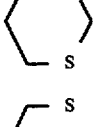 | OCH₂ | C₃H₇ |
| 389 C₃H₇ | 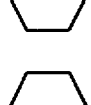 | 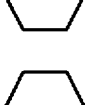 | 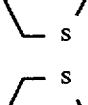 | C₂H₄OCH₂ | C₃H₇ |
| 390 C₅H₁₁ | 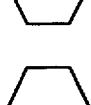 | 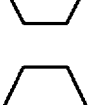 | 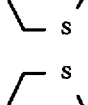 | C₂H₄OCH₂ | C₃H₇ |
| 391 C₃H₇ |  |  | 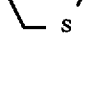 | OCH₂ | C₇H₁₅ |

5,709,820
-continued
| R₁ | A₁ | A₂ | A₃ | (CH₂)ₘ | R₂ |
|---|---|---|---|---|---|
| 392 C₅H₁₁ |  | 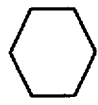 | 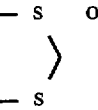 S<br>)<br>S | OCH₂ | C₇H₁₅ |
| 393 C₃H₇ | 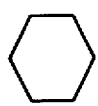 | 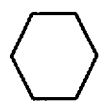 | 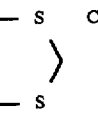 S<br>)<br>S | C₂H₄OCH₂ | C₇H₁₅ |
| 394 C₅H₁₁ | 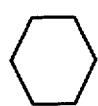 |  | 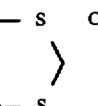 S<br>)<br>S | C₂H₄OCH₂ | C₇H₁₅ |
| 395 C₃H₇ | 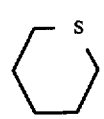 S |  | 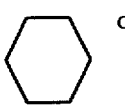 | OCH₂ | C₄H₉ |
| 396 C₅H₁₁ | 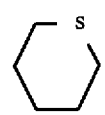 S |  | 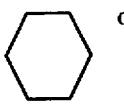 | OCH₂ | C₄H₉ |
| 397 C₃H₇ | 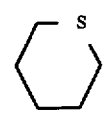 S | 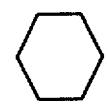 | 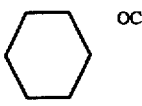 | OC₃H₆ | C₄H₉ |
| 398 C₅H₁₁ | 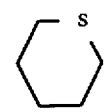 S |  | 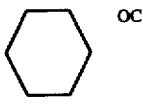 | OC₃H₆ | C₄H₉ |
| 399 C₃H₇ | 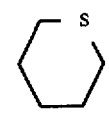 S | 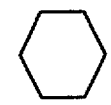 |  | OCH₂ | C₅H₁₁ |
| 400 C₅H₁₁ | 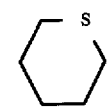 S | 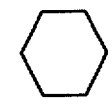 |  | OCH₂ | C₅H₁₁ |
| 401 C₃H₇ | 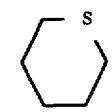 S | 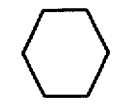 | 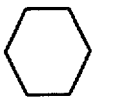 | OC₃H₆ | C₅H₁₁ |
| 402 C₅H₁₁ | 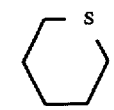 S | 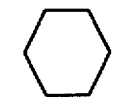 | 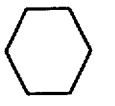 | OC₃H₆ | C₅H₁₁ |
| 403 C₃H₇ |  | 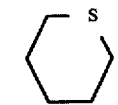 S | 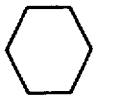 | OCH₂ | C₂H₅ |
| 404 C₅H₁₁ | 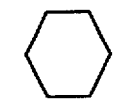 | 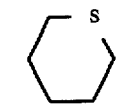 S |  | OCH₂ | C₂H₅ |

-continued

| | $R_1$ | $A_1$ | $A_2$ | $A_3$ | $(CH_2)_m$ | $R_2$ |
|---|---|---|---|---|---|---|
| 405 | $C_3H_7$ | ⬡ | ⬡—S | ⬡ | $CH_2OCH_2$ | $C_2H_5$ |
| 406 | $C_5H_{11}$ | ⬡ | ⬡—S | ⬡ | $CH_2OCH_2$ | $C_2H_5$ |
| 407 | $C_3H_7$ | ⬡ | ⬡—S | ⬡ | $OCH_2$ | $C_3H_7$ |
| 408 | $C_5H_{11}$ | ⬡ | ⬡—S | ⬡ | $OCH_2$ | $C_3H_7$ |
| 409 | $C_3H_7$ | ⬡ | ⬡—S | ⬡ | $CH_2OCH_2$ | $C_3H_7$ |
| 410 | $C_5H_{11}$ | ⬡ | ⬡—S | ⬡ | $CH_2OCH_2$ | $C_3H_7$ |
| 411 | $C_3H_7$ | ⬡ | ⬡ | ⬡—S | $OCH_2$ | $C_5H_{11}$ |
| 412 | $C_5H_{11}$ | ⬡ | ⬡ | ⬡—S | $OCH_2$ | $C_5H_{11}$ |
| 413 | $C_3H_7$ | ⬡ | ⬡ | ⬡—S | $CH_2OC_2H_4$ | $C_5H_{11}$ |
| 414 | $C_5H_{11}$ | ⬡ | ⬡ | ⬡—S | $CH_2OC_2H_4$ | $C_5H_{11}$ |
| 415 | $C_3H_7$ | ⬡ | ⬡ | ⬡—S | $OCH_2$ | $C_6H_{13}$ |
| 416 | $C_5H_{11}$ | ⬡ | ⬡ | ⬡—S | $OCH_2$ | $C_6H_{13}$ |
| 417 | $C_3H_7$ | ⬡ | ⬡ | ⬡—S | $CH_2OC_2H_4$ | $C_6H_{13}$ |
| 418 | $C_5H_{11}$ | ⬡ | ⬡ | ⬡—S | $CH_2OC_2H_4$ | $C_6H_{13}$ |

-continued

| | R₁ | A₁ | A₂ | A₃ | (CH₂)ₘ | R₂ |
|---|---|---|---|---|---|---|
| 419 | ⁄⁄ | ⬡ | ⬡ | ⬡ | | H |
| 420 | ⫽⎯ | ⬡ | ⬡ | ⬡ | | H |
| 421 | ⁄⁄ | ⬡ | ⬡ | ⬡ | (CH₂)₂ | H |
| 422 | ⫽⎯ | ⬡ | ⬡ | ⬡ | (CH₂)₂ | H |
| 423 | ⁄⁄ | ⬡(O,O) | ⬡ | ⬡ | | H |
| 424 | ⫽⎯ | ⬡(O,O) | ⬡ | ⬡ | | H |
| 425 | ⁄⁄ | ⬡(O,O) | ⬡ | ⬡ | (CH₂)₂ | H |
| 426 | ⫽⎯ | ⬡(O,O) | ⬡ | ⬡ | (CH₂)₂ | H |
| 427 | ⁄⁄ | ⬡ | ⬡(O,O) | ⬡ | | H |
| 428 | ⫽⎯ | ⬡ | ⬡(O,O) | ⬡ | | H |
| 429 | ⁄⁄ | ⬡ | ⬡(O,O) | ⬡ | (CH₂)₂ | H |
| 430 | ⫽⎯ | ⬡ | ⬡(O,O) | ⬡ | (CH₂)₂ | H |
| 431 | ⁄⁄ | ⬡ | ⬡ | ⬡(O,O) | | H |

-continued
| | R₁ | A₁ | A₂ | A₃ | (CH₂)ₘ | R₂ |
|---|---|---|---|---|---|---|
| 432 |  |  |  | 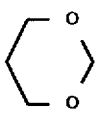 | | H |
| 433 |  |  |  | 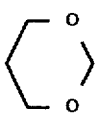 | (CH₂)₂ | H |
| 434 |  |  |  | 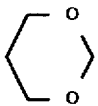 | (CH₂)₂ | H |
| 435 |  |  |  |  | | H |
| 436 |  |  |  |  | | H |
| 437 |  |  |  |  | (CH₂)₂ | H |
| 438 |  |  |  |  | (CH₂)₂ | H |
| 439 |  |  |  |  | | H |
| 440 |  |  |  |  | | H |
| 441 |  |  |  |  | (CH₂)₂ | H |
| 442 |  |  |  |  | (CH₂)₂ | H |
| 443 |  |  |  |  | | H |
| 444 |  |  |  |  | | H |

-continued

| R₁ | A₁ | A₂ | A₃ | (CH₂)ₘ | R₂ |
|---|---|---|---|---|---|
| 445 ⟋⟋ | ⬡ | ⬡ | ⬡—O | (CH₂)₂ | H |
| 446 ⟋\⟋ | ⬡ | ⬡ | ⬡—O | (CH₂)₂ | H |
| 447 ⟋⟋ | ⬡(S,S) | ⬡ | ⬡ |  | H |
| 448 ⟋\⟋ | ⬡(S,S) | ⬡ | ⬡ |  | H |
| 449 ⟋⟋ | ⬡(S,S) | ⬡ | ⬡ | (CH₂)₂ | H |
| 450 ⟋\⟋ | ⬡(S,S) | ⬡ | ⬡ | (CH₂)₂ | H |
| 451 ⟋⟋ | ⬡ | ⬡(S,S) | ⬡ |  | H |
| 452 ⟋\⟋ | ⬡ | ⬡(S,S) | ⬡ |  | H |
| 453 ⟋⟋ | ⬡ | ⬡(S,S) | ⬡ | (CH₂)₂ | H |
| 454 ⟋\⟋ | ⬡ | ⬡(S,S) | ⬡ | (CH₂)₂ | H |
| 455 ⟋⟋ | ⬡ | ⬡ | ⬡(S,S) |  | H |
| 456 ⟋\⟋ | ⬡ | ⬡ | ⬡(S,S) |  | H |
| 457 ⟋⟋ | ⬡ | ⬡ | ⬡(S,S) | (CH₂)₂ | H |

-continued

| | R₁ | A₁ | A₂ | A₃ | (CH₂)ₘ | R₂ |
|---|---|---|---|---|---|---|
| 458 | \\_/ | ⬡ | ⬡ | ⬡(S,S) | (CH₂)₂ | H |
| 459 | /= | ⬡S | ⬡ | ⬡ | | H |
| 460 | \\_/ | ⬡S | ⬡ | ⬡ | | H |
| 461 | /= | ⬡S | ⬡ | ⬡ | (CH₂)₂ | H |
| 462 | \\_/ | ⬡S | ⬡ | ⬡ | (CH₂)₂ | H |
| 463 | /= | ⬡ | ⬡S | ⬡ | | H |
| 464 | \\_/ | ⬡ | ⬡S | ⬡ | | H |
| 465 | /= | ⬡ | ⬡S | ⬡ | (CH₂)₂ | H |
| 466 | \\_/ | ⬡ | ⬡S | ⬡ | (CH₂)₂ | H |
| 467 | /= | ⬡ | ⬡ | ⬡S | | H |
| 468 | \\_/ | ⬡ | ⬡ | ⬡S | | H |
| 469 | /= | ⬡ | ⬡ | ⬡S | (CH₂)₂ | H |
| 470 | \\_/ | ⬡ | ⬡ | ⬡S | (CH₂)₂ | H |
| 471 | /= | ⬡ | ⬡ | ⬡ | (CH₂)₂ | CH₃ |

| | $R_1$ | $A_1$ | $A_2$ | $A_3$ | $(CH_2)_m$ | $R_2$ |
|---|---|---|---|---|---|---|
| 472 | 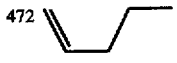 |  |  |  | $(CH_2)_2$ | $CH_3$ |
| 473 |  |  |  |  | | H |
| 474 |  |  |  |  | $(CH_2)_2$ | H |
| 475 |  |  |  |  | $(CH_2)_2$ | $CH_3$ |
| 476 |  | 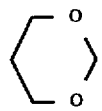 |  |  | $(CH_2)_2$ | $CH_3$ |
| 477 | 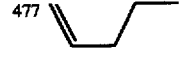 | 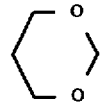 |  |  | $(CH_2)_2$ | $CH_3$ |
| 478 |  | 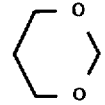 |  |  | | H |
| 479 |  | 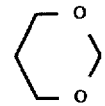 |  |  | $(CH_2)_2$ | H |
| 480 |  | 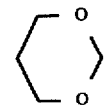 |  |  | $(CH_2)_2$ | $CH_3$ |
| 481 |  |  | 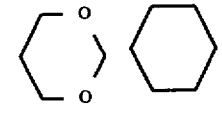 |  | $(CH_2)_2$ | $CH_3$ |
| 482 |  |  | 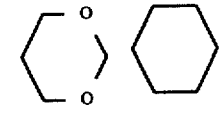 |  | $(CH_2)_2$ | $CH_3$ |
| 483 | 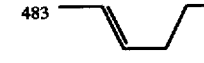 |  | 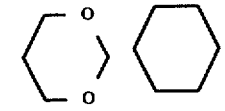 |  | | H |
| 484 | 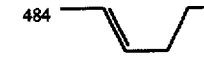 |  | 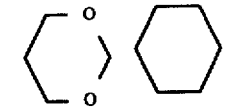 |  | $(CH_2)_2$ | H |

-continued

| | R₁ | A₁ | A₂ | A₃ | (CH₂)ₘ | R₂ |
|---|---|---|---|---|---|---|
| 485 | ⌐⌐⌐ (CH=CH-CH₂) | ⬡ | ⬡(O,O dioxolane) | ⬡ | (CH₂)₂ | CH₃ |
| 486 | // (CH₂=CH) | ⬡ | ⬡ | ⬡(O,O dioxolane) | (CH₂)₂ | CH₃ |
| 487 | ⌐⌐⌐ | ⬡ | ⬡ | ⬡(O,O dioxolane) | (CH₂)₂ | CH₃ |
| 488 | ⌐⌐⌐ | ⬡ | ⬡ | ⬡(O,O dioxolane) | | H |
| 489 | ⌐⌐⌐ | ⬡ | ⬡ | ⬡(O,O dioxolane) | (CH₂)₂ | H |
| 490 | ⌐⌐⌐ | ⬡ | ⬡ | ⬡(O,O dioxolane) | (CH₂)₂ | CH₃ |
| 491 | // | ⬡(O pyran) | ⬡ | ⬡ | (CH₂)₂ | CH₃ |
| 492 | ⌐⌐⌐ | ⬡(O pyran) | ⬡ | ⬡ | (CH₂)₂ | CH₃ |
| 493 | ⌐⌐⌐ | ⬡(O pyran) | ⬡ | ⬡ | | H |
| 494 | ⌐⌐⌐ | ⬡(O pyran) | ⬡ | ⬡ | (CH₂)₂ | H |
| 495 | ⌐⌐⌐ | ⬡(O pyran) | ⬡ | ⬡ | (CH₂)₂ | CH₃ |
| 496 | // | ⬡ | ⬡(O pyran) | ⬡ | (CH₂)₂ | CH₃ |
| 497 | ⌐⌐⌐ | ⬡ | ⬡(O pyran) | ⬡ | (CH₂)₂ | CH₃ |

-continued
| | R₁ | A₁ | A₂ | A₃ | (CH₂)ₘ | R₂ |
|---|---|---|---|---|---|---|
| 498 | 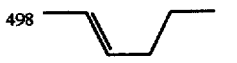 |  |  O |  | | H |
| 499 |  |  |  O | | (CH₂)₂ | H |
| 500 | 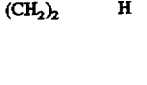 |  |  O | | (CH₂)₂ | CH₃ |
| 501 |  | 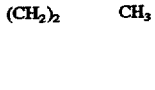 |  |  O | (CH₂)₂ | CH₃ |
| 502 |  | 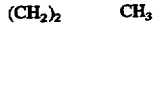 | 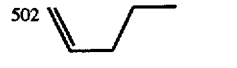 |  O | (CH₂)₂ | CH₃ |
| 503 |  | 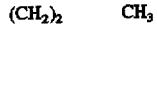 |  |  O | | H |
| 504 |  |  | 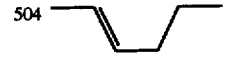 |  O | (CH₂)₂ | H |
| 505 |  | 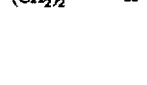 | 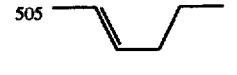 |  O | (CH₂)₂ | CH₃ |
| 506 |  | 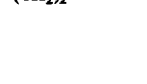 S,S |  |  | (CH₂)₂ | CH₃ |
| 507 |  |  S,S |  |  | (CH₂)₂ | CH₃ |
| 508 | 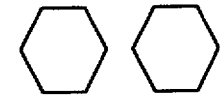 | 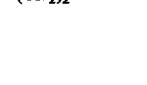 S,S | 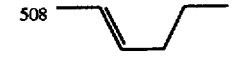 |  | | H |
| 509 |  |  S,S |  |  | (CH₂)₂ | H |
| 510 |  | 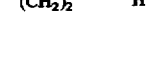 S,S |  |  | (CH₂)₂ | CH₃ |

| | R₁ | A₁ | A₂ | A₃ | (CH₂)ₘ | R₂ |
|---|---|---|---|---|---|---|
| 511 | //= | ⬡ | S-S ring | ⬡ | (CH₂)₂ | CH₃ |
| 512 | \=\ | ⬡ | S-S ring | ⬡ | (CH₂)₂ | CH₃ |
| 513 | \=\ | ⬡ | S-S ring | ⬡ | | H |
| 514 | \=\ | ⬡ | S-S ring | ⬡ | (CH₂)₂ | H |
| 515 | \=\ | ⬡ | S-S ring | ⬡ | (CH₂)₂ | CH₃ |
| 516 | //= | ⬡ | ⬡ | S-S ring | (CH₂)₂ | CH₃ |
| 517 | \=\ | ⬡ | ⬡ | S-S ring | (CH₂)₂ | CH₃ |
| 518 | \=\ | ⬡ | ⬡ | S-S ring | | H |
| 519 | \=\ | ⬡ | ⬡ | S-S ring | (CH₂)₂ | H |
| 520 | \=\ | ⬡ | ⬡ | S-S ring | (CH₂)₂ | CH₃ |
| 521 | //= | S ring | ⬡ | ⬡ | (CH₂)₂ | CH₃ |
| 522 | \=\ | S ring | ⬡ | ⬡ | (CH₂)₂ | CH₃ |
| 523 | \=\ | S ring | ⬡ | ⬡ | | H |

-continued

| R₁ | A₁ | A₂ | A₃ | (CH₂)ₘ | R₂ |
|---|---|---|---|---|---|
| 524  |  | 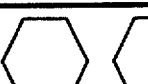 | 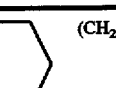 | (CH₂)₂ | H |
| 525  |  | 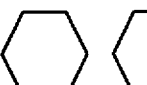 | 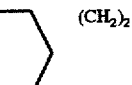 | (CH₂)₂ | CH₃ |
| 526  |  | 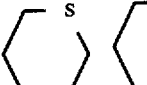 | 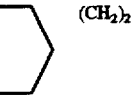 | (CH₂)₂ | CH₃ |
| 527  |  | 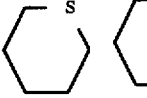 | 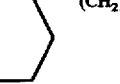 | (CH₂)₂ | CH₃ |
| 528  |  | 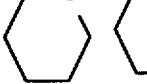 | 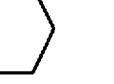 | | H |
| 529  |  | 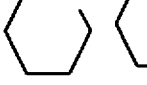 | 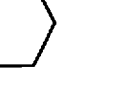 | (CH₂)₂ | H |
| 530  |  | 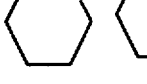 | 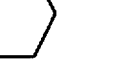 | (CH₂)₂ | CH₃ |
| 531  |  |  | 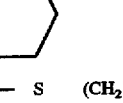 | (CH₂)₂ | CH₃ |
| 532  |  |  | 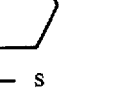 | (CH₂)₂ | CH₃ |
| 533  |  | 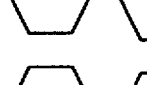 | 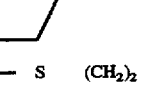 | | H |
| 534  |  | 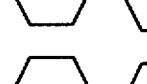 | 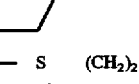 | (CH₂)₂ | H |
| 535  |  | 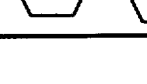 | 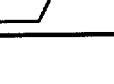 | (CH₂)₂ | CH₃ |

Further, the use of the present liquid crystalline compounds in a liquid crystal composition is illustrated by the following use examples.

Use Example 1

A clearing point (Cp.) was 72.4° C. for a nematic liquid crystal composition which comprises:

4-(trans-4-propylcyclohexyl)benzonitrile 24% by weight
4-(trans-4-pentylcyclohexyl)benzonitrile 36% by weight
4-(trans-4-heptylcyclohexyl)benzonitrile 25% by weight
4-(4-propylphenyl)benzonitrile 15% by weight The above liquid crystal composition enclosed in a twisted nematic cell (TN cell) with a cell thickness of 9 μm had an operating threshold voltage (Vth) of 1.78 V, a dielectric anisotropy (Δε) of 11.0, an optical anisotropy (Δn) of 0.137 and a viscosity at 20° C. (η20) of 27.0 mPa·s.

85 parts of the above liquid crystal composition as a mother liquid crystal were mixed with 15 parts of 1-ethenyl-trans-4-(trans-4-propylcyclohexyl)cyclohexyl-cyclohexane (Compound No. 1) shown in Example 1 and the resulting mixture was measured for physical properties, with the results of Cp.: 85.5° C., Vth: 2.03 V, Δε: 10.2, Δn: 0.132 and η20: 25.9 mPa·s. This composition was allowed to stand in a refrigerator at −20° C. over 40 days, but no crystals or SB phase was observed.

For comparison, the compound (a-1) disclosed in Japanese Patent Kokai 57-165328 wherein R is $C_3H_7$ and R' is $CH_3$ and the compound (c-1) disclosed in Journal de Physique, Suppl. No. 3, 36, C1-379, March 1975 wherein R is $C_2H_5$ were synthesized in accordance with the methods illustrated therein, and the resultant compounds were used as comparative compounds in this experiment. 85 parts of the present liquid crystal composition as a mother liquid crystal were mixed with 15 parts of the compound (a-1) to prepare a comparative composition. Alternatively, 95 parts of the present liquid crystal composition as a mother liquid crystal were mixed with 5 part of the compound (c-1) to prepare another comparative composition. The liquid crystal compositions were determined for the physical properties, with the results shown in Table 1.

TABLE 1

| Structure | NI (°C.) | η₂₀ (mPa·s) | K₃₃/K₁₁ |
|---|---|---|---|
| 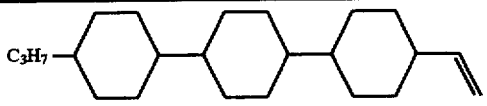 $C_3H_7$— | 92.1 | 25.4 | 2.50 |
| 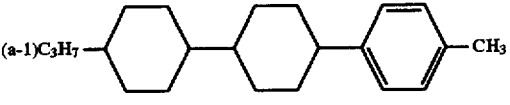 (a-1)$C_3H_7$—  —$CH_3$ | 85.6 | 25.5 | 1.88 |
| 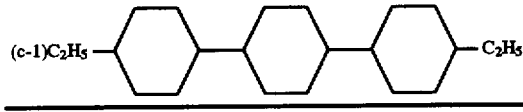 (c-1)$C_2H_5$—  —$C_2H_5$ | 27.0 | | |

Table 1 shows that the present compounds have a higher clearing point of 92.1° C. by approximately 8% and a higher elastic constant ratio $K_{33}/K_{11}$ by approximately 33%, while having an approximately equivalent level of viscosity, as compared with the tricyclic compound (a-1) containing an alkyl group on both side chains described in Japanese Patent Kokai 57-165328. Further, it can be seen that the compound (c-1) having the same skeleton as the present compounds has only 5% solubility in the above mother liquid crystal, a remarkably poor compatibility and a higher viscosity by approximately 6%, as compared with the present compounds.

This demonstrates that the compounds of the present invention have more improved characteristics than the prior art compounds.

In the following Use Examples 2–18, for convenience' sake, the compounds constituting the liquid crystal composition are designated using the following symbols.

R—(A₁—Z₁— ----- —Zₙ—(Aₙ—X

| Left terminal group R— | Symbol | Linking group —$Z_1$—, —$Z_n$— | Symbol |
|---|---|---|---|
| $C_nH_{2n+1}$— | n- | —$C_2H_4$— | 2 |
| $C_nH_{2n+1}O$— | nO— | —$C_4H_8$— | 4 |
| $C_nH_{2n+1}OC_mH_{2m}$— | nOm- | —COO— | E |
| $CH_2=CH$— | V- | —C≡C— | T |
| $CH_2=CHC_nH_{2n}$— | Vn- | —CH=CH— | V |
| $C_nH_{2n+1}CH=CHC_mH_{2m}$— | nVm- | —$CF_2O$— | CF2O |
| $C_nH_{2n+1}CH=CHC_mH_{2m}CH=CHC_kH_{2k}$— | nVmVk- | —$OCF_2$— | OCF2 |
| | | —$C_3H_6O$— | 30 |

-continued
$$R-(A_1)-Z_1-\cdots\cdots-Z_n-(A_n)-X$$
| Ring structure $-(A_1)-$, $-(A_n)-$ | Symbol | Right terminal group $-X$ | Symbol |
|---|---|---|---|
|  | B | $-F$ | $-F$ |
| 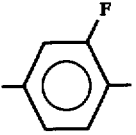 | B(F) | $-Cl$ | $-CL$ |
| 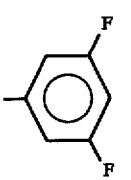 | B(F,F) | $-CN$ | $-C$ |
| 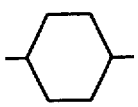 | H | $-CF_3$ | CF3 |
| 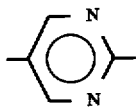 | Py | $-OCF_3$ | $-OCF3$ |
| 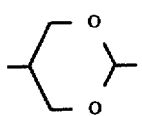 | D | $-OCF_2H$ | $-OCF2H$ |
| 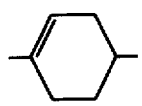 | Ch | $-C_nH_{2n+1}$ | -n |
|  |  | $-OC_nH_{2n+1}$ | $-On$ |
|  |  | $-COOCH_3$ | $-EMe$ |
|  |  | $-C_nH_{2n}CH=CH_2$ | -nV |
|  |  | $-C_mH_{2m}CH=CHC_nH_{2n+1}$ | -mVn |
|  |  | $-C_mH_{2m}CH=CHC_nH_{2n}F$ | -mVnF |
|  |  | $-CH=CF_2$ | $-VFF$ |
Example of designation
3-H2B(F,F)B(F)—F
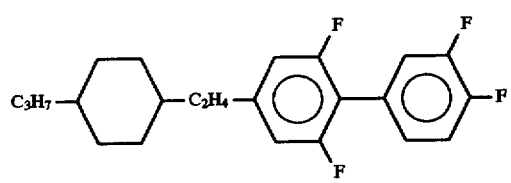
1V2-BEB(F,F)—C
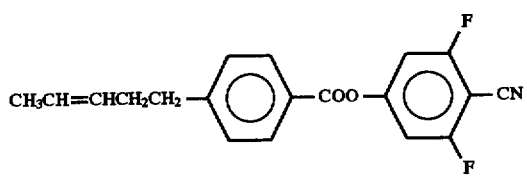
3-HB(F)TB-2
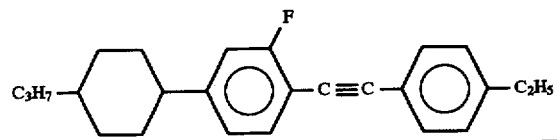

In the physical properties indicated in the use examples, viscosity (η) shows the values determined at 20.0° C., and dielectric anisotropy (Δε), optical anisotropy (Δn) and threshold voltage (Vth) shows the values determined at 25.0° C.

| Use Example 2 | |
|---|---|
| 3-HHH-V (No. 1) | 3.0% |
| 1V2-HHH-V (No. 473) | 3.0% |
| 1V2-BEB(F,F)-C | 5.0% |
| 3-HB-C | 25.0% |
| 3-HB-O2 | 6.0% |
| 1-BTB-3 | 5.0% |
| 2-BTB-1 | 10.0% |
| 3-HH-4 | 5.0% |
| 3-HHB-1 | 11.0% |
| 3-HHB-3 | 9.0% |
| 3-H2BTB-2 | 4.0% |
| 3-H2BTB-3 | 4.0% |
| 3-H2BTB-4 | 4.0% |
| 3-HB(F)TB-2 | 6.0% |
| $T_{NI} = 90.4$ (°C.) | |
| $\eta = 14.0$ (mPa · s) | |
| $\Delta n = 0.154$ | |
| $\Delta \epsilon = 7.3$ | |
| $V_{th} = 2.08$ (V) | |
| Use Example 3 | |
| 3-HHH-2V (No. 7) | 4.0% |
| V-HHH-2V (No. 421) | 4.0% |
| V2-HB-C | 12.0% |
| 1V2-HB-C | 12.0% |
| 3-HB-C | 24.0% |
| 3-HB(F)-C | 10.0% |
| 2-BTB-1 | 2.0% |
| 3-HH-4 | 8.0% |
| 2-HHB-C | 3.0% |
| 3-HHB-C | 6.0% |
| 3-HB(F)TB-2 | 8.0% |
| 3-H2BTB-2 | 4.0% |
| 3-H2BTB-3 | 3.0% |
| $T_{NI} = 90.8$ (°C.) | |
| $\eta = 20.3$ (mPa · s) | |
| $\Delta n = 0.148$ | |
| $\Delta \epsilon = 9.4$ | |
| $V_{th} = 1.91$ (V) | |
| Use Example 4 | |
| 3-HHH-V (No. 1) | 5.0% |
| 2O1-BEB(F)-C | 5.0% |
| 3O1-BEB(F)-C | 15.0% |
| 4O1-BEB(F)-C | 13.0% |
| 5O1-BEB(F)-C | 13.0% |
| 3-HB-O2 | 4.0% |
| 2-HHB(F)-C | 15.0% |
| 3-HHB(F)-C | 15.0% |
| 3-HB(F)TB-2 | 4.0% |
| 3-HB(F)TB-3 | 4.0% |
| 3-HHB-1 | 3.0% |
| 3-HHB-O1 | 4.0% |
| $T_{NI} = 90.1$ (°C.) | |
| $\eta = 85.4$ (mPa · s) | |
| $\Delta n = 0.142$ | |
| $\Delta \epsilon = 30.9$ | |
| $V_{th} = 0.87$ (V) | |
| Use Example 5 | |
| V-HHH-2V (No. 421) | 4.0% |
| 5-PyB-F | 4.0% |
| 3-PyB(F)-F | 4.0% |
| 2-BB-C | 5.0% |
| 4-BB-C | 4.0% |
| 5-BB-C | 5.0% |
| 2-PyB-2 | 3.0% |
| 3-PyB-2 | 3.0% |
| 4-PyB-2 | 2.0% |
| 6-PyB-O5 | 3.0% |
| 6-PyB-O6 | 3.0% |
| 6-PyB-O7 | 3.0% |
| 6-PyB-O8 | 3.0% |
| 3-PyBB-F | 6.0% |
| 4-PyBB-F | 6.0% |
| 5-PyBB-F | 6.0% |
| 3-HHB-3 | 8.0% |
| 2-H2BTB-2 | 4.0% |
| 2-H2BTB-3 | 4.0% |
| 2-H2BTB-4 | 5.0% |
| 3-H2BTB-2 | 5.0% |
| 3-H2BTB-3 | 5.0% |
| 3-H2BTB-4 | 5.0% |
| $T_{NI} = 94.2$ (°C.) | |
| $\eta = 34.7$ (mPa · s) | |
| $\Delta n = 0.201$ | |
| $\Delta \epsilon = 6.4$ | |
| $V_{th} = 2.27$ (V) | |
| Use Example 6 | |
| 3-DHH-V (No. 16) | 3.0% |
| 3-DB-C | 10.0% |
| 4-DB-C | 10.0% |
| 2-BEB-C | 12.0% |
| 3-BEB-C | 4.0% |
| 3-PyB(F)-F | 6.0% |
| 3-HEB-O4 | 8.0% |
| 4-HEB-O2 | 6.0% |
| 5-HEB-O1 | 6.0% |
| 3-HEB-O2 | 5.0% |
| 5-HEB-O2 | 4.0% |
| 5-HEB-5 | 5.0% |
| 4-HEB-5 | 5.0% |
| 1O-BEB-2 | 4.0% |
| 3-HHB-1 | 6.0% |
| 3-HHEBB-C | 3.0% |
| 5-HBEBB-C | 3.0% |
| $T_{NI} = 67.4$ (°C.) | |
| $\eta = 36.5$ (mPa · s) | |
| $\Delta n = 0.117$ | |
| $\Delta \epsilon = 11.0$ | |
| $V_{th} = 1.35$ (V) | |
| Use Example 7 | |
| 3-HHCh-V | 4.0% |
| 3-HB-C | 21.0% |
| 5-HB-C | 3.0% |
| 1O1-HB-C | 10.0% |
| 3-HB(F)-C | 10.0% |
| 2-PyB-2 | 2.0% |
| 3-PyB-2 | 2.0% |
| 4-PyB-2 | 2.0% |
| 1O1-HH-3 | 7.0% |
| 2-BTB-O1 | 7.0% |
| 3-HHB-F | 4.0% |
| 3-HHB-O1 | 4.0% |
| 3-HHB-3 | 8.0% |
| 3-H2BTB-2 | 3.0% |
| 3-H2BTB-3 | 3.0% |
| 2-PyBH-3 | 4.0% |
| 3-PyBH-3 | 3.0% |
| 3-PyBH-2 | 3.0% |
| $T_{NI} = 78.0$ (°C.) | |
| $\eta = 18.2$ (mPa · s) | |
| $\Delta n = 0.139$ | |
| $\Delta \epsilon = 8.4$ | |
| $V_{th} = 1.70$ (V) | |
| Use Example 8 | |
| 3-HHH-V (No. 1) | 5.0% |
| 3-DHH-V (No. 16) | 5.0% |
| 2O1-BEB(F)-C | 5.0% |
| 3O1-BEB(F)-C | 12.0% |
| 5O1-BEB(F)-C | 4.0% |
| 1V2-BEB(F,F)-C | 10.0% |
| 3-HH-EMe | 10.0% |
| 3-HB-O2 | 21.0% |
| 3-HHEB-F | 3.0% |
| 5-HHEB-F | 3.0% |
| 3-HBEB-F | 4.0% |
| 2O1-HBEB(F)-C | 4.0% |

-continued

| | |
|---|---|
| 3-HBEB(F,F)-C | 2.0% |
| 3-HHB-F | 4.0% |
| 3-HHB-O1 | 4.0% |
| 3-HEBEB-F | 2.0% |
| 3-HEBEB-1 | 2.0% |
| $T_{NI}$ =0 79.1 (°C.) | |
| η = 35.3 (mPa · s) | |
| Δn = 0.110 | |
| Δε = 23.5 | |
| $V_{th}$ = 0.99 (V) | |

Use Example 9

| | |
|---|---|
| 3-HHH-V (No. 1) | 3.0% |
| V-HHH-2V (No. 421) | 3.0% |
| 3-DHH-V (No. 16) | 3.0% |
| 3-HHCh-V | 3.0% |
| 2O1-BEB(F)-C | 5.0% |
| 3O1-BEB(F)-C | 12.0% |
| 5O1-BEB(F)-C | 4.0% |
| 1V2-BEB(F,F)-C | 16.0% |
| 3-HB-O2 | 14.0% |
| 3-HH-4 | 3.0% |
| 3-HHB-F | 3.0% |
| 3-HHB-1 | 3.0% |
| 3-HHB-O1 | 4.0% |
| 3-HBEB-F | 4.0% |
| 3-HHEB-F | 7.0% |
| 3-H2BTB-2 | 4.0% |
| 3-H2BTB-4 | 4.0% |
| 3-HB(F)TB-2 | 5.0% |
| $T_{NI}$ = 90.4 (°C.) | |
| η = 39.3 (mPa · s) | |
| Δn = 0.133 | |
| Δε = 28.0 | |
| $V_{th}$ = 1.01 (V) | |

Use Example 10

| | |
|---|---|
| 3-HHH-V (No. 1) | 4.0% |
| 3-DHH-V (No. 16) | 4.0% |
| 3-HHCh-V | 4.0% |
| 2-BEB-C | 12.0% |
| 3-BEB-C | 4.0% |
| 4-BEB-C | 6.0% |
| 3-HB-O2 | 7.0% |
| 3-HB-C | 28.0% |
| 4-HEB-O2 | 8.0% |
| 5-HEB-O1 | 8.0% |
| 3-HEB-O2 | 6.0% |
| 5-HEB-O2 | 5.0% |
| 3-HHB-O1 | 4.0% |
| $T_{NI}$ = 69.7 (°C.) | |
| η = 25.7 (mPa · s) | |
| Δn = 0.108 | |
| Δε = 9.3 | |
| $V_{th}$ = 1.41 (V) | |

Use Example 11

| | |
|---|---|
| 3-HHH-V (No. 1) | 2.0% |
| 3-HHCh-V | 2.0% |
| 2-BEB-C | 10.0% |
| 5-BB-C | 12.0% |
| 7-BB-C | 7.0% |
| 3-HB-O2 | 3.0% |
| 1-BTB-3 | 7.0% |
| 2-BTB-1 | 10.0% |
| 1O-BEB-2 | 10.0% |
| 1O-BEB-5 | 12.0% |
| 2-HHB-1 | 4.0% |
| 3-HHB-F | 4.0% |
| 3-HHB-1 | 7.0% |
| 3-HHB-O1 | 4.0% |
| 3-HHB-3 | 6.0% |
| $T_{NI}$ = 65.9 (°C.) | |
| η = 10.4 (mPa · s) | |
| Δn = 0.158 | |
| Δε = 6.5 | |
| $V_{th}$ = 1.78 (V) | |

Use Example 12

| | |
|---|---|
| 3-HHH-V (No. 1) | 4.0% |
| V-HHH-2V (No. 421) | 3.0% |
| 2-HHB(F)-F | 17.0% |
| 3-HHB(F)-F | 17.0% |
| 5-HHB(F)-F | 16.0% |
| 7-HB(F)-F | 6.0% |
| 2-H2HB(F)-F | 10.0% |
| 3-H2HB(F)-F | 5.0% |
| 5-H2HB(F)-F | 10.0% |
| 2-HBB(F)-F | 6.0% |
| 3-HBB(F)-F | 6.0% |
| $T_{NI}$ = 99.5 (°C.) | |
| η = 20.3 (mPa · s) | |
| Δn = 0.083 | |
| Δε = 5.0 | |
| $V_{th}$ = 2.21 (V) | |

Use Example 13

| | |
|---|---|
| 3-HHH-V (No. 1) | 4.0% |
| 1V2-HHH-V (No. 473) | 4.0% |
| 7-HB(F)-F | 5.0% |
| 5-H2B(F)-F | 5.0% |
| 3-HB-O2 | 13.0% |
| 3-HH-4 | 5.0% |
| 2-HHB(F)-F | 10.0% |
| 3-HHB(F)-F | 10.0% |
| 5-HHB(F)-F | 10.0% |
| 3-H2HB(F)-F | 5.0% |
| 2-HBB(F)-F | 3.0% |
| 3-HBB(F)-F | 3.0% |
| 5-HBB(F)-F | 6.0% |
| 2-H2BB(F)-F | 5.0% |
| 3-H2BB(F)-F | 6.0% |
| 3-HHB-O1 | 2.0% |
| 3-HHB-3 | 4.0% |
| $T_{NI}$ = 87.3 (°C.) | |
| η = 17.9 (mPa · s) | |
| Δn = 0.088 | |
| Δε = 3.1 | |
| $V_{th}$ = 2.67 (V) | |

Use Example 14

| | |
|---|---|
| 3-HHH-V (No. 1) | 4.0% |
| 3-DHH-V (No. 16) | 4.0% |
| 7-HB(F,F)-F | 9.0% |
| 3-HB-O2 | 9.0% |
| 2-HHB(F)-F | 10.0% |
| 3-HHB(F)-F | 10.0% |
| 5-HHB(F)-F | 10.0% |
| 2-HBB(F)-F | 9.0% |
| 3-HBB(F)-F | 9.0% |
| 2-HBB-F | 4.0% |
| 3-HBB-F | 4.0% |
| 5-HBB-F | 3.0% |
| 3-HBB(F,F)-F | 5.0% |
| 5-HBB(F,F)-F | 10.0% |
| $T_{NI}$ = 84.5 (°C.) | |
| η = 19.2 (mPa · s) | |
| Δn = 0.101 | |
| Δε = 5.9 | |
| $V_{th}$ = 1.97 (V) | |

Use Example 15

| | |
|---|---|
| 3-HHH-V (No. 1) | 3.0% |
| 3-HHCh-V | 3.0% |
| 7-HB(F,F)-F | 7.0% |
| 3-H2HB(F,F)-F | 12.0% |
| 4-H2HB(F,F)-F | 10.0% |
| 5-H2HB(F,F)-F | 10.0% |
| 3-HHB(F,F)-F | 10.0% |
| 4-HHB(F,F)-F | 5.0% |
| 3-HH2B(F,F)-F | 6.0% |
| 5-HH2B(F,F)-F | 10.0% |
| 3-HBB(F,F)-F | 12.0% |
| 5-HBB(F,F)-F | 12.0% |
| $T_{NI}$ = 75.1 (°C.) | |
| η = 26.0 (mPa · s) | |
| Δn = 0.083 | |
| Δε = 8.3 | |
| $V_{th}$ = 1.65 (V) | |

Use Example 16

| | |
|---|---|
| 3-DHH-V (No. 16) | 3.0% |
| 3-HHCh-V | 3.0% |
| 3-HB-CL | 10.0% |
| 5-HB-CL | 4.0% |
| 7-HB-CL | 4.0% |
| 7-HB(F)-F | 2.0% |
| 1O1-HH-5 | 5.0% |
| 2-HBB(F)-F | 8.0% |
| 3-HBB(F)-F | 8.0% |
| 5-HBB(F)-F | 14.0% |
| 4-HHB-CL | 8.0% |
| 3-H2HB(F)-CL | 4.0% |
| 3-HBB(F,F)-F | 10.0% |
| 5-H2BB(F,F)-F | 9.0% |
| 3-HB(F)VB-2 | 4.0% |
| 3-HB(F)VB-3 | 4.0% |
| $T_{NI}$ = 88.2 (°C.) | |
| η = 20.1 (mPa · s) | |
| Δn = 0.126 | |
| Δε = 4.7 | |
| $V_{th}$ = 2.35 (V) | |

Use Example 17

| | |
|---|---|
| 3-HHH-2V (No. 7) | 4.0% |
| 3-DHH-V | 4.0% |
| 3-HHB(F,F)-F | 9.0% |
| 7-HB(F,F)-F | 4.0% |
| 3-H2HB(F,F)-F | 8.0% |
| 4-H2HB(F,F)-F | 8.0% |
| 3-HBB(F,F)-F | 21.0% |
| 5-HBB(F,F)-F | 20.0% |
| 3-H2BB(F,F)-F | 10.0% |
| 5-HHBB(F,F)-F | 3.0% |
| 3-HH2BB(F,F)-F | 3.0% |
| 5-HHEBB-F | 2.0% |
| 1O1-HBBH-4 | 4.0% |
| $T_{NI}$ = 95.8 (°C.) | |
| η = 29.8 (mPa · s) | |
| Δn = 0.111 | |
| Δε = 8.6 | |
| $V_{th}$ = 1.80 (V) | |

Use Example 18

| | |
|---|---|
| V-HHH-2V (No. 421) | 4.0% |
| 3-HHCh-V | 4.0% |
| 2-HHB(F)-F | 2.0% |
| 3-HHB(F)-F | 2.0% |
| 5-HHB(F)-F | 2.0% |
| 2-HBB(F)-F | 6.0% |
| 3-HBB(F)-F | 6.0% |
| 5-HBB(F)- F | 3.0% |
| 7-HB(F,F)-F | 3.0% |
| 2-H2BB(F)-F | 9.0% |
| 3-H2BB(F)-F | 9.0% |
| 3-HBB(F,F)-F | 25.0% |
| 5-HBB(F,F)-F | 19.0% |
| 1O1-HBBH-4 | 3.0% |
| 1O1-HBBH-5 | 3.0% |
| $T_{NI}$ = 94.9 (°C.) | |
| η = 31.2 (mPa · s) | |
| Δn = 0.127 | |
| Δε = 7.3 | |
| $V_{th}$ = 1.91 (V) | |

APPLICABILITY OF THE INVENTION

As described above, the compounds of the present invention characterized by a tricyclic ring having an alkenyl group in the molecule have a lower viscosity, a higher elastic constant ratio and a good compatiblity with other liquid crystalline compounds at a lower temperature. When the present compounds are used as a component for a liquid crystal composition, a novel liquid crystal composition having the desired physical properties can be provided by utilizing a good compatibility with other liquid crystal materials and further by adequately selecting the 6-membered rings, substituents and/or linking groups in the molecule constituting element.

What is claimed is:

1. A liquid crystalline compound of formula (I)

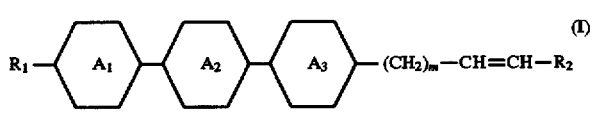

wherein $R_1$ is an alkyl group of 1–15 carbons, an alkenyl group of 2–15 carbons or an alkyl or alkenyl group in which one or plural non-adjacent methylene groups (—$CH_2$—) is or are replaced by —O—, —S—, [—C≡C—] or —COO—, $R_2$ is a hydrogen atom or an alkyl group of 1–10 carbons; m is 0–5; when m is 2 or more, one methylene group or plural non-adjacent methylene groups in —($CH_2$)$_m$— may be replaced by —O—; and the rings $A_1$, $A_2$ and $A_3$ are independently a 1,4-cyclohexylene group, a cyclohexene-1,4-diyl group a 1,3-dioxane-2,5, diyl group, a tetrahydropyrane-2,5, diyl group, a 1,3-dithian-2,5-diyl group or a tetrahydrothiopyrane-2,5-diyl group, provided $A_3$ is not a 1,3-dioxane-2,5-diyl group when $A_2$ is a 1,4-cyclohexylene group and no methylene group in —($CH_2$)$_m$— may be replaced by —O— when rings A1, A2 and A3 are all 1,4-cyclohexylene groups.

2. The liquid crystalline compound of claim 1 wherein m is 0.

3. The liquid crystalline compound of claim 1 wherein m is 2.

4. The liquid crystalline compound of claim 2 wherein $R_1$ is an alkenyl group.

5. The liquid crystalline compound of claim 3 wherein $R_1$ is an alkenyl group.

6. A liquid crystal composition which comprises at least one of the liquid crystalline compounds set forth in any one of claims 1–5.

7. A liquid crystal composition which comprises:
   (i) as a first component, at least one of the liquid crystalline compounds set forth in any one of claims 1–5, and
   (ii) as a second component, at least one compound selected from the group consisting of the compounds of formulae (II-a), (II-b) and (II-c)

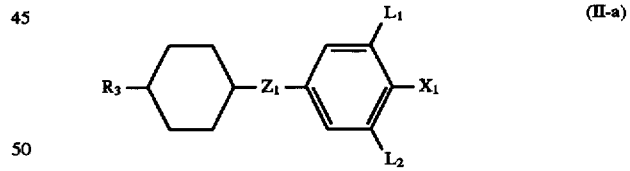

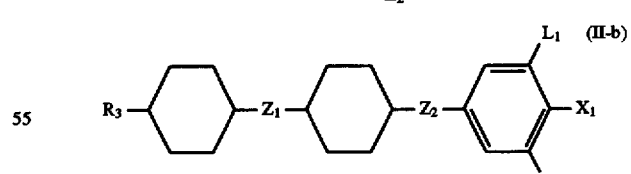

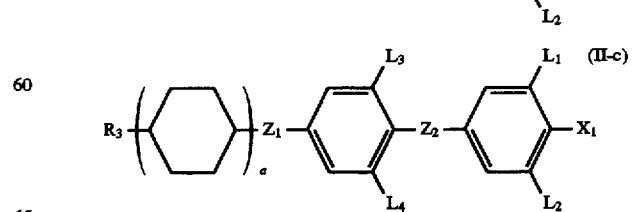

wherein $R_3$ is an alkyl group of 1–10 carbons, $X_1$ is F, Cl, $OCF_3$, $OCF_2H$, $CF_3$, $CF_2H$ or $CFH_2$, $L_1$, $L_2$, $L_3$ and $L_4$ are independently H or F, $Z_1$ and $Z_2$ are independently —(CH$_2$)$_2$—, —CH=CH— or a covalent bond and a is 1 or 2.

8. A liquid crystal composition which comprises:
  (i) as a first component, at least one of the liquid crystalline compounds set forth in any one of claims 1–5,
  (ii) as a second component, at least one compound selected from the group consisting of the compounds of formulae (III-a), (III-b), (III-c), (III-d) and (III-e)

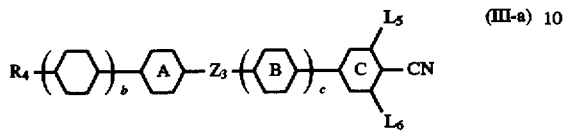
(III-a)

wherein $R_4$ is F, an alkyl group of 1–10 carbons or an alkenyl group of 2–10 carbons, the methylene group (—CH$_2$—) in said alkyl or alkenyl group may be replaced by an oxygen atom (—O—) provided that two or more methylene groups in series are not replaced by an oxygen atom, the ring A is a trans-1,4-cyclohexylene, 1,4-phenylene, pyrimidine-2,5-diyl or 1,3-dioxane-2,5-diyl group, the ring B is a trans-1,4-cyclohexylene, 1,4-phenylene or pyrimidine-2,5-diyl group, the ring C is a trans-1,4-cyclohexylene or 1,4-phenylene group, $Z_3$ is —(CH$_2$)$_2$—, —COO— or a covalent bond, $L_5$ and $L_6$ are independently H or F, and b and c are independently 0 or 1,

(III-b)

wherein $R_5$ is an alkyl group of 1–10 carbons, $L_7$ is H or F and d is 0 or 1,

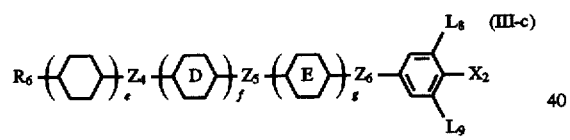
(III-c)

wherein $R_6$ is an alkyl group of 1–10 carbons, the rings D and E are independently a trans-1,4-cyclohexylene or 1,4-phenylene group, $Z_4$ and $Z_5$ are independently —COO— or a covalent bond, $Z_6$ is —COO— or —C≡C—, $L_8$ and $L_9$ are independently H or F, $X_2$ is F, OCF$_3$, OCF$_2$H, CF$_3$, CF$_2$H or CFH$_2$, provided that when $X_2$ is OCF$_3$, OCF$_2$H, CF$_3$, CF$_2$H or CFH$_2$, both $L_8$ and $L_9$ represent a hydrogen atom, and e, f and g are independently 0 or 1,

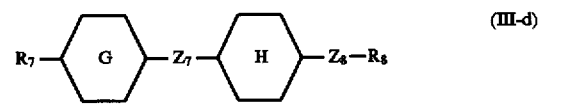
(III-d)

wherein $R_7$ and $R_8$ are independently an alkyl group of 1–10 carbons or an alkenyl group of 2–10 carbons, the methylene group (—CH$_2$—) in said alkyl or alkenyl group may be replaced by an oxygen atom (—O—) provided that two or more methylene groups in series are not replaced by an oxygen atom, the ring G is a trans-1,4-cyclohexylene, 1,4-phenylene or pyrimidine-2,5-diyl group, the ring H is a trans-1,4-cyclohexylene or 1,4-phenylene group, $Z_7$ is —C≡C—, —COO—, —(CH$_2$)$_2$—, —CH=CH—C≡C— or a covalent bond, and $Z_8$ is —COO or a covalent bond,

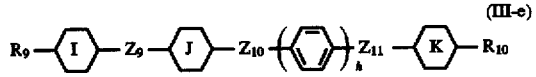
(III-e)

wherein $R_9$ and $R_{10}$ are independently an alkyl group of 1–10 carbons or an alkenyl group of 2–10 carbons, the methylene group (—CH$_2$—) in said alkyl or alkenyl group may be replaced by an oxygen atom (—O—) provided that two or more methylene groups in series are not replaced by an oxygen atom, the ring I is a trans-1,4-cyclohexylene, 1,4-phenylene or pyrimidine-2,5-diyl group, the ring J is a trans-1,4-cyclohexylene group, a 1,4-phenylene or pyrimidine-2,5-diyl group in which one or more hydrogen atoms on the ring may be substituted by F, the ring K is a trans-1,4-cyclohexylene or 1,4-phenylene group, $Z_9$ and $Z_{11}$ are independently —COO—, —(CH$_2$)$_2$—, or a covalent bond, $Z_{10}$ is —CH=CH—, —C≡C—, —COO— or a covalent bond and h is 0 or 1.

9. The liquid crystal composition of claim 8, further comprising at least one compound selected from the group consisting of the compounds of formulae II-a, II-b and II-c:

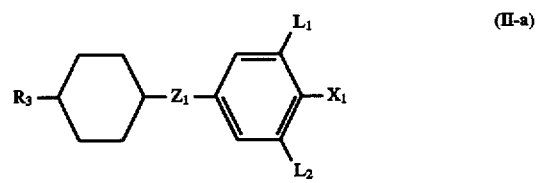
(II-a)

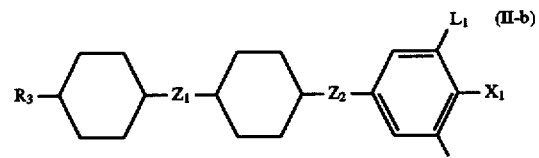
(II-b)

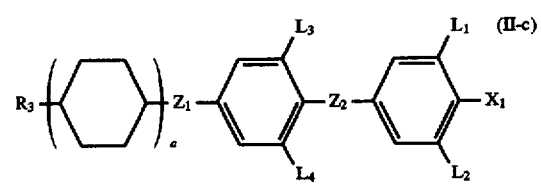
(II-c)

wherein $R_3$ is an alkyl group of 1–10 carbons, $X_1$ is F, Cl, OCF$_3$, OCF$_2$H, CF$_3$, CF$_2$H, or CFH$_2$, $L_1$, $L_2$, $L_3$ and $L_4$ are independently H or F, $Z_1$ and $Z_2$ are independently —(CH$_2$)$_2$—, —CH=CH— or a covalent bond and a is 1 or 2.

10. A liquid crystal display element comprising the liquid crystal compound set forth in any one of claims 1–5.

11. A liquid crystal display element comprising the liquid crystal composition set forth in claim 7.

12. A liquid crystal display element comprising the liquid crystal composition set forth in claim 8.

13. A liquid crystal display element comprising the liquid crystal composition set forth in claim 9.

14. The liquid crystal compound of claim 1, wherein rings $A_1$, $A_2$ and $A_3$ cannot each be a 1,4-cyclohexylene group at the same time.

* * * * *

UNITED STATES PATENT AND TRADEMARK OFFICE
CERTIFICATE OF CORRECTION

PATENT NO. : 5,709,820
DATED : JANUARY 20, 1998
INVENTOR(S) : TAKASHI KATO, ET AL.

It is certified that error appears in the above-identified patent and that said Letters Patent is hereby corrected as shown below:

Column 164, line 13, "or are replaced by —O—, —S—, [—C≡C—] or"

should read --or are replaced by —O—, —S—, or--.

Column 164, lines 19-20, "cyclohexene-1,4-diyl group a 1,3-dioxane-2,5, diyl group, a tetrahydropyrane-2,5, diyl group,"

should read --cyclohexene-1,4-diyl group, a 1,3-dioxane-2,5-diyl group, a tetrahydropyrane-2,5-diyl group,--

Signed and Sealed this

Twenty-third Day of June, 1998

Attest:

BRUCE LEHMAN

*Attesting Officer*　　　　*Commissioner of Patents and Trademarks*